(12) United States Patent
Blake et al.

(10) Patent No.: US 7,674,810 B2
(45) Date of Patent: Mar. 9, 2010

(54) 1,1-DIOXO-1H-1λ⁶-BENZO[D]ISOTHIAZOL-3-YL)-4-HYDROXY-1,5-DIHYDRO-PYRROL-2-ONE INHIBITORS OF HCV POLYMERASE

(75) Inventors: James F. Blake, Longmont, CO (US); Jay Bradford Fell, Longmont, CO (US); John P. Fischer, Longmont, CO (US); Robert Than Hendricks, San Carlos, CA (US); Stacey Renee Spencer, Lyons, CO (US); Peter J. Stengel, Longmont, CO (US)

(73) Assignee: Roche Palo Alto LLC, Palo Alto, CA (US)

( * ) Notice: Subject to any disclaimer, the term of this patent is extended or adjusted under 35 U.S.C. 154(b) by 766 days.

(21) Appl. No.: 11/413,872

(22) Filed: Apr. 28, 2006

(65) Prior Publication Data

US 2006/0252785 A1    Nov. 9, 2006

(51) Int. Cl.
*A01N 43/80* (2006.01)
(52) U.S. Cl. .................. 514/373; 548/206; 548/207
(58) Field of Classification Search ............... 548/206, 548/207; 514/373
See application file for complete search history.

(56) References Cited

U.S. PATENT DOCUMENTS

| | | | | |
|---|---|---|---|---|
| 4,868,188 | A | * | 9/1989 | Shutske ................ 514/273 |
| 6,339,098 | B1 | * | 1/2002 | Collins et al. ............. 514/373 |

FOREIGN PATENT DOCUMENTS

| | | |
|---|---|---|
| WO | WO 01/85172 A1 | 11/2001 |
| WO | WO 02/098424 A1 | 12/2002 |
| WO | WO 03/037262 A2 | 5/2003 |
| WO | WO 03/059356 A2 | 7/2003 |
| WO | WO 03/099801 A1 | 12/2003 |
| WO | WO 2004/041818 A1 | 5/2004 |
| WO | WO 2004/052312 A2 | 6/2004 |
| WO | WO 2004/052313 A2 | 6/2004 |
| WO | WO 2004/058150 A2 | 7/2004 |
| WO | WO 2005/019191 A2 | 3/2005 |

OTHER PUBLICATIONS

Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Dhanak, D., et al, "Identification and Biological Characterization of Heterocyclic Inhibitors of HCV RNA-dependent RNA polymerase", *J. Biol. Chem*, 2002 277(41):38322-38327.
Gu, B., et al, "Arresting Initiation of Hepatitis C Virus RNA synthesis using heterocyclic derivatives", *J. Biol. Chem.*, 2003 278(19):16602-16607.
Nguyen, T.T., et al, "Resistance profile of a hepatitis C virus RNA-dependent RNA polymerase benzothiadazine inhibitor", *Antimicrob. Agents and Chemother.*, 2003 47(11), 3525-30.

* cited by examiner

*Primary Examiner*—Kamal A Saeed
*Assistant Examiner*—Valerie Rodriguez-Garcia
(74) *Attorney, Agent, or Firm*—Brian L. Buckwalter

(57) ABSTRACT

Compounds having the formula i wherein m, $R^1$, $R^2$, $R^4$ and $X^1$ are herein defined are Hepatitis C virus NS5b polymerase inhibitors. Also disclosed are compositions and methods for inhibiting hepatitis replication, processes for making the compounds and synthetic intermediates used in the process.

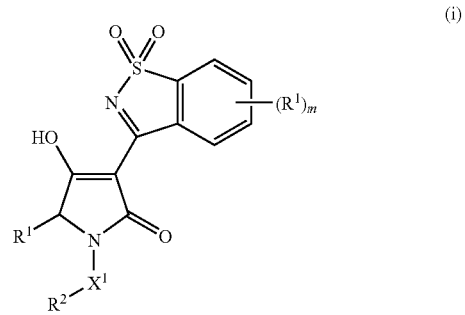

(i)

15 Claims, No Drawings

1,1-DIOXO-1H-1λ⁶-BENZO[D]ISOTHIAZOL-3-YL)-4-HYDROXY-1,5-DIHYDRO-PYRROL-2-ONE INHIBITORS OF HCV POLYMERASE

FIELD OF THE INVENTION

The present invention provides non-nucleoside compounds and certain derivatives thereof which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection. The invention further provides compositions containing the non-nucleoside compounds useful for treating HCV.

BACKGROUND

The invention relates to non-nucleoside derivatives as inhibitors of HCV replicon RNA replication. In particular, the invention is concerned with the use of heterocyclic compounds as inhibitors of subgenomic HCV RNA replication and pharmaceutical compositions containing such compounds.

Hepatitis C virus is the leading cause of chronic liver disease throughout the world (N. Boyer et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (C. M. Rice, *Flaviviridae: The viruses and their replication.* In: *Fields Virology*, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Foms and J. Bukh, *Clinics in Liver Disease* 1999 3:693-716; J. Bukh et al., *Semin. Liv. Dis.* 1995 15:41-63). Unfortunately Type 1 infection is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication.

Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.,* 1999 19:5; A. M. Di Besceglie and B. R. Bacon, *Scientific American,* October: 1999 80-85; G. Lake-Bakaar, *Current and Future Therapy for Chronic Hepatitis C Virus Liver Disease, Curr. Drug Targ. Infect Dis.* 2003 3(3):247-253; P. Hoffmann et al., *Recent patents on experimental therapy for hepatitis C virus infection* (1999-2002), *Exp. Opin. Ther. Patents* 2003 13(11):1707-1723; M. P. Walker et al., *Promising Candidates for the treatment of chronic hepatitis C, Exp. Opin. investing. Drugs* 2003 12(8): 1269-1280; S.-L. Tan et al., *Hepatitis C Therapeutics: Current Status and Emerging Strategies, Nature Rev. Drug Discov.* 2002 1:867-881; J. Z. Wu and Z. Hong, *Targeting NS5B RNA-Dependent RNA Polymerase for Anti-HCV Chemotherapy, Curr. Drug Targ.—Infect. Dis.* 2003 3(3):207-219.

Ribavirin (1-((2R,3R,4S,5R)-3,4-dihydroxy-5-hydroxymethyl-tetrahydro-furan-2-yl)-1H-[1,2,4]triazole-3-carboxylic acid amide; Virazole®) is a synthetic, non-interferon-inducing, broad spectrum antiviral nucleoside analog. Ribavirin has in vitro activity against several DNA and RNA viruses including Flaviviridae (G. L. Davis. *Gastroenterology* 2000 118: S104-S114). Although, in monotherapy ribavirin reduces serum amino transferase levels to normal in 40% or patients, it does not lower serum levels of HCV-RNA. Ribavirin also exhibits significant toxicity and is known to induce anemia. Viramidine is a prodrug converted to ribavirin in hepatocytes Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release,* 2001 72:217-224).

Combination therapy of HCV with ribavirin and interferon-α currently are optimal HCV therapy. Combining ribavirin and PEG-IFN (infra) results in a sustained viral response in 54-56% of patients. The SVR approaches 80% for type 2 and 3 HCV (Walker, supra). Unfortunately combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase.

The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interfere with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional constraints on any nucleoside. In addition this limits the direct evaluation of nucleosides as inhibitors of HCV replication to cell-based assays.

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al. WO 01/47833, H. Hashimoto et al. WO 03/0002s54, P. L. Beaulieu et al. WO 03/020240 A2; P. L. Beaulieu et al. U.S. Pat. No. 6,448,281 B1; P. L. Beaulieu et al. WO 03/007945 A1); indoles, (P. L. Beaulieu et al. WO 03/0010141 A2); benzothiadiazines, e.g., 1, (D. Dhanak et al. WO 01/85172 A1; D. Dhanak et al. WO 03/037262 A2; K. J. Duffy et al. WO03/099801 A1, D. Chai et al. WO 2004/0526313, J. K. Pratt et al. WO 2004/041818 A1; J. K. Pratt et al. WO 2004/087577 A1), thiophenes, C. K. Chan

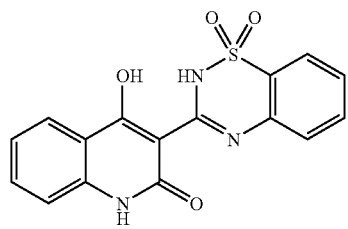

1 et al. WO 02/100851 A2); benzothiophenes (D. C. Young and T. R. Bailey WO 00/18231); β-ketopyruvates (S. Attamura et al. U.S. Pat. No. 6,492,423 B1, A. Attamura et al. WO 00/06529); pyrimidines (C. Gardelli et al. WO 02/06246 A1); pyrimidinediones (T. R. Bailey and D. C. Young WO 00/13708); triazines (K.-H. Chung et al. WO 02/079187 A1); rhodanine derivatives (T. R. Bailey and D. C. Young WO 00/10573, J. C. Jean et al. WO 01/77091 A2); 2,4-dioxopyrans (R. A. Love et al. EP 256628 A2); phenylalanine derivatives (M. Wang et al. *J. Biol. Chem.* 2003 278:2489-2495).

SUMMARY OF THE INVENTION

The present invention is directed toward novel heterocyclic compounds that inhibit HCV polymerase, methods of treating a disorder mediated by HCV with said compounds and pharmaceutical compositions containing said compound which compound possesses a structure according to formula

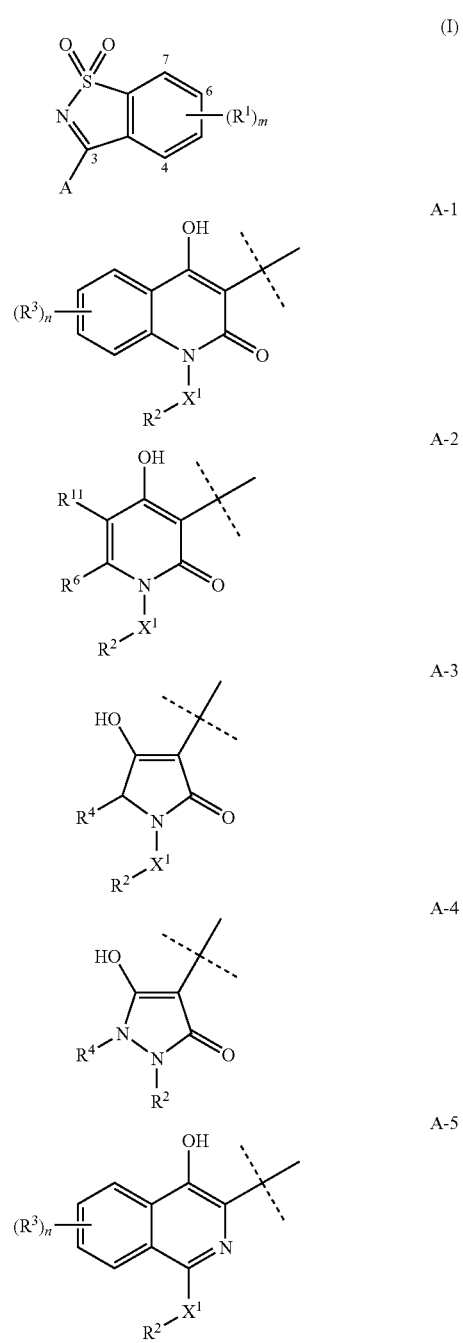

wherein:
A is selected from the grouping consisting of A-1, A-2, A-3, A-4 and A-5;
$X^1$ is —O—, —$NR^6$— or a bond;
$R^1$ in each occurrence is independently selected from the group consisting of $C_{1-6}$ alkyl, $C_{1-6}$ alkenyl, $C_{1-6}$ alkynyl, $C_{3-7}$ cycloalkyl, $C_{3-7}$ cycloalkyl-$C_{1-4}$ alkyl, $C_{1-6}$ alkoxy, optionally substituted phenyl, optionally substituted heteroaryl selected from the group consisting of pyridine, pyridone, pyrimidine, pyrimidone and imidazole, optionally substituted aryl-$C_{1-6}$ alkyl, $C_{1-6}$ hydroxyalkyl, $C_{1-3}$ alkoxy-$C_{1-6}$ alkyl, optionally substituted phenoxy, optionally substituted phenyl-$C_{1-3}$ alkoxy, $C_{1-6}$ heteroalkoxy, hydroxyl, halogen, $(CH_2)_{o_1}$ $NR^aR^b$, $X^2(CH_2)_uNR^aR^b$, $X^2(CH_2)_{o_1}COR^9$, $X^2(CH_2)_{o_1}$ $SO_2NR^cR^d$, $(CH_2)_{r_1}SO_2R^5$, $O(CH_2)_{o_1}SO_2$—$C_{1-6}$ alkyl, $COR^9$, nitro, and cyano wherein optionally substituted phenyl or heteroaryl groups are independently substituted with one to three substituents selected from the group consisting of $C_{1-3}$ alkyl, $C_{3-6}$-cycloalkyl, $C_{1-3}$ alkoxy, $C_{1-3}$ haloalkyl, halogen, $NR^cR^d$, cyano and nitro; or if m is 2 and the $R^1$ substituents are on adjacent carbons; taken together they can be —CH=CHCH=CH—;

$R^2$ in each occurrence is independently selected from the group consisting of hydrogen, $C_{1-6}$ alkyl, $C_{1-6}$ alkenyl, $C_{1-6}$ alkynyl, pyrid-2-on-5-ylmethyl, thien-2-ylmethyl, $C_{3-7}$ cycloalkyl, $C_{3-7}$ cycloalkyl-$C_{1-3}$ alkyl, $C_{1-6}$ heteroalkyl and phenyl-$C_{1-3}$ alkyl optionally substituted with one to three substituents selected from the group consisting of $C_{1-3}$ alkyl, $C_{3-6}$-cycloalkyl, $C_{1-3}$ alkoxy, $C_{1-3}$ haloalkyl, halogen, $NR^cR^d$, cyano and nitro;

$R^3$ in each occurrence is independently selected from the group consisting of $C_{1-6}$ alkyl, halogen, $C_{1-6}$ alkoxy, hydroxyl, cyano and nitro;

$R^4$ is hydrogen, $C_{1-6}$ alkyl, $C_{3-7}$ cycloalkyl, $C_{3-7}$ cycloalkyl-$C_{1-4}$alkyl, $C_{1-6}$ heteroalkyl, phenyl or phenyl-$C_{1-4}$ alkyl said phenyls optionally independently substituted with one to three $R^3$ radicals;

$R^5$ is $C_{1-6}$ alkyl, $C_{3-7}$ cycloalkyl, $C_{3-7}$ cycloalkyl-$C_{1-4}$ alkyl, —$NR^cR^d$, amino-$C_{1-6}$ alkyl, $C_{1-6}$ heteroalkyl, thiophen-2-yl, 1,2-dimethyl-imidazol-4-yl, phenyl or phenyl-$C_{1-3}$ alkyl said phenyl each optionally independently substituted with one to three $C_{1-3}$ alkyl, $C_{1-3}$ alkoxy, halogen, nitro or cyano;

$R^6$ is hydrogen or $C_{1-3}$ alkyl;

$R^{6a}$ and $R^{6b}$ are independently $R^6$;

$R^8$ is $C_{1-6}$ acyl or $R^6$;

$R^9$ is hydroxyl, $C_{1-6}$ alkoxy, amino, —$NR^cR^d$, providing that $R^9$ is other than hydroxyl when $o_1$ is zero;

$R^{10}$ is alkoxy, amino, —$NR^cR^d$, $C_{1-6}$ alkyl, $C_{3-7}$ cycloalkyl or $C_{1-6}$ heteroalkoxy;

$R^{11}$ is $C_{1-6}$ alkyl or phenyl;

$R^a$ and $R^b$ are (i) independently hydrogen, $C_{1-6}$ alkyl, $C_{1-6}$ acyl, $C_{1-6}$ heteroalkyl, $C_{1-6}$ alkyl-$C_{1-3}$ alkoxy, $C_{1-3}$ alkyl-amino-$C_{1-6}$ alkyl, or (ii) one of $R^a$ and $R^b$ is $(CH_2)_{r_2}$ $CONR^{6a}R^{6b}$, $COR^{10}$ or $(CH_2)_{o_2}SO_2R^5$, and the other of $R^a$ and $R^b$ is hydrogen, $C_{1-6}$ alkyl or $C_{1-6}$ acyl, or (iii) taken together are $(CH_2)_q$, $(CH_2)_wSO_2$, $(CH_2)_w$ $NR^6SO_2$, $(CH_2)_2X^3(CH_2)_2$, or taken together with the nitrogen atom to which they are attached are 3-amino pyrrolidine, 3-methylsulfonylpyrrolidine or 3-acetamido-pyrrolidine;

$R^c$ and $R^d$ are (i) independently hydrogen, $C_{1-6}$ alkyl, $C_{1-6}$ acyl, $C_{1-6}$ sulfonyl or $C_{1-6}$ heteroalkyl, or (ii) taken together are $(CH_2)_q$, $(CH_2)_2X^3(CH_2)_2$, or 3-hydroxy-pyrrolidin-1-yl;

$X^2$ is O, or $NR^6$;

$X^3$ is O or $NR^8$;

m is an integer from 0 to 3;

n is an integer from 0 to 2;

$o_1$ and $o_2$ are independently integers from 0 to 6;

q is an integer from 3 to 6;

$r_1$ and $r_2$ are independently integers from 1 to 6;

s is 0 or 1;

u is an integer from 2 to 6;

w is an integer from 2 to 4; and, pharmaceutically acceptable salts thereof.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the broadest definition for each group as provided in the Summary of the Invention.

In one embodiment of the present invention there is provided a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In one embodiment of the present invention there is provided a compound according to formula I wherein A is selected from the grouping consisting of A-1, A-2, A-3, A-4 and A-5; $X^1$ is —O—, —$NR^6$— or a bond; $R^1$ in each occurrence is independently selected from the group consisting of $C_{1-6}$ alkyl, $C_{1-6}$ alkenyl, $C_{1-6}$ alkynyl, $C_{3-7}$ cycloalkyl, $C_{3-7}$ cycloalkyl-$C_{1-4}$ alkyl, $C_{1-6}$ alkoxy, optionally substituted aryl, optionally substituted heteroaryl selected from the group consisting of pyridine, pyridone, pyrimidine, pyrimidone and imidazole, optionally substituted aryl-$C_{1-6}$ alkyl, $C_{1-6}$ hydroxyalkyl, $C_{1-3}$ alkoxy-$C_{1-6}$ alkyl, optionally substituted aryloxy, optionally substituted aryl-$C_{1-3}$ alkoxy, $C_{1-6}$ heteroalkoxy, hydroxyl, halogen, $(CH_2)_{o_1}NR^aR^b$, $X^2(CH_2)_u$ $NR^aR^b$, $X^2(CH_2)_{o_1}COR^9$, $X^2(CH_2)_{o_1}SO_2NR^cR^d$, $(CH_2)_{r_1}$ $SO_2R^5$, nitro, and cyano wherein optionally substituted aryl or heteroaryl groups are substituted with one to three substituents selected from the group consisting of $C_{1-3}$ alkyl, $C_{1-3}$ alkoxy, $C_{1-3}$ haloalkyl, halogen, $NR^cR^d$, cyano and nitro; or if m is 2 and the $R^1$ substituents are on adjacent carbons and taken they can be —CH=CHCH=CH—; $R^2$ in each occurrence is independently selected from the group consisting of hydrogen, $C_{1-6}$ alkyl, $C_{1-6}$ alkenyl, $C_{1-6}$ alkynyl, optionally substituted aryl-$C_{1-3}$ alkyl, pyrid-2-on-5-ylmethyl, thien-2-ylmethyl, $C_{3-7}$ cycloalkyl, $C_{3-7}$ cycloalkyl-$C_{1-3}$ alkyl and $C_{1-6}$ heteroalkyl; $R^3$ in each occurrence is independently selected from the group consisting of $C_{1-6}$ alkyl, halogen, $C_{1-6}$ alkoxy, hydroxyl, cyano and nitro; $R^4$ is hydrogen, $C_{1-6}$ alkyl, $C_{3-7}$ cycloalkyl, $C_{3-7}$ cycloalkyl-$C_{1-4}$ alkyl, $C_{1-6}$ heteroalkyl, aryl or aryl-$C_{1-4}$ alkyl said aryls optionally substituted independently with one to three $R^3$ radicals; $R^5$ is $C_{1-6}$ alkyl, $C_{3-7}$ cycloalkyl, $C_{3-7}$ cycloalkyl-$C_{1-4}$ alkyl, —$NR^cR^d$, $C_{1-6}$ heteroalkyl, aryl or aryl $C_{1-3}$ alkyl said aryl each optionally substituted independently with one to three $C_{1-3}$ alkyl, $C_{1-3}$ alkoxy, halogen, nitro or cyano; $R^6$ is hydrogen or $C_{1-3}$ alkyl; $R^{6a}$ and $R^{6b}$ are independently $R^6$; $R^8$ is $C_{1-6}$ acylamino or $R^6$; $R^9$ is hydroxyl, $C_{1-6}$ alkoxy, amino, —$NR^cR^d$, or providing $R^9$ is other than hydroxyl when $o_1$ is zero; $R^{10}$ is alkoxy, amino, —$NR^cR^d$, $C_{1-6}$ alkyl, $C_{3-7}$ cycloalkyl or $C_{1-6}$ heteroalkoxy; $R^{11}$ is $C_{1-6}$ alkyl or phenyl; $R^a$ and $R^b$ are (i) independently hydrogen, $C_{1-6}$ alkyl, $C_{1-6}$ acyl, $C_{1-6}$ heteroalkyl or (ii) one of $R^1$ and $R^b$ is $(CH_2)_{r_2}CONR^{6a}R^{6b}$, $COR^{10}$ or $(CH_2)_{o_2}SO_2R^5$, and the other of $R^a$ and $R^b$ is hydrogen, $C_{1-6}$ alkyl or $C_{1-6}$ acyl, or (iii) taken together are $(CH_2)_q$, $(CH_2)_wSO_2$ or $(CH_2)_2X^3(CH_2)_2$; $R^c$ and $R^d$ are (i) independently hydrogen, $C_{1-6}$ alkyl, $C_{1-6}$ heteroalkyl or (ii) taken together are $(CH_2)_q$, $(CH_2)_2X^3(CH_2)_2$, or 3-hydroxy-pyrrolidin-1-yl; $X^2$ is O, or $NR^6$; $X^3$ is O or $NR^8$; m is an integer from 0 to 3; n is an integer from 0 to 2; $o_1$ and $o_2$ are an integer from 0 to 6; q is an integer from 3 to 6; $r_1$ and $r_2$ are an integer from 1 to 6; s is 0 or 1; u is an integer from 2 to 6; w is an integer from 2 to 4; and, pharmaceutically acceptable salts thereof.

In another embodiment of the present invention there is provided a compound according to formula I-A-5 (I-A-5 refers to formula I wherein A is A-5) wherein $X^1$, $X^2$, $X^3$ $R^1$, $R^2$, $R^3$, $R^5$, $R^6$, $R^{6a}$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-5 wherein $X^1$ is absent; and, $X^2$, $X^3$ $R^1$, $R^2$, $R^3$, $R^5$, $R^6$, $R^{6a}$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-5 wherein $X^1$ is absent; $R^1$ is hydroxyl, $(CH_2)_{o_1}NR^aR^b$, $X^2(CH_2)_uNR^aR^b$, $X^2(CH_2)_{o_1}COR^9$, $X^2(CH_2)_{o_1}SO_2NR^cR^d$, $(CH_2)_{r_1}SO_2R^5$, aryl, heteroaryl or halogen wherein the aryl or heteroaryl groups are optionally substituted with one to three substituents selected from the group consisting of $C_{1-3}$ alkyl, $C_{1-3}$ alkoxy, $C_{1-3}$ haloalkyl, halogen, $NR^cR^d$, cyano and nitro; and, $R^2$ is $C_{1-6}$ alkyl, aryl-$C_{1-4}$ alkyl or $C_{3-7}$ cycloalkyl-$C_{1-4}$ alkyl. Other substituents encompassed within this embodiment and not specifically defined retain the definition provided herein above.

In another embodiment of the present invention there is provided a compound according to formula I-A-5 wherein $X^1$ is absent; $R^1$ is $(CH_2)_{o_1}NR^aR^b$ or $X^2(CH_2)_{o_1}SO_2NR^cR^d$; $R^2$ is $C_{1-6}$ alkyl, aryl-$C_{1-4}$ alkyl or $C_{3-7}$ cycloalkyl-$C_{1-4}$ alkyl; and, $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-5 wherein $X^1$ is absent; $R^1$ is $(CH_2)_{o_1}NR^aR^b$, or $X^2(CH_2)_{o_1}SO_2NR^cR^d$ and is attached to the 7-position of the 1,1-dioxo-1H-1$\lambda^6$-benzo[d]isothiazol-3-yl ring; $R^2$ is $C_{1-6}$ alkyl, aryl-$C_{1-4}$ alkyl or $C_{3-7}$ cycloalkyl-$C_{1-4}$ alkyl; and, $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-5 wherein $X^1$ is absent; $R^1$ is $(CH_2)_{o_1}NR^aR^b$ and is attached to the 7-position of the 1,1-dioxo-1H-1$\lambda^6$-benzo[d]isothiazol-3-yl ring; $o_1$ is zero to two; $R^a$ is $(CH_2)_{o_2}SO_2R^5$; $o_2$ is zero; $R^b$ is hydrogen; $R^2$ is $C_{1-6}$ alkyl, aryl-$C_{1-4}$ alkyl or $C_{3-7}$ cycloalkyl-$C_{1-4}$ alkyl; and, $R^5$ is $C_{1-6}$ alkyl, $C_{3-7}$ cycloalkyl, $C_{3-7}$cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-5 wherein $X^1$ is absent; $R^1$ is $X^2(CH_2)_{o_1}SO_2NR^cR^d$; and is attached to the 7-position of the 1,1-dioxo-1H-1$\lambda^6$-benzo[d]isothiazol-3-yl ring; $X^2$ is O; $o_1$ is one to three; $R^2$ is $C_{1-6}$ alkyl, aryl-$C_{1-4}$ alkyl or $C_{3-7}$ cycloalkyl-$C_{1-4}$ alkyl; and $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-3 wherein $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-3 wherein $X^1$ is absent; and $X^2$, $X^3$ $R^1$, $R^2$, $R^3$, $R^4$, $R^5$, $R^6$, $R^{6a}$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-3 wherein $X^1$ is absent; $R^1$ is hydroxyl, $(CH_2)_{o_1}NR^aR^b$, $X^2(CH_2)_uNR^aR^b$, $X^2(CH_2)_{o_1}COR^9$, $X^2(CH_2)_{o_1}SO_2NR^cR^d$, $(CH_2)_{r_1}SO_2R^5$, optionally substituted aryl, optionally substituted heteroaryl or halogen wherein the aryl and heteroaryl groups are optionally substituted with one to three substituents selected from the group consisting of $C_{1-3}$ alkyl, $C_{1-3}$ alkoxy, $C_{1-3}$ haloalkyl, halogen, $NR^cR^d$, cyano and nitro; $R^2$ is $C_{1-6}$ alkyl, aryl-$C_{1-4}$ alkyl or $C_{3-7}$ cycloalkyl-$C_{1-4}$ alkyl; and, $R^4$ is hydrogen, $C_{1-6}$ alkyl, $C_{3-7}$ cycloalkyl, aryl or aryl-$C_{1-4}$ alkyl said aryl optionally substituted independently with one to three substituent selected from $C_{1-6}$ alkyl, halogen, $C_{1-6}$ alkoxy, hydroxyl, cyano and nitro. Other substituents encompassed within this embodiment and not specifically defined retain the definition provided herein above.

In another embodiment of the present invention there is provided a compound according to formula I-A-3 wherein $X^1$ is absent; $R^1$ is $(CH_2)_{o_1}NR^aR^b$, $X^2(CH_2)_{o_1}COR^9$ or $X^2(CH_2)_{o_1}SO_2NR^cR^d$; m is one; $R^2$ is $C_{1-6}$ alkyl, aryl-$C_{1-4}$ alkyl or $C_{3-7}$ cycloalkyl-$C_{1-4}$ alkyl; $R^4$ is hydrogen, $C_{1-6}$ alkyl, $C_{3-7}$ cycloalkyl, aryl or aryl-$C_{1-4}$ alkyl wherein the aryl radicals are optionally substituted independently with one to three substituent selected from $C_{1-6}$ alkyl, halogen, $C_{1-6}$ alkoxy, hydroxyl, cyano and nitro; and $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-3 wherein $X^1$ is absent; $R^1$ is $CH_2NR^aR^b$; m is one; $R^2$ is optionally substituted phenyl-$C_{1-6}$ alkyl; $R^4$ is $C_{1-6}$ alkyl; $R^5$ is $C_{1-6}$ alkyl, optionally substituted phenyl or $NR^cR^d$; $R^a$ is hydrogen or $C_{1-6}$ alkyl and $R^b$ is $SO_2R^5$ or $R^a$ and $R^b$ together are $(CH_2)_w SO_2$ or $(CH_2)_w N(R^6)SO_2$ or $R^a$ and $R^b$ together with the nitrogen to which they are attached are piperazine, N-acetylpiperazine or N-methanesulfonylpiperazine. Other substituents encompassed within this embodiment and not specifically defined retain the definition provided herein above.

In another embodiment of the present invention there is provided a compound according to formula I-A-3 wherein $X^1$ is absent; $R^1$ is $CH_2NR^aR^b$; m is one; $R^2$ is optionally substituted phenyl-$C_{1-6}$ alkyl; $R^4$ is $C_{1-6}$ alkyl; $R^5$ is $C_{1-6}$ alkyl, optionally with 1 to 3 substitutents independently selected from fluorine, chlorine, $C_{1-6}$ alkyl, $C_{1-6}$ alkoxy or $NR^cR^d$; $R^a$ is hydrogen or $C_{1-6}$ alkyl and $R^b$ is $SO_2R^5$ or $R^a$ and $R^b$ together are $(CH_2)_w SO_2$ or $(CH_2)_w N(R^6)SO_2$ or $R^a$ and $R^b$ together with the nitrogen to which they are attached are piperazine, N-acetylpiperazine or N-methanesulfonylpiperazine. Other substituents encompassed within this embodiment and not specifically defined retain the definition provided herein above.

In another embodiment of the present invention there is provided a compound according to formula I-A-3 wherein $X^1$ is absent; $R^1$ is $(CH_2)_{o_1}NR^aR^b$, $X^2(CH_2)_{o_1}COR^9$ or $X^2(CH_2)_{o_1}SO_2NR^cR^d$ and the $R^1$ substituent is attached to the 7-position of the 1,1-dioxo-1H-1$\lambda^6$-benzo[d]isothiazol-3-yl ring; m is one; $R^2$ is $C_{1-6}$ alkyl, aryl-$C_{1-4}$ alkyl or $C_{3-7}$ cycloalkyl-$C_{1-4}$ alkyl; $R^4$ is hydrogen, $C_{1-6}$ alkyl, $C_{3-7}$ cycloalkyl, aryl or aryl-$C_{1-4}$ alkyl wherein the aryl groups are optionally substituted independently with one to three substituent selected from $C_{1-6}$ alkyl, halogen, $C_{1-6}$ alkoxy, hydroxyl, cyano and nitro; and $R^5$ is $C_{1-6}$ alkyl, $C_{3-7}$ cycloalkyl, $C_{3-7}$ cycloalkyl- $C_{1-4}$ alkyl or $NR^cR^d$. Other substituents encompassed within this embodiment and not specifically defined retain the definition provided herein above.

In another embodiment of the present invention there is provided a compound according to formula I-A-3 wherein $X^1$ is absent; $R^1$ is $(CH_2)_{o1}NR^aR^b$ and is attached to the 7-position of the 1,1-dioxo-1H-1-benzo[d]isothiazol-3-yl ring; m is one; $o_1$ is zero to two; $R^1$ is $SO_2R^5$; $R^b$ is hydrogen; $R^2$ is $C_{1-6}$ alkyl, aryl-$C_{1-4}$ alkyl or $C_{3-7}$ cycloalkyl-$C_{1-4}$ alkyl; $R^4$ is hydrogen, $C_{1-6}$ alkyl, $C_{3-7}$ cycloalkyl, aryl or aryl-$C_{1-4}$ alkyl wherein the aryl groups are optionally substituted independently with one to three substituent selected from $C_{1-6}$ alkyl, halogen, $C_{1-6}$ alkoxy, hydroxyl, cyano and nitro; and $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-3 wherein $X^1$ is absent; $R^1$ is $X^2(CH_2)_{o1}SO_2NR^cR^d$ and is attached to the 7-position of the 1,1-dioxo-1H-1$\lambda^6$-benzo[d]isothiazol-3-yl ring; m is one; $X^2$ is oxygen; $o_1$ is one to three; $R^2$ is $C_{1-6}$ alkyl, aryl-$C_{1-4}$ alkyl or $C_{3-7}$ cycloalkyl-$C_{1-4}$ alkyl; $R^4$ is hydrogen, $C_{1-6}$ alkyl, $C_{3-7}$ cycloalkyl, aryl or aryl-$C_{1-4}$ alkyl; and, said aryl optionally substituted independently with one to three substituents selected from $C_{1-6}$ alkyl, halogen, $C_{1-6}$ alkoxy, hydroxyl, cyano and nitro. Other substituents encompassed within this embodiment and not specifically defined retain the definition provided herein above.

In another embodiment of the present invention there is provided a compound according to formula I-A-3 wherein $X^1$ is absent; $R^1$ is $X^2(CH_2)_{o1}COR^9$ and is attached to the 7-position of the 1,1-dioxo-1H-1$\lambda^6$-benzo[d]isothiazol-3-yl ring; m is one; $X^2$ is oxygen; $o_1$ is an integer from one to three; $R^2$ is $C_{1-6}$ alkyl, aryl-$C_{1-4}$ alkyl or $C_{3-7}$ cycloalkyl-$C_{1-4}$ alkyl; $R^4$ is hydrogen, $C_{1-6}$ alkyl, $C_{3-7}$ cycloalkyl, aryl or aryl-$C_{1-4}$ alkyl; and, wherein the aryl rings are optionally substituted independently with one to three substituents selected from $C_{1-6}$ alkyl, halogen, $C_{1-6}$ alkoxy, hydroxyl, cyano and nitro. Other substituents encompassed within this embodiment and not specifically limited retain the broadest definition provided herein above.

In another embodiment of the present invention there is provided a compound according to formula I-A-3 wherein X is absent; $R^1$ is aryl or heteroaryl ring attached to the 7-position of the 1,1-dioxo-1H-1$\lambda^6$-benzo[d]isothiazol-3-yl ring; m is one and the aryl or heteroaryl ring is optionally substituted with one to three substituents selected from the group consisting of $C_{1-3}$ alkyl, $C_{1-3}$ alkoxy, $C_{1-3}$ haloalkyl, halogen, $NR^cR^d$, cyano and nitro. Other substituents encompassed within this embodiment and not specifically limited retain the broadest definition provided herein above.

In another embodiment of the present invention there is provided a compound according to formula I-A-2 wherein $X^1$, $X^2$, $X^3$ $R^1$, $R^2$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-2 wherein m is one; $R^1$ is $(CH_2)$. $NR^aR^b$, or $X^2(CH_2)_{o1}SO_2NR^cR^d$ and is attached to the 7-position of the 1,1-dioxo-1H-1$\lambda^6$-benzo[d]isothiazol-3-yl ring; m is one; and $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I-A-4 wherein $X^2$, $X^3$ $R^1$, $R^2$, $R^3$, $R^4$, $R^5$, $R^6$, $R^{6a}$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-4 wherein m is one; $R^1$ is $(CH_2)_{o1}NR^aR^b$ or $X^2(CH_2)_{o1}SO_2NR^cR^d$ and the $R^1$ substituent is on the 7-position of the 1,1-dioxo-1H-1$\lambda^6$-benzo[d]isothiazol-3-yl ring; m is one; and $R^1$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above In another embodiment of the present invention there is provided a compound according to formula I-A-1 wherein $X^1$, $X^2$, $X^3$ $R^1$, $R^2$, $R^3$, $R^5$, $R^6$, $R^6$, $R^{6b}$, $R^8$, $R^9$, $R^{10}$, $R^a$, $R^b$, $R^c$, $R^d$, m, n, $o_1$, $o_2$, q, $r_1$, $r_2$, s, u and w are as defined herein above.

In another embodiment of the present invention there is provided a compound according to formula I-A-1 wherein m is one; $R^1$ is $(CH_2)_{o1}NR^aR^b$, or $X^2(CH_2)_{o1}SO_2NR^cR^d$ and is attached to the 7-position of the 1,1-dioxo-1H-1$\lambda^6$-benzo[d]isothiazol-3-yl ring; m is one; and $R^5$ is $C_{1-6}$ alkyl, $C_{3-7}$ cycloalkyl, $C_{3-7}$ cycloalkyl-$C_{1-4}$ alkyl or $NR^cR^d$. Other substituents encompassed within this embodiment and not specifically defined retain the definition provided herein above.

In another embodiment of the present invention there is provided a compound according to formula I wherein the compound is:

3-(1,1-Dioxo-1H-1$\lambda^6$-benzo[d]isothiazol-3-yl)-1-(3-methyl-butyl)-isoquinolin-4-ol;

3-(1,1-Dioxo-1H-1$\lambda^6$-benzo[d]isothiazol-3-yl)-1-(4-fluoro-benzyl)-isoquinolin-4-ol;

1-(2-Cyclopropyl-ethyl)-3-(1,1-dioxo-1H-1$\lambda^6$-benzo[d]isothiazol-3-yl)-isoquinolin-4-ol;

3-(1,1-Dioxo-1H-1$\lambda^6$-benzo [d]isothiazol-3-yl)-6-fluoro-1-(4-fluoro-benzyl)-isoquinolin-4-ol;

3-(1,1-Dioxo-1H-1$\lambda^6$-benzo[d]isothiazol-3-yl)-1-(4-fluoro-benzyl)-6-methyl-isoquinolin-4-ol;

3-(7-Chloro-1,1-dioxo-1H-1$\lambda^6$-benzo[d]isothiazol-3-yl)-1-(4-fluoro-benzyl)-isoquinolin-4-ol;

3-(1,1-Dioxo-1H-1$\lambda^6$-benzo[d]isothiazol-3-yl)-1-[(4-fluoro-phenyl)-methyl-amino]-isoquinolin-4-ol;

1-(Cyclopropylmethyl-amino)-3-(1,1-dioxo-1H-1$\lambda^6$-benzo[d]isothiazol-3-yl)-isoquinolin-4-ol;

1-(4-Fluoro-benzyl)-3-(7-methyl-1,1-dioxo-1H-1$\lambda^6$-benzo[d]isothiazol-3-yl)-isoquinolin-4-ol;

1-(4-Fluoro-benzyl)-3-(7-methoxy-1,1-dioxo-1H-1$\lambda^6$-benzo[d]isothiazol-3-yl)-isoquinolin-4-ol;

1-(4-Fluoro-benzyl)-3-(7-morpholin-4-yl-1,1-dioxo-1H-1$\lambda^6$-benzo[d]isothiazol-3-yl)-isoquinolin-4-ol;

3-(1,1-Dioxo-7-phenyl-1H-1$\lambda^6$-benzo[d]isothiazol-3-yl)-1-(4-fluoro-benzyl)-isoquinolin-4-ol;

1-(4-Fluoro-benzyl)-3-[7-(3-hydroxy-phenyl)-1,1-dioxo-1H-1$\lambda^6$-benzo[d]isothiazol-3-yl]-isoquinolin-4-ol;

1-(4-Fluoro-benzyl)-3-[7-(4-fluoro-phenyl)-1,1-dioxo-1H-1$\lambda^6$-benzo[d]isothiazol-3-yl]-isoquinolin-4-ol;

3-(1,1-Dioxo-7-m-tolyl-1H-1$\lambda^6$-benzo[d]isothiazol-3-yl)-1-(4-fluoro-benzyl)-isoquinolin-4-ol;

N-(3-{3-[1-(4-Fluoro-benzyl)-4-hydroxy-isoquinolin-3-yl]-1,1-dioxo-1H-1$\lambda^6$-benzo[d]isothiazol-7-yl}-phenyl)-acetamide;

1-(4-Fluoro-benzyl)-3-[7-(3-fluoro-phenyl)-1,1-dioxo-1H-1$\lambda^6$-benzo[d]isothiazol-3-yl]-isoquinolin-4-ol;

N-(3-{3-[1-(4-Fluoro-benzyl)-4-hydroxy-isoquinolin-3-yl]-1,1-dioxo-1H-1$\lambda^6$-benzo[d]isothiazol-7-yl}-phenyl)-methanesulfonamide;

3-(1,1-Dioxo-7-pyridin-3-yl-1H-1$\lambda^6$-benzo[d]isothiazol-3-yl)-1-(4-fluoro-benzyl)-isoquinolin-4-ol;

3-(7-Chloro-1,1-dioxo-1H-1λ⁶-benzo[d]isothiazol-3-yl)-6-fluoro-1-(4-fluoro-benzyl)-isoquinolin-4-ol;

N-{3-[1-(4-Fluoro-benzyl)-4-hydroxy-isoquinolin-3-yl]-1,1-dioxo-1H-1λ⁶-benzo[d]isothiazol-7-yl}-methanesulfonamide;

3-[1,1-Dioxo-7-(1H-pyrazol-4-yl)-1H-1λ⁶-benzo[d]isothiazol-3-yl]-1-(4-fluoro-benzyl)-isoquinolin-4-ol;

1-(4-Fluoro-benzyl)-3-[7-(6-methoxy-pyridin-3-yl)-1,1-dioxo-1H-1λ⁶-benzo[d]isothiazol-3-yl]-isoquinolin-4-ol;

3-(1,1-Dioxo-7-pyrimidin-5-yl-1H-1λ⁶-benzo[d]isothiazol-3-yl)-1-(4-fluoro-benzyl)-isoquinolin-4-ol;

5-{3-[1-(4-Fluoro-benzyl)-4-hydroxy-isoquinolin-3-yl]-1,1-dioxo-1H-1λ⁶-benzo[d]isothiazol-7-yl}-1H-pyridin-2-one;

N-{3-[1-(4-Fluoro-benzyl)-4-hydroxy-isoquinolin-3-yl]-1,1-dioxo-1H-1λ⁶-benzo[d]isothiazol-6-yl}-methanesulfonamide;

6-{3-[1-(4-Fluoro-benzyl)-4-hydroxy-isoquinolin-3-yl]-1,1-dioxo-1H-1λ⁶-benzo[d]isothiazol-7-yl}-1H-pyridin-2-one;

3-(7-Chloro-1,1-dioxo-1H-1λ⁶-benzo[d]isothiazol-3-yl)-1-(4-fluoro-benzyl)-4-methoxy-isoquinoline;

(S)-1-Benzyl-5-cyclohexyl-3-(1,1-dioxo-1H-1λ⁶-benzo[d]isothiazol-3-yl)-4-hydroxy-1,5-dihydro-pyrrol-2-one;

(S)-1-Benzyl-5-tert-butyl-3-(1,1-dioxo-1H-1λ⁶-benzo[d]isothiazol-3-yl)-4-hydroxy-1,5-dihydro-pyrrol-2-one;

(S)-5-tert-Butyl-3-(1,1-dioxo-1H-1λ⁶-benzo[d]isothiazol-3-yl)-1-(4-fluoro-benzyl)-4-hydroxy-1,5-dihydro-pyrrol-2-one;

(S)-5-tert-Butyl-3-(7-chloro-1,1-dioxo-1H-1λ⁶-benzo[d]isothiazol-3-yl)-1-(4-fluoro-benzyl)-4-hydroxy-1,5-dihydro-pyrrol-2-one;

(S)-5-tert-Butyl-1-(4-fluoro-benzyl)-4-hydroxy-3-(7-methoxy-1,1-dioxo-1H-1λ⁶-benzo[d]isothiazol-3-yl)-1,5-dihydro-pyrrol-2-one;

(S)-5-tert-Butyl-1-(4-fluoro-benzyl)-4-hydroxy-3-(7-hydroxy-1,1-dioxo-1H-1λ⁶-benzo[d]isothiazol-3-yl)-1,5-dihydro-pyrrol-2-one;

(S)-5-tert-Butyl-3-(1,1-dioxo-1H-1λ⁶-naphtho[2,1-d]isothiazol-3-yl)-1-(4-fluoro-benzyl)-4-hydroxy-1,5-dihydro-pyrrol-2-one;

(S)-3-(7-Chloro-1,1-dioxo-1H-1λ⁶-benzo[d]isothiazol-3-yl)-1-(4-fluoro-benzyl)-4-hydroxy-5-isobutyl-1,5-dihydro-pyrrol-2-one;

(S)-5-tert-Butyl-3-(1,1-dioxo-1H-1λ⁶-benzo[d]isothiazol-3-yl)-4-hydroxy-1-(4-methyl-benzyl)-1,5-dihydro-pyrrol-2-one;

(S)-5-tert-Butyl-3-(1,1-dioxo-1H-1λ⁶-benzo[d]isothiazol-3-yl)-1-(4-fluoro-3-methoxy-benzyl)-4-hydroxy-1,5-dihydro-pyrrol-2-one;

(S)-5-tert-Butyl-3-(1,1-dioxo-1H-1λ⁶-benzo[d]isothiazol-3-yl)-4-hydroxy-1-thiophen-2-ylmethyl-1,5-dihydro-pyrrol-2-one;

(S)-5-Cyclohexyl-3-(1,1-dioxo-1H-1λ⁶-benzo[d]isothiazol-3-yl)-1-(4-fluoro-benzyl)-4-hydroxy-1,5-dihydro-pyrrol-2-one; sodium salt;

(S)-5-tert-Butyl-1-(4-chloro-benzyl)-3-(1,1-dioxo-1H-1λ⁶-benzo[d]isothiazol-3-yl)-4-hydroxy-1,5-dihydro-pyrrol-2-one;

4-[(S)-2-tert-Butyl-4-(1,1-dioxo-1H-1λ⁶-benzo[d]isothiazol-3-yl)-3-hydroxy-5-oxo-2,5-dihydro-pyrrol-1-ylmethyl]-benzonitrile;

(S)-5-tert-Butyl-3-(1,1-dioxo-1H-1λ⁶-benzo[d]isothiazol-3-yl)-1-(4-fluoro-3-methyl-benzyl)-4-hydroxy-1,5-dihydro-pyrrol-2-one;

(S)-5-((S)-sec-Butyl)-3-(1,1-dioxo-1H-1λ⁶-benzo[d]isothiazol-3-yl)-1-(4-fluoro-benzyl)-4-hydroxy-1,5-dihydro-pyrrol-2-one;

(S)-5-tert-Butyl-1-cyclobutylmethyl-3-(1,1-dioxo-1H-1λ⁶-benzo[d]isothiazol-3-yl)-4-hydroxy-1,5-dihydro-pyrrol-2-one;

(S)-3-(1,1-Dioxo-1H-1λ⁶-benzo[d]isothiazol-3-yl)-1-(4-fluoro-benzyl)-4-hydroxy-5-isobutyl-1,5-dihydro-pyrrol-2-one;

3-(1,1-Dioxo-1H-1λ⁶-benzo[d]isothiazol-3-yl)-1-(4-fluoro-benzyl)-4-hydroxy-5-isobutyl-1,5-dihydro-pyrrol-2-one;

(R)-3-(1,1-Dioxo-1H-1λ⁶-benzo[d]isothiazol-3-yl)-1-(4-fluoro-benzyl)-4-hydroxy-5-isobutyl-1,5-dihydro-pyrrol-2-one;

(S)-5-tert-Butyl-1-(3,3-dimethyl-butyl)-3-(1,1-dioxo-1H-1λ⁶-benzo[d]isothiazol-3-yl)-4-hydroxy-1,5-dihydro-pyrrol-2-one;

(S)-1-(3-Bromo-4-fluoro-benzyl)-5-tert-butyl-3-(1,1-dioxo-1H-1λ⁶-benzo[d]isothiazol-3-yl)-4-hydroxy-1,5-dihydro-pyrrol-2-one;

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide;

(S)-5-tert-Butyl-1-(3,4-difluoro-benzyl)-3-(1,1-dioxo-1H-1λ⁶-benzo[d]isothiazol-3-yl)-4-hydroxy-1,5-dihydro-pyrrol-2-one;

5-[(S)-2-tert-Butyl-4-(1,1-dioxo-1H-1λ⁶-benzo[d]isothiazol-3-yl)-3-hydroxy-5-oxo-2,5-dihydro-pyrrol-1-ylmethyl]-2-fluoro-benzonitrile;

(S)-5-tert-Butyl-3-(1,1-dioxo-1H-1λ⁶-benzo[d]isothiazol-3-yl)-1-(4-fluoro-3-trifluoromethyl-benzyl)-4-hydroxy-1,5-dihydro-pyrrol-2-one;

(S)-3-(1,1-Dioxo-1H-1λ⁶-benzo[d]isothiazol-3-yl)-1-(4-fluoro-benzyl)-4-hydroxy-5-phenyl-1,5-dihydro-pyrrol-2-one;

(S)-5-Benzyl-3-(1,1-dioxo-1H-1λ⁶-benzo[d]isothiazol-3-yl)-1-(4-fluoro-benzyl)-4-hydroxy-1,5-dihydro-pyrrol-2-one;

5-[(S)-2-tert-Butyl-4-(1,1-dioxo-1H-1λ⁶-benzo[d]isothiazol-3-yl)-3-hydroxy-5-oxo-2,5-dihydro-pyrrol-1-ylmethyl]-1H-pyridin-2-one;

(S)-5-tert-Butyl-1-(3-cyclopropyl-4-fluoro-benzyl)-3-(1,1-dioxo-1H-1λ⁶-benzo[d]isothiazol-3-yl)-4-hydroxy-1,5-dihydro-pyrrol-2-one;

(S)-5-tert-Butyl-1-(3-chloro-4-fluoro-benzyl)-3-(1,1-dioxo-1H-1λ⁶-benzo[d]isothiazol-3-yl)-4-hydroxy-1,5-dihydro-pyrrol-2-one;

(S)-5-tert-Butyl-3-(1,1-dioxo-7-pyridin-3-yl-1H-1λ⁶-benzo[d]isothiazol-3-yl)-1-(4-fluoro-benzyl)-4-hydroxy-1,5-dihydro-pyrrol-2-one;

(S)-5-tert-Butyl-1-(4-fluoro-benzyl)-4-hydroxy-3-[7-(6-methoxy-pyridin-3-yl)-1,1-dioxo-1H-1λ⁶-benzo[d]isothiazol-3-yl]-1,5-dihydro-pyrrol-2-one;

5-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-yl}-1H-pyridin-2-one;

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-N-methyl-methanesulfonamide;

(S)-5-tert-Butyl-1-(4-fluoro-benzyl)-4-hydroxy-3-[7-(2-methoxy-pyrimidin-5-yl)-1,1-dioxo-1H-1λ⁶-benzo[d]isothiazol-3-yl]-1,5-dihydro-pyrrol-2-one;

N-(3-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-yl}-phenyl)-acetamide;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

Dimethylamino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide 2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-acetamide;

Amino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

Pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

5-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-1H-pyrimidin-2-one;

(S)-5-tert-Butyl-3-(1,1-dioxo-7-pyrimidin-5-yl-1H-1$\lambda^6$-benzo[d]isothiazol-3-yl)-1-(4-fluoro-benzyl)-4-hydroxy-1,5-dihydro-pyrrol-2-one;

Cyclopropanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

Ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

6-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-1H-pyridin-2-one;

(S)-5-tert-Butyl-3-[1,1-dioxo-7-(1H-pyrazol-4-yl)-1H-1$\lambda^6$-benzo[d]isothiazol-3-yl]-1-(4-fluoro-benzyl)-4-hydroxy-1,5-dihydro-pyrrol-2-one;

(R)-5-tert-Butyl-3-(1,1-dioxo-1H-1$\lambda^6$-benzo[d]isothiazol-3-yl)-1-(4-fluoro-benzyl)-4-hydroxy-1,5-dihydro-pyrrol-2-one;

(S)-5-tert-Butyl-3-(1,1-dioxo-1H-1$\lambda^6$-benzo[d]isothiazol-3-yl)-1-(3-ethyl-4-fluoro-benzyl)-4-hydroxy-1,5-dihydro-pyrrol-2-one;

(S)-3-(7-Amino-1,1-dioxo-1H-1$\lambda^6$-benzo[d]isothiazol-3-yl)-5-tert-butyl-1-(4-fluoro-benzyl)-4-hydroxy-1,5-dihydro-pyrrol-2-one;

2-({3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amino)-acetamide;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-acetamide;

(S)-5-tert-Butyl-3-[7-(1,1-dioxo-1$\lambda^6$-isothiazolidin-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methylcarbamoylmethyl-acetamide;

N-{3-[(S)-5-tert-Butyl-1-(4-fluoro-3-methoxy-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-N,N-dimethyl-acetamide;

2-({3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amino)-N-methyl-acetamide;

N-{3-[(S)-5-tert-Butyl-1-(3-chloro-4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide;

2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N,N-dimethyl-acetamide;

(S)-5-tert-Butyl-1-(2-cyclopropyl-ethyl)-3-(1,1-dioxo-1H-1$\lambda^6$-benzo[d]isothiazol-3-yl)-4-hydroxy-1,5-dihydro-pyrrol-2-one;

(S)-3-(1,1-Dioxo-1H-1$\lambda^6$-benzo[d]isothiazol-3-yl)-1-(4-fluoro-benzyl)-4-hydroxy-5-isopropyl-1,5-dihydro-pyrrol-2-one;

{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-methanesulfonamide;

2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-acetamide;

2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetamide, ammonium salt;

{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetic acid ethyl ester;

(S)-3-Hydroxy-pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

N-{3-[(S)-1-(3-Bromo-4-fluoro-benzyl)-5-tert-butyl-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-Cyclohexyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-Butyl-1-(2-cyclopentyl-ethyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[1-(4-Fluoro-3-methyl-benzyl)-5-(4-fluoro-phenyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-benzenesulfonamide;

1-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-3-methyl-urea;

(S)-5-tert-Butyl-1-(4-fluoro-benzyl)-4-hydroxy-3-[7-(2-methanesulfonyl-ethyl)-1,1-dioxo-1H-1$\lambda^6$-benzo[d]isothiazol-3-yl]-1,5-dihydro-pyrrol-2-one;

(S)-5-tert-Butyl-1-(4-fluoro-benzyl)-4-hydroxy-3-(7-methyl-1,1-dioxo-1H-1$\lambda^6$-benzo[d]isothiazol-3-yl)-1,5-dihydro-pyrrol-2-one;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-methanesulfonamide;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-sulfamide;

2-Amino-ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide, hydrochloride salt;

(S)-5-tert-Butyl-1-(4-fluoro-benzyl)-4-hydroxy-3-(7-isobutoxy-1,1-dioxo-1H-1$\lambda^6$-benzo[d]isothiazol-3-yl)-1,5-dihydro-pyrrol-2-one;

(S)-5-tert-Butyl-1-(4-fluoro-benzyl)-4-hydroxy-3-(7-methanesulfonylmethoxy-1,1-dioxo-1H-1$\lambda^6$-benzo[d]isothiazol-3-yl)-1,5-dihydro-pyrrol-2-one;

Dimethyl-sulfamic acid 3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl ester;

{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-N',N'-dimethyl-sulfamide;

(S)-5-tert-Butyl-3-[7-(1,1-dioxo-1$\lambda^6$-[1,2]thiazinan-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo [d]isothiazol-7-ylmethyl}-N-(2-methoxy-ethyl)-methanesulfonamide;

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-(2-methylamino-ethyl)-methanesulfonamide, hydrochloride salt;

(S)-5-tert-Butyl-1-(4-fluoro-benzyl)-3-(4-fluoro-1,1-dioxo-1H-1$\lambda^6$-benzo[d]isothiazol-3-yl)-4-hydroxy-1,5-dihydro-pyrrol-2-one;

C-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-methanesulfonamide;

Morpholine-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide, trifluoroacetate salt;

4-Acetyl-piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-propionyl-methanesulfonamide;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-butyryl-methanesulfonamide;

(S)-5-tert-Butyl-1-(4-fluoro-benzyl)-4-hydroxy-3-(7-methylaminomethyl-1,1-dioxo-1H-1$\lambda^6$-benzo[d]isothiazol-3-yl)-1,5-dihydro-pyrrol-2-one; 2,2,3,3,4,4,4-heptafluoro-butyrate salt;

(S)-5-tert-Butyl-3-(7-dimethylaminomethyl-1,1-dioxo-1H-1$\lambda^6$-benzo[d]isothiazol-3-yl)-1-(4-fluoro-benzyl)-4-hydroxy-1,5-dihydro-pyrrol-2-one; 2,2,3,3,4,4,4-heptafluoro-butyrate salt;

(S)-3-(7-Aminomethyl-1,1-dioxo-1H-1$\lambda^6$-benzo[d]isothiazol-3-yl)-5-tert-butyl-1-(4-fluoro-benzyl)-4-hydroxy-1,5-dihydro-pyrrol-2-one; 2,2,3,3,4,4,4-heptafluoro-butyrate salt;

Piperazine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide, trifluoroacetate salt;

Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methyl-amide, trifluoroacetate salt;

3-Amino-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide, trifluoroacetate salt;

N-[1-({3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-sulfamoyl)-pyrrolidin-3-yl]-acetamide;

3-Methanesulfonyl-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

C-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-yloxy}-N,N-dimethyl-methanesulfonamide;

(S)-5-tert-Butyl-3-[7-(1,1-dioxo-1$\lambda^6$-[1,2,6]thiadiazinan-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one;

Thiophene-2-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

1,2-Dimethyl-1H-imidazole-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide, trifluoroacetate salt;

1-(2-Cyclopropyl-ethyl)-3-(1,1-dioxo-1H-1$\lambda^6$-benzo[d]isothiazol-3-yl)-6-fluoro-4-hydroxy-1H-quinolin-2-one; or, 1-tert-Butyl-4-(1,1-dioxo-1H-1$\lambda^6$-benzo[d]isothiazol-3-yl)-2-(4-fluoro-benzyl)-5-hydroxy-1,2-dihydro-pyrazol-3-one;

In another embodiment of the present invention there is provided a method for treating a disease caused by the Hepatitis C Virus (HCV) virus comprising administering to a patient in need thereof, a therapeutically effective quantity of a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a method for treating a disease caused by the Hepatitis C Virus (HCV) virus comprising co-administering to a patient in need thereof, at least one immune system modulator and/or at least one antiviral agent in combination with a therapeutically effective quantity of a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a method for treating a disease caused by the Hepatitis C Virus (HCV) virus comprising co-administering to a patient in need thereof, at least one interferon, interleukin, tumor necrosis factor or colony stimulating factor in combination with a therapeutically effective quantity of a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a method for treating a disease caused by the Hepatitis C Virus (HCV) virus comprising co-administering to a patient in need thereof, at least one interferon or chemically derivatized interferon in combination with a therapeutically effective quantity of a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a method for treating a disease caused by the Hepatitis C Virus (HCV) virus comprising co-administering to a patient in need thereof, at least one antiviral compound is selected from the group consisting of a HCV protease inhibitor, another HCV polymerase inhibitor, a HCV helicase inhibitor, a HCV primase inhibitor and a HCV fusion inhibitor in combination with a therapeutically effective quantity of a compound according to formula I wherein A, $X^1$, $X^2$, $X^3$ $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above.

In another embodiment of the present invention there is provided a pharmaceutical composition comprising a therapeutically effective quantity of a compound according to formula I wherein A, $X^1$, $X^2$, $X^3$, $R^1$, $R^2$, $R^3$, $R^4$, $R^5$, $R^6$, $R^{6a}$, $R^{6b}$, $R^8$, $R^9$, $R^{10}$, $R^{11}$, $R^a$, $R^b$, $R^c$, $R^d$, m, n, $o_1$, $o_2$, q, $r_1$, $r_2$, s, u and w are as defined herein above admixed with at least one pharmaceutically acceptable carrier, diluent or excipient.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term (ar)alkyl refers to either an unsubstituted alkyl or an aralkyl group. The term (hetero)aryl refers to either an aryl or a heteroaryl group.

"Optional" or "optionally" means that a subsequently described event or circumstance may, but need not occur, and that the description includes instances where the event or circumstance occurs and instances in which it does not. For example, "optional bond" means that the bond may or may not be present, and that the description includes single, double, or triple bonds.

If a substituent is designated to be a "bond" or "absent", the atoms linked to the substituents are then directly connected.

The term "acyl" or "alkylcarbonyl" as used herein denotes a group of formula —C(═O)R wherein R is hydrogen or lower alkyl as defined herein. The term "arylcarbonyl" as used herein means a group of formula C(═O)R wherein R is an aryl group; the term "benzoyl" as used herein refers to an "arylcarbonyl" group wherein R is phenyl.

The term "acylamino" as used herein denotes a group of formula —NHC(═O)R wherein R is hydrogen or lower alkyl as defined herein The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. One or more non-adjacent carbon atoms may optionally be replaced by oxygen, sulfur, substituted or unsubstituted nitrogen atom(s). Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, octyl and 2-methoxyethyl. The term (ar)alkyl or (heteroaryl)alkyl indicate the alkyl group is optionally substituted by an aryl or a heteroaryl group respectively.

The term "alkenyl" as used herein denotes an unsubstituted hydrocarbon chain radical having from 2 to 10 carbon atoms containing one or two olefinic double bonds. $C_{2-10}$ alkenyl" as used herein refers to an alkenyl composed of 2 to 10 carbons. Examples are vinyl, 1-propenyl, 2-propenyl (allyl) or 2-butenyl (crotyl).

The term "alkynyl" as used herein denotes an unbranched or branched hydrocarbon chain radical having from 2 to 10 carbon atoms [preferably 2 to 4 carbon atoms], and containing one or where possible two triple bonds. $C_{2-10}$ alkynyl" as used herein refers to an alkynyl composed of 2 to 10 carbons Examples are ethynyl, 1-propynyl, 2-propynyl, 1-butynyl, 2-butynyl or 3-butynyl.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkyl-alkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "aryl" as used herein denotes a monovalent aromatic carbocyclic radical containing 5 to 15 carbon atoms consisting of one individual ring, or one or more fused rings in which at least one ring is aromatic in nature, which can optionally be independently substituted with one or more, preferably one or three substituents. Examples of suitable substituents include, but are not limited to, hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Thus a bicyclic aryl substituents may be fused to a heterocyclyl or heteroaryl ring; however, the point of attachment of bicyclic aryl substituent is on the carbocyclic aromatic ring. Examples of aryl radicals include, but are not limited to, phenyl, naphthyl, indanyl, anthraquinolyl tetrahydronaphthyl, 3,4-methylenedioxyphenyl, 1,2,3,4-tetrahydroquinolin-7-yl, 1,2,3,4-tetrahydroisoquinoline-7-yl.

The term "aryl-alkyl" or "aralkyl" as used herein denotes the radical R'R", wherein R' is an aryl radical as defined herein, and R" is an alkylene radical as defined herein with the understanding that the attachment point of the arylalkyl moiety will be on the alkylene radical. The term "aryl-$C_{1-6}$ alkyl" refers a radical R'R" wherein R' is an aryl radical and R" is an alkylene chain containing 1 to 6 carbon atoms. The term "phenyl $C_{1-6}$ alkyl" refers to a radical R'R" wherein R' is a phenyl group and R" is an alkylene chain containing 1 to 6 carbon atoms. Examples of arylalkyl radicals include, but are not limited to, benzyl, phenylethyl, 3-phenylpropyl.

The term "aryloxy" as used herein denotes an O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "aryl-alkoxy" as used herein denotes a alkoxy group as defined herein wherein a hydrogen atom is replaced by an aryl is as defined above. An arylethoxy group is a 2-phenylethoxy or a 1-phenylalkoxy wherein the aryl ring is unsubstituted or substituted with one or two suitable substituents. The term "benzyloxy" refers to a phenylmethoxy group.

The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^1$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, alkylamino or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl. A hydroxyalkyl, aminoalkyl, (di)alkylaminoalkyl or thioalkyl group each represent distinct subsets of the heteroalkyl groups.

The term "heteroalkoxy" as used herein means an —O—(heteroalkyl) group wherein heteroalkyl is defined herein. $C_{1-10}$ heteroalkoxy" as used herein refers to an-O-(heteroalkyl) wherein alkyl is $C_{1-10}$. Representative examples include, but are not limited to, 2-dimethylaminoethoxy and 3-sulfonamido-1-propoxy.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on a heteroaryl ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heteroaryloxy" as used herein means an —O-heteroaryl group, wherein heteroaryl is as defined above such as 3-pyridyloxy and 2-pyrimidinoxy.

The terms "hydroxyalkyl" and "alkoxyalkyl" as used herein denotes an alkyl group as defined herein where 1 to 3 hydrogens are replaced by a hydroxy radical or an alkoxy radical respectively and the attachment point of the hydroxyalkyl radical will be on the alkyl group.

The term "haloalkyl" as used herein denotes a unbranched or branched chain alkyl group as defined above wherein 1, 2, 3 or more hydrogen atoms are substituted by a halogen. "$C_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The term pyrid-2-on-5-yl-methyl, thien-2-yl-methyl and 3-hydroxy-pyrrolidin-1-yl refer to the radicals (i)-(iii) respectively.

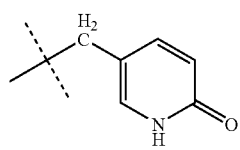

(i)

-continued

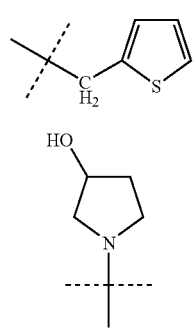

(ii)

(iii)

The term pyridone refers to a 2-hydroxypyridine or a 4-hydroxypyridine both of which have tautomeric structures wherein hydrogen shift results in a C—O double bond and a protonated nitrogen atom in the pyridine ring. The term pyridone refers to both tautomeric forms and both regioisomers.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\leftrightarrows$ —C(—OH)=CH—), amide/imidic acid (—C(=O)—NH— $\leftrightarrows$ —C(—OH)=N—) and amidine (—C(=NR)—NH— $\leftrightarrows$ —C(—NHR)=N—) tautomers. The latter two are particularly common in heteroaryl and heterocyclic rings and the present invention encompasses all tautomeric forms of the compounds.

The term "combination" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes peginterferon-α-2a (PEGASYS®) and peginterferon-α-2b (PEGINTRON®).

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g.), a solvent or water) trapped within.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo [3.3.1]nonane (9-BBN or BBN), methyl (Me), tert-butoxycarbonyl (Boc), acetonitrile (MeCN), di-tert-butyl pyrocarbonate or boc anhydride (BOC$_2$O), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), MeSO$_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo [5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DIPEA), pyridine (pyr), di-iso-butylaluminumhydride, DIBAL-H, room temperature, rt or RT, N,N-dimethyl acetamide (DMA), tert-butyldimethylsilyl or t-BuMe$_2$Si, (TBDMS), 4-N,N-dimethylaminopyridine (DMAP), triethylamine (Et$_3$N or TEA), N,N-dimethylformamide (DMF), triflate or CF$_3$SO$_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$ Si (TMS), ethyl (Et), p-toluenesulfonic acid monohydrate (TsOH or pTsOH), lithium hexamethyl disilazane (LiHMDS), 4-Me-C$_6$H$_4$SO$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol.

1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, column and thin-layer chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in the following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

3-(1,1-Dioxo-1H-1$\lambda^6$-benzo[d]isothiazol-3-yl)-isoquinolin-4-ol compounds 6 were prepared (SCHEME 1) by a boron trichloride-mediated N-dealkylation of the tert-butyl group and concomitant intramolecular cyclization/dehydration of the resulting ortho-sulfonamido ketone 5. Treatment with BCl$_3$ also resulted in concomitant demethylation of the methyl ether on the isoquinoline moiety (SCHEME 1 step 7). Other acidic conditions (e.g., H$_2$SO$_4$/EtOH/80° C.) allowed the deprotection of the sulfonamide and subsequent cyclization of the isothiazole ring without concurrent demethylation of the methyl ether. Metallation of an aryl sulfonamide by an alkyl lithium results in regiospecific ortho-metallation (S. L. MacNeil et al., *J. Org. Chem.* 2001 66(11):3662-3670; V. Snieckus, *Chem Rev.* 1990 90:879-933; V. Snieckus, *Org. React.* 1979 26:1-360; H. Watanabe et al., *J. Org. Chem.* 1968 33:900-903) of the phenyl ring and subsequent acylation with the Weinreb amide 4b to afford the intermediate 5 (S. Nahm and S. M. Weinreb *Tetrahedron Lett.* 1981 22:3815; *Org Prep. Proc. Intl.* 1993 25:15).

SCHEME 1

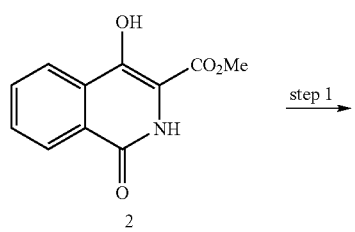

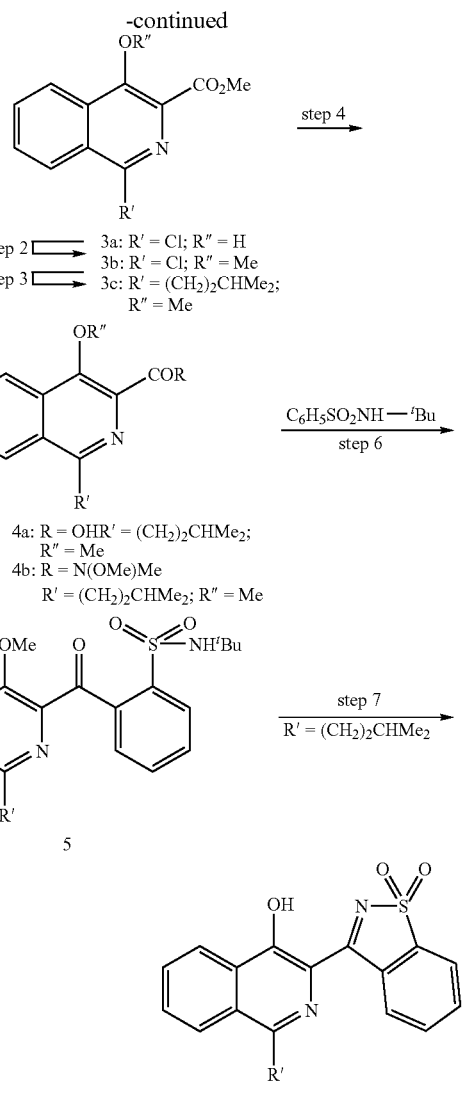

The requisite alkyl-(1-(ar)alkyl)-4-methoxyisoquinoline-3-carboxylate intermediates can be prepared from an appropriately substituted 4-hydroxy-3-carbomethoxy-1(2H)-isoquinolone (2). The isoquinolones can be prepared by the Gabriel-Colman rearrangement of phthalimidoacetic acids (Gabriel and Colman, *Chem Ber.* 1902 35:2421; L. R. Caswell and P. C. Atkinson; *J. Heterocyclic Chem.* 1966 3:328-332; W. Gensler, *Isoquinoline in Heterocyclic Compounds*, R. C. Elderfield, ed. John Wiley & Sons, NY 1952, pp. 376-379). Chlorination of the 1-oxo-1,2-dihydro-isoquinoline moiety to afford 3a is readily accomplished with POCl$_3$ or PCl$_5$. The phenol is protected as an alkyl ether 3b which is readily introduced by exposing the phenol to an alkylating agent in the presence of a base capable of deprotonating the phenol. Alkyl halides, dialkyl sulfates and sulfonate esters of alcohols are commonly used alkylating agents while alkali metal salts, e.g., K$_2$CO$_3$, Na$_2$CO$_3$ or Cs$_2$CO$_3$, alkali metal alkoxides or hydrides are convenient bases. Numerous alternative protecting groups and protocols for alkylation and dealkylation are known in the art and can be employed to prepare compounds of the present invention.

Reagents and protocols for deprotection are described in T. W. Greene and P. G. M. Wuts, *Protective Groups in Organic Synthesis*, Wiley & Sons, New York 1999.

Introduction of an alkyl, optionally substituted aralkyl or alkylcycloalkyl group at the 1-position by coupling with 3b can be accomplished utilizing a Negishi coupling of organozinc halides or dialkylzinc. (E.-I. Negishi, *Acc. Chem. Res.* 1982 15:340-348). Facile condensation takes place with haloarenes and aryl triflates. The reaction is catalyzed by palladium Pd(0) and palladium is preferably ligated to a bidentate ligand including Pd(dppf)Cl$_2$ and Pd(dppe)Cl$_2$. (J. M. Herbert *Tetrahedron Lett.* 2004 45:817-819). Typically the reaction is run an inert aprotic solvent and common ethereal solvents include dioxane, DME and THF are suitable. The reaction can be run at elevated temperature.

Compounds of the present invention can have an amine substituent at the 1-position. Introduction of primary or secondary amines by replacement of a leaving group on a (hetero)aryl ring can be accomplished by Buchwald-Hartwig palladium-catalyzed cross-coupling of an amine and 3b (J. P. Wolfe and S. L. Buchwald, *J. Org. Chem* 2000 65:1144-1157; J. P. Wolfe et al., *J. Org. Chem* 2000 65:1158; J. F. Hartwig, *Angew. Chem. Int. Ed.* 1998 37:2046-2067). Typical conditions include Pd(dppf)Cl$_2$ in the presence of base, e.g. sodium tert-butoxide, and an aprotic solvent. Typical leaving groups include halogen and triflates and optimum leaving groups will depend on the precise reactant.

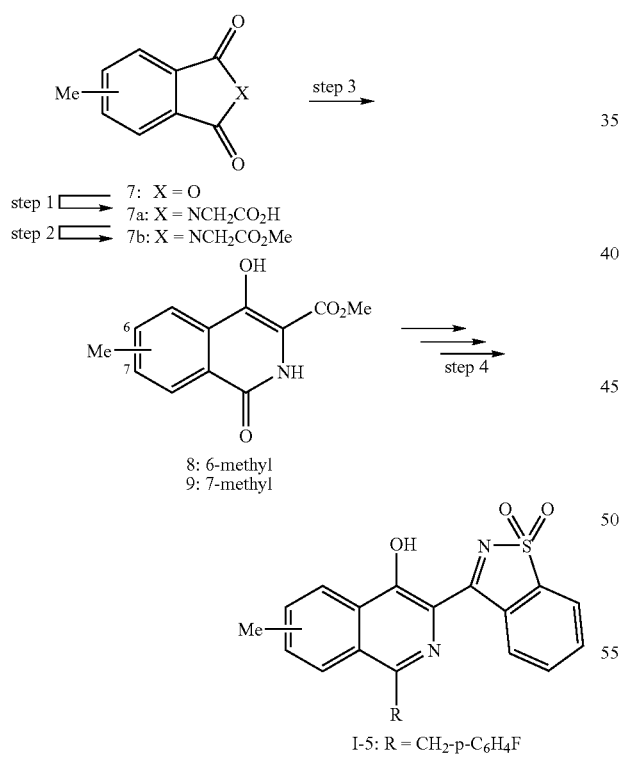

The present invention includes compounds with substitution on the 4-hydroxy-3-carbomethoxy-1(2H)-isoquinolone ring. Regioisomeric mixtures of substituted 3-carbomethoxy-4-hydroxy-1(2H)-isoquinolone can be prepared by the Gabriel-Colman rearrangement of substituted 5-methyl-phthalimidoacetic acids. SCHEME 2 illustrates the preparation of a mixture of 3-carbomethoxy-4-hydroxy-6-methyl-1(2H)-isoquinolone and 3-carbomethoxy-4-hydroxy-7-methyl-1(2H)-isoquinolone. The intermediate isomeric chloro-methoxy isoquinolines were separated by SiO$_2$ chromatography or fractional crystallization.

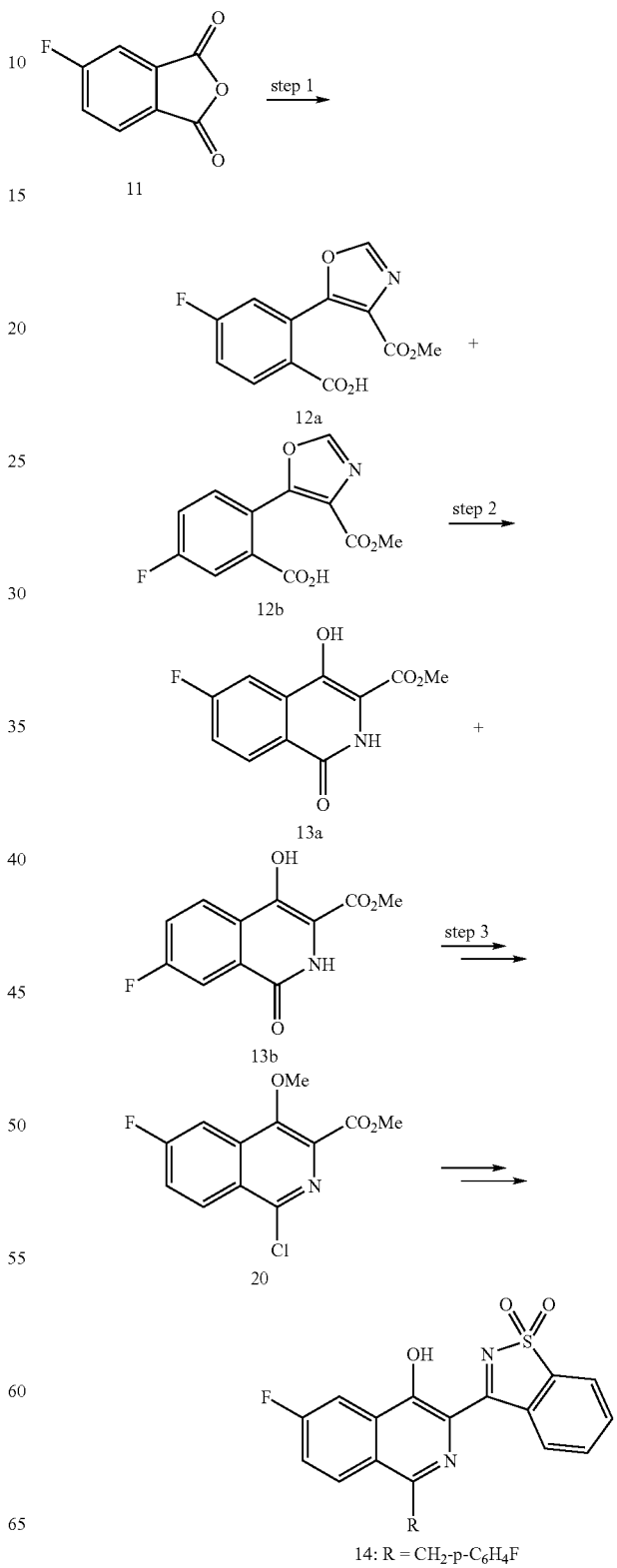

3-Carbomethoxy-6-fluoro-4-hydroxy-1(2H)-isoquinolone (13a) was prepared condensation of isocyano-acetic acid methyl ester and 5-fluorophthalic anhydride (11) to afford a regioisomeric mixture of oxazoles 12a and 12b. Acid-catalyzed unraveling of the oxazole and cyclization of the nascent amine ketone generated by the ring opening affords a regioisomeric mixture of isoquinolones 13a and 13b which could be separated and converted to 14 utilizing standard conditions described herein.

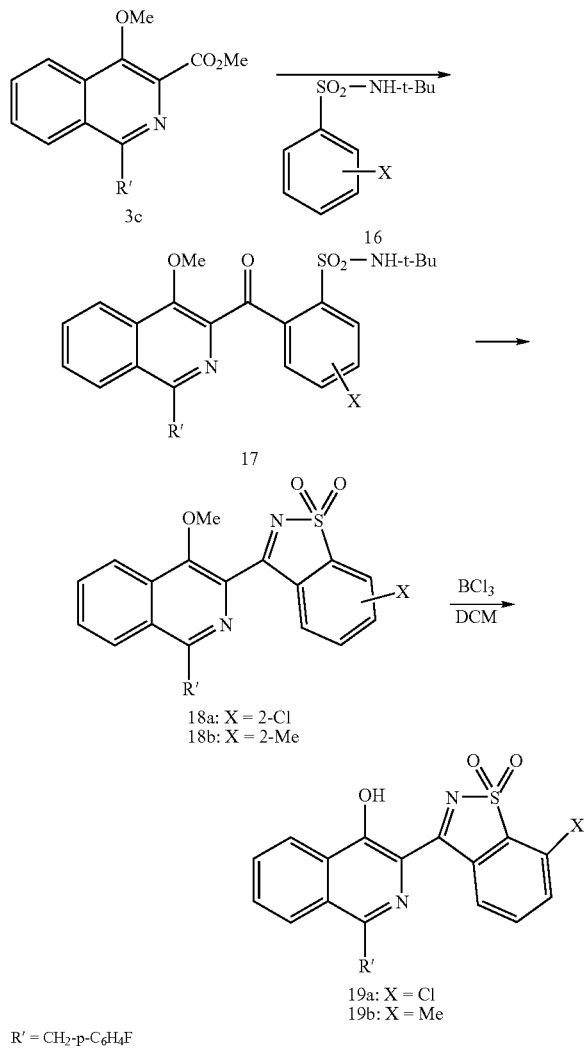

SCHEME 4

18a: X = 2-Cl
18b: X = 2-Me

19a: X = Cl
19b: X = Me

R' = CH$_2$-p-C$_6$H$_4$F

Substitution on the 1,1-dioxo-1H-1λ$^6$-benzo[d]isothiazol-3-yl moiety can be introduced by utilizing a substituted N-tert-butyl phenylsulfonamide 16 which underwent condensation and cyclization in analogous manner. 3-(7-Chloro-1,1-dioxo-1H-1λ$^6$-benzo[d]isothiazol-3-yl)-1-(4-fluorobenzyl)-isoquinolin-4-ol (19a) is also a useful synthetic intermediate for further elaboration of aryl substituents through palladium-catalyzed cross coupling reactions. Methyl groups can be introduced by palladium catalyzed coupling of 19a and methylboronic acid. Other alkyl substituents could be introduced in analogous manner. Phenyl substituents (19:X=optionally substituted phenyl) can be introduced by utilizing optionally substituted phenylboronic acid compounds. A. F. Littke et al., *J. Am. Chem. Soc.* 2000 122: 4020-4028 disclose conditions for biaryl synthesis by Suzuki cross-coupling with arylboronic acids in high yield at RT utilizing Pd$_2$(dba)$_3$/P(tert-bu)$_3$ and conditions for cross-coupling of aryl- and vinyl triflates utilizing Pd(OAc)$_2$/P(C$_6$H$_{11}$)$_3$ at RT. J. P. Wolf et al., *J. Am. Chem. Soc.* 1999 121:9550-9561 similarly disclose efficient condition for Suzuki cross-coupling of aryl rings utilizing Pd(OAc)2/o-(di-tert-butylphosphino)biphenyl or o-(dicyclohexylyphosphino)biphenyl.

Heterocyclic substituents were introduced at the 7-position by Suzuki coupling of the 7-chloro compound and a heteroaryl boronic acid derivative or by Stille coupling of heteroaryl tributyl tin derivatives. 4-Methoxy-3-pyridylboronic acid, 3-[1,3,2]dioxaborinan-2-yl-pyridine, 4-(4,4,5,5-tetramethyl-[1,3,2]dioxaborolan-2-yl)-pyrazole-1-carboxylic acid tert-butyl ester and 5-(4,4,5,5-tetramethyl-[1,3,2]dioxaborolan-2-yl)-pyrimidine were coupled utilizing a Suzuki protocol.

2-Methoxy-6-trimethylstannanyl-pyridine was coupled with the 19a utilizing the Stille protocol. The Stille cross-coupling reaction is a palladium-catalyzed coupling of an aryl or vinyl stannanes with aryl or vinyl halides or -sulfonyloxy compounds (J. K. Stille, *Angew. Chem. Int. Ed.* 1986 25:508-524; A. F. Littke and G. C. Fu, *Angew. Chem. Int. Ed.* 1999, 38:2411-2413). Commercially available Pd reagents including Pd(PPh$_3$)$_4$, Pd(OAc)$_2$ and Pd$_2$(dba)$_3$ can be used. Phosphine ligands are useful rate accelerants if they are not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al., *J. Org. Chem.* 1994 59:5905-5911). The reaction is typically run in aprotic solvents at elevated temperature. Demethylation of the 2-methoxy group with pyridinium hydrochloride afforded the corresponding pyridine I-26.

Examples of representative 3-(1,1-dioxo-1H-1λ$^6$-benzo[d]isothiazol-3-yl)-isoquinolin-4-ol compounds encompassed by the present invention and within the scope of the invention are provided in TABLE 1. These examples and preparations included in the accompanying tables and examples are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beulstein Institute computerized system for the generation of FUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system for these ring systems are as follows:

TABLE 1

| Cpd. No. | NAME | mp | ms | mw |
|---|---|---|---|---|
| I-1 | 3-(1,1-Dioxo-1H-1$\lambda^6$-benzo[d]isothiazol-3-yl)-1-(3-methyl-butyl)-isoquinolin-4-ol | 206-209 | 381 | 380.47 |
| I-2 | 3-(1,1-Dioxo-1H-1$\lambda^6$-benzo[d]isothiazol-3-yl)-1-(4-fluoro-benzyl)-isoquinolin-4-ol | 245-250 | 419 | 418.45 |
| I-3 | 1-(2-Cyclopropyl-ethyl)-3-(1,1-dioxo-1H-1$\lambda^6$-benzo[d]isothiazol-3-yl)-isoquinolin-4-ol | 189-191 | 379 | 378.45 |
| I-4 | 3-(1,1-Dioxo-1H-1$\lambda^6$-benzo[d]isothiazol-3-yl)-6-fluoro-1-(4-fluoro-benzyl)-isoquinolin-4-ol | >275 | 437.2 | 436.44 |
| I-5 | 3-(1,1-Dioxo-1H-1$\lambda^6$-benzo[d]isothiazol-3-yl)-1-(4-fluoro-benzyl)-6-methyl-isoquinolin-4-ol | >275 | 433 | 432.47 |
| I-6 | 3-(7-Chloro-1,1-dioxo-1H-1$\lambda^6$-benzo[d]isothiazol-3-yl)-1-(4-fluoro-benzyl)-isoquinolin-4-ol | | 451.3 | 452.89 |
| I-7 | 3-(1,1-Dioxo-1H-1$\lambda^6$-benzo[d]isothiazol-3-yl)-1-[(4-fluoro-phenyl)-methyl-amino]-isoquinolin-4-ol | 215-217 | 433 | 433.46 |
| I-8 | 1-(Cyclopropylmethyl-amino)-3-(1,1-dioxo-1H-1$\lambda^6$-benzo[d]isothiazol-3-yl)-isoquinolin-4-ol | 270-272 | 380 | 379.44 |
| I-9 | 1-(4-Fluoro-benzyl)-3-(7-methyl-1,1-dioxo-1H-1$\lambda^6$-benzo[d]isothiazol-3-yl)-isoquinolin-4-ol | | 433.2 | 432.47 |
| I-10 | 1-(4-Fluoro-benzyl)-3-(7-methoxy-1,1-dioxo-1H-1$\lambda^6$-benzo[d]isothiazol-3-yl)-isoquinolin-4-ol | | 449.2 | 448.47 |
| I-11 | 1-(4-Fluoro-benzyl)-3-(7-morpholin-4-yl-1,1-dioxo-1H-1$\lambda^6$-benzo[d]isothiazol-3-yl)-isoquinolin-4-ol | 259-261 | 504 | 503.55 |
| I-12 | 3-(1,1-Dioxo-7-phenyl-1H-1$\lambda^6$-benzo[d]isothiazol-3-yl)-1-(4-fluoro-benzyl)-isoquinolin-4-ol | >275 | 495.2 | 494.54 |
| I-13 | 1-(4-Fluoro-benzyl)-3-[7-(3-hydroxy-phenyl)-1,1-dioxo-1H-1$\lambda^6$-benzo[d]isothiazol-3-yl]-isoquinolin-4-ol | >275 | 511 | 510.54 |
| I-14 | 1-(4-Fluoro-benzyl)-3-[7-(4-fluoro-phenyl)-1,1-dioxo-1H-1$\lambda^6$-benzo[d]isothiazol-3-yl]-isoquinolin-4-ol | >275 | 513 | 512.53 |
| I-15 | 3-(1,1-Dioxo-7-m-tolyl-1H-1$\lambda^6$-benzo[d]isothiazol-3-yl)-1-(4-fluoro-benzyl)-isoquinolin-4-ol | 228-230 | 509 | 508.57 |
| I-16 | N-(3-{3-[1-(4-Fluoro-benzyl)-4-hydroxy-isoquinolin-3-yl]-1,1-dioxo-1H-1$\lambda^6$-benzo[d]isothiazol-7-yl}-phenyl)-acetamide | >275 | 552 | 551.6 |
| I-17 | 1-(4-Fluoro-benzyl)-3-[7-(3-fluoro-phenyl)-1,1-dioxo-1H-1$\lambda^6$-benzo[d]isothiazol-3-yl]-isoquinolin-4-ol | >275 | 513 | 512.53 |
| I-18 | N-(3-{3-[1-(4-Fluoro-benzyl)-4-hydroxy-isoquinolin-3-yl]-1,1-dioxo-1H-1$\lambda^6$-benzo[d]isothiazol-7-yl}-phenyl)-methanesulfonamide | >275 | 588 | 587.65 |
| I-19 | 3-(1,1-Dioxo-7-pyridin-3-yl-1H-1$\lambda^6$-benzo[d]isothiazol-3-yl)-1-(4-fluoro-benzyl)-isoquinolin-4-ol | >275 | 496 | 495.53 |
| I-20 | 3-(7-Chloro-1,1-dioxo-1H-1$\lambda^6$-benzo[d]isothiazol-3-yl)-6-fluoro-1-(4-fluoro-benzyl)-isoquinolin-4-ol | >275 | 469 | 470.88 |
| I-21 | N-{3-[1-(4-Fluoro-benzyl)-4-hydroxy-isoquinolin-3-yl]-1,1-dioxo-1H-1$\lambda^6$-benzo[d]isothiazol-7-yl}-methanesulfonamide | >275 | 512 | 511.55 |
| I-22 | 3-[1,1-Dioxo-7-(1H-pyrazol-4-yl)-1H-1$\lambda^6$-benzo[d]isothiazol-3-yl]-1-(4-fluoro-benzyl)-isoquinolin-4-ol | | 485 | 484.51 |
| I-23 | 1-(4-Fluoro-benzyl)-3-[7-(6-methoxy-pyridin-3-yl)-1,1-dioxo-1H-1$\lambda^6$-benzo[d]isothiazol-3-yl]-isoquinolin-4-ol | 194-196 | 526 | 525.56 |
| I-24 | 3-(1,1-Dioxo-7-pyrimidin-5-yl-1H-1$\lambda^6$-benzo[d]isothiazol-3-yl)-1-(4-fluoro-benzyl)-isoquinolin-4-ol | 230-235 | 497 | 496.52 |
| I-25 | 5-{3-[1-(4-Fluoro-benzyl)-4-hydroxy-isoquinolin-3-yl]-1,1-dioxo-1H-1$\lambda^6$-benzo[d]isothiazol-7-yl}-1H-pyridin-2-one | >275 | 512 | 511.53 |
| I-26 | N-{3-[1-(4-Fluoro-benzyl)-4-hydroxy-isoquinolin-3-yl]-1,1-dioxo-1H-1$\lambda^6$-benzo[d]isothiazol-6-yl}-methanesulfonamide | >275 | 512 | 511.55 |
| I-27 | 6-{3-[1-(4-Fluoro-benzyl)-4-hydroxy-isoquinolin-3-yl]-1,1-dioxo-1H-1$\lambda^6$-benzo[d]isothiazol-7-yl}-1H-pyridin-2-one | | 512 | 511.53 |
| I-28 | 3-(7-Chloro-1,1-dioxo-1H-1$\lambda^6$-benzo[d]isothiazol-3-yl)-1-(4-fluoro-benzyl)-4-methoxy-isoquinoline | | 467 | 466.92 |

The key step in the synthesis of 1-alkyl-5-tert-butyl-3-(1,1-dioxo-1H-1λ⁶-benzo[d]isothiazol-3-yl)-4-hydroxy-1,5-dihydro-pyrrol-2-ones (27) is a condensation of a conjugate base of a 1-substituted (S)-5-tert-butyl-4-hydroxy-1,5-dihydro-pyrrol-2-one (23) produced by deprotonation of 23 and 3-chloro-benzo[d]isothiazole 1,1-dioxide (26). The pyrrol-2-one 23 is an acidic 1,3-dicarbonyl compound which is readily deprotonated under mild conditions. Heteroaryl halides such as 26 can be prepared by treating 1,1-dioxo-1,2-dihydro-1λ⁶-benzo[d]isothiazol-3-one (25) with thionyl chloride or other chlorinating agents. These halides are known to undergo facile nucleophilic addition and subsequent elimination of the chloride substituents. This convergent synthesis is flexible and allows a variety of substitution on the aryl ring of 26 and the 1- and 5-positions of 23.

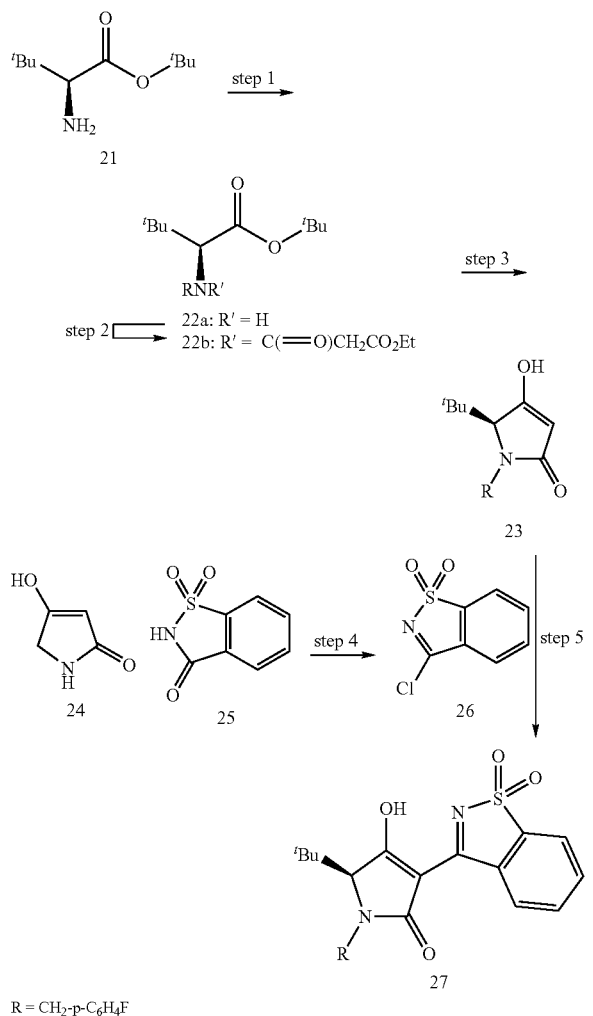

R = CH₂-p-C₆H₄F

The requisite 4-hydroxy-1,5-dihydro-pyrrol-2-ones 23 required for the synthesis of compounds in TABLE 2 are prepared by base-catalyzed intra-molecular cyclization of N-ethoxycarbonylmethyl-malonamic acid ethyl ester. Treatment of amino acid esters (22a) with chlorocarbonyl-acetic acid esters followed by a base-catalyzed Dieckman condensation provides the desired intermediate tetramic acids 23 (see e.g., T. P. C. Mulholland et al., *J. Chem. Soc. Perkin I* 1972 2121, K. Kochhar et al., *Tetrahedron Lett.* 1984 25:1871). The sequence also has been adapted to the solid phase synthesis of tetramic acids (J. Matthews and R. A. Rivero, *J. Org. Chem.* 1998 63(14):4808-4810). Although the accompanying SCHEMES have depicted the preparation of compounds in which a tert-Bu is the C-5 substituent and a p-fluorobenzyl is the N-1 substituent, 4-hydroxy-1,5-dihydro-pyrrol-2-ones with a wide range of substituents at the 1- and 5-positions can be prepared and utilized in similar manner by replacing the aldehyde used in the reductive amination and the amino acid used in the cyclocondensation. The substitution at the 5-position is derived from the amino acid side chain and natural amino acids are commercially available and numerous methods are known for the asymmetric synthesis of natural and unnatural α-amino acids with one or two substituents on the α-carbon. R. M. Williams, *Synthesis of optically active α-amino acids*, Pergamon Press, New York 1999; G. M. Coppola, *Asymmetric synthesis: construction of chiral molecules using amino acids*, Wiley, New York 1987)

The 1-substituent of the requisite 4-hydroxy-1,5-dihydro-pyrrol-2-ones (23) is introduced by reductive amination of an aldehydes or ketone and an α-amino acid. Reductive amination is preferably carried out by combining the amino acid ester and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 optionally in the presence of a dehydrating agent such as molecular sieve or Ti(IV)(O-i-Pr)₄ to facilitate formation of the intermediate imine at ambient temperature or with hydrogen in the presence of a hydrogenation catalyst, e.g. in the presence of palladium/charcoal, at a hydrogen pressure of 1 to 5 bar, preferably at temperatures between 20° C. and the boiling temperature of the solvent used. Reductive amination procedures have been reviewed: R. M. Hutchings and M. K. Hutchings, Reduction of C═N to CHNH by Metal Hydrides in *Comprehensive Organic Synthesis*, col. 8, I. Fleming (Ed), Pergamon, Oxford 1991 pp. 47-54.

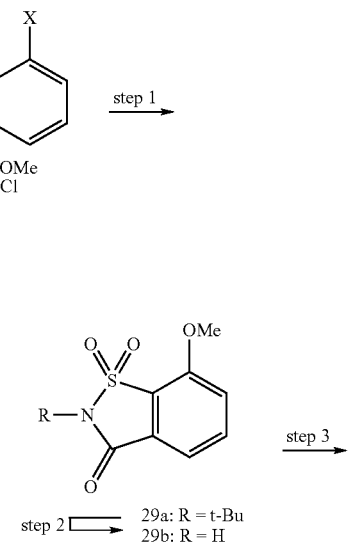

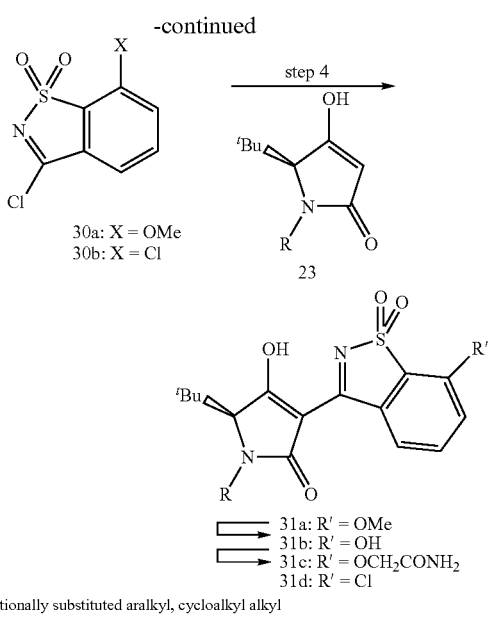

30a: X = OMe
30b: X = Cl

31a: R' = OMe
31b: R' = OH
31c: R' = OCH$_2$CONH$_2$
31d: R' = Cl

R = alkyl, optionally substituted aralkyl, cycloalkyl alkyl

Aryl substituted 3-chloro-benzo[d]isothiazole-1,1-dioxides can be employed in the coupling step to prepare 3-(1,1-dioxo-1H-1λ$^6$-benzo[d]isothiazol-3-yl)-4-hydroxy-1,5-dihydro-pyrrol-2-ones with aryl substitution on the benzo[d] isothiazole fragment of the molecule and such compounds are inhibitors of HCV polymerase as well as useful intermediates to further introduce other aryl substituents. Aryl substituted 3-chloro-benzo[d]isothiazole 1,1-dioxides 30 can be prepared by ortho-metallation of a substituted N-tert-butyl-benzenesulfonamide 28, quenching the resulting aryl lithium intermediate with iso-butylchloroformate to introduce a formyl radical and cyclizing the resulting carbonyl compound (see, e.g., step 1 of example 15). N-tert-butyl-2-methoxy-benzenesulfonamide (28a) affords the 2-tert-butyl-7-methoxy-1-oxo-1,2-dihydro-1λ$^4$-benzo[d]isothiazol-3-one (29a). The metallation of N-tert-butyl-benzenesulfonamides is conveniently carried out with an alkyl or aryl lithium compound or with a lithium dialkylamide base in an inert solvent at temperatures between 0° C. and −78° C. Commonly used solvents include THF, DME, ether and dioxane, however other solvents which are not reactive with the organolithium compounds also can be used. The carbonylating agent is generally added at low temperature and the warmed to RT. Facile intramolecular cyclization affords a 2-tert-butyl-1-oxo-1,2-dihydro-1λ$^4$-benzo[d]isothiazol-3-one. The tert-butyl group is removed by acid or Lewis acid catalysts and chlorination affords the requisite 3-chloro-benzo[d]isothiazole 1,1-dioxide 30 Condensation of 30a and 23 affords 7-methoxy derivative 31a. Dealkylation of 31a with AlCl$_3$ affords the hydroxyl derivative 31b which is an inhibitor of HCV polymerase as well as useful intermediate which can be alkylated to introduce additional substituents which can enhance the potency and optimize the physical properties of the compounds. 2-tert-butyl-7-chloro-1-oxo-1,2-dihydro-1λ$^4$-benzo[d]isothiazol-3-one (30b) was prepared from N-tert-butyl-2-chloro-benzenesulfonamide (28b) and further converted to 31d in analogous manner.

(S)-5-tert-Butyl-3-(7-chloro-1,1-dioxo-1H-1λ$^6$-benzo[d] isothiazol-3-yl)-1-(4-fluoro-benzyl)-4-hydroxy-1,5-dihydro-pyrrol-2-one (31d) can be utilized as a synthetic intermediate to introduce other substitution into 7-position. The Suzuki and Stille reactions were utilized for coupling procedures to replace the 7-chloro substituent with aryl and heteroaryl substitutents. The 7-methyl substitutent was introduced by a Suzuki coupling of 31d and methyl boronic acid. The coupling could be carried out either on 2-tert-butyl-7-chloro-1,1-dioxo-1,2-dihydro-1λ$^6$-benzo[d]isothiazol-3-one (30b) prior to condensation with 23 or on the fully elaborated (S)-5-tert-butyl-3-(7-chloro-1,1-dioxo-1H-1λ$^6$-benzo[d] isothiazol-3-yl)-1-(4-fluoro-benzyl)-4-hydroxy-1,5-dihydro-pyrrol-2-one (II-4).

The Suzuki reaction (N. Miyama and A. Suzuki, Chem. Rev. 1995 95:2457-2483; A. Suzuki, J. Organomet. Chem. 1999 576:147-168), Heck reaction (W. Cabri and I. Candiani, Acc. Chem. Res. 1995 28:2-7; A. Meijere and F. E. Meyer, Angew. Chem. Int. Ed. Eng. 1994 33:2379-2411) and Stille reaction (V. Farina et al., Org. React. 1998 50:1-652; J. K. Stille, Angew. Chem. Int. Ed. Eng. 1986 25:508-524) represent a general class of palladium-catalyzed coupling reaction with aryl or vinyl halides and triflates. The Suzuki reaction is a palladium-catalyzed coupling of a boronic acid (R=aryl, vinyl or alkyl) with an aryl or vinyl halide or triflate (R$^1$=aryl or vinyl, Y=halide or —OSO$_2$CF$_3$). The reactions are mechanistically related and are believed to proceed through an oxidative-addition mechanism. Pd(II) compounds used as catalyst are believed to be reduced to the catalytically active Pd(0) species in situ. Typical catalysts include

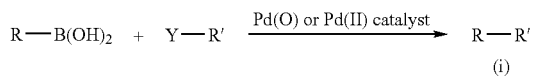

(i)

Pd(PPh$_3$)$_3$, Pd(OAc)$_2$ and PdCl$_2$(dppf). With PdCl$_2$(dppf), primary alkyl borane compounds can be coupled to aryl or vinyl halide or triflate without β-elimination. The reaction can be carried out in a variety of organic solvents including toluene, THF, dioxane, 1,2-dichloroethane, DMF, DMSO and acetonitrile, aqueous solvents and under biphasic conditions. Reactions are typically run from about room temperature to about 150° C. Additives (e.g. CsF, KF, TlOH, NaOEt and KOH) frequently accelerate the coupling. Although there are numerous components in the Suzuki reaction including the palladium source, the ligand, additive solvent, temperature, etc., numerous protocols have been identified. Highly active catalysts have been identified (see, e.g. J. P. Wolfe et al., J. Am. Chem. Soc. 1999 121(41):9550-9561 and A. F. Littke et al, J. Am. Chem. Soc. 2000 122(17):4020-4028). One skilled in the art will be able to identify a satisfactory protocol without undue experimentation.

There are a large number of parameters in the Suzuki reaction including the palladium source, ligand, additives and temperature and optimum conditions sometimes require optimization of the parameters for a given pair of reactants. One skilled in the art can determine optimal conditions without undue experimentation. Recently useful general conditions have been disclosed. A. F. Littke et al. J. Am. Chem. Soc. 2000 122:4020-4028 disclose conditions for Suzuki cross-coupling with arylboronic acids in high yield at RT utilizing Pd$_2$(dba)$_3$/P(tert-bu)$_3$ and conditions for cross-coupling of aryl- and vinyl triflates utilizing Pd(OAc)$_2$/P(C$_6$H$_{11}$)$_3$ at RT. J. P. Wolf et al. J. Am. Chem. Soc. 1999 121:9550-9561 disclose efficient condition for Suzuki cross-coupling utilizing Pd(OAc)2/o-(di-tert-butylphosphino)biphenyl or o-(dicyclohexylyphosphino)biphenyl The Stille cross-coupling reaction is a palladium-catalyzed coupling of an aryl or vinyl stannanes with aryl or vinyl halides or -sulfonyloxy compounds (J. K. Stille *Angew. Chem. Int. Ed.* 1986 25:508-524; A. F. Littke and G. C. Fu *Angew. Chem. Int. Ed.* 1999, 38:2411-2413). Commercially available Pd reagents including Pd(PPh$_3$)$_4$, Pd(OAc)$_2$ and Pd$_2$(dba)$_3$ can be used. Phosphine ligands are useful rate accelerants if they ar not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al. *J. Org. Chem.* 1994 59:5905-5911). The reaction is typically run in aprotic solvents at elevated temperature.

An amino moiety was introduced utilizing a Buchwald-Hartwig palladium-catalyzed cross-coupling of II-4 and carbamic acid tert-butyl ester (supra). SCHEME 7 illustrates the use of

SCHEME 7

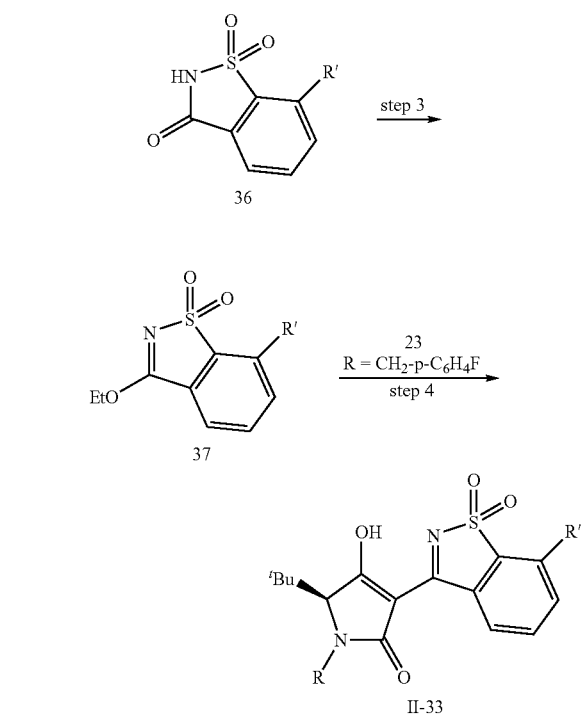

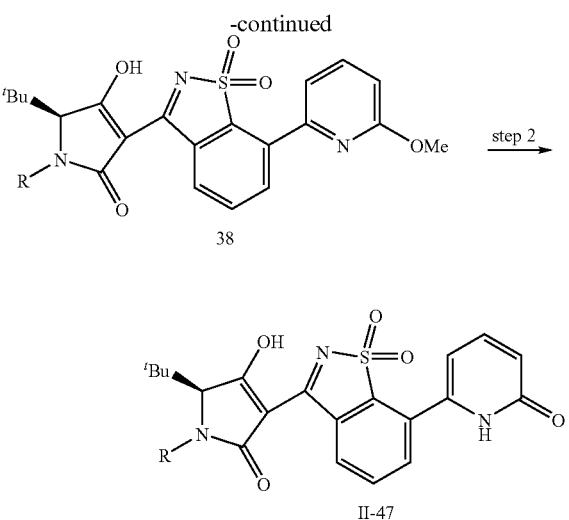

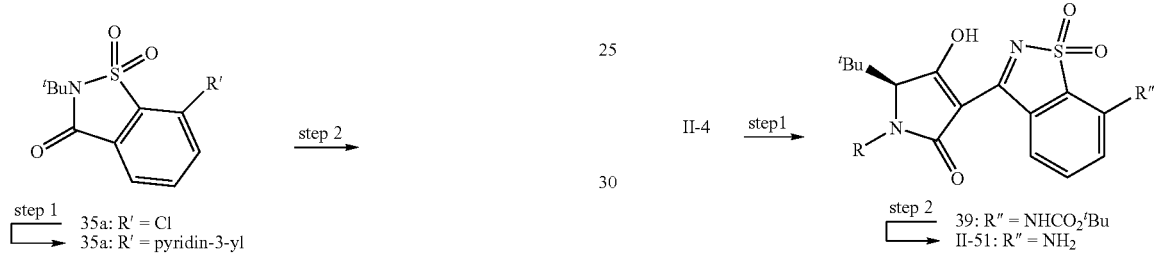

palladium-catalyzed couplings to prepare compounds of the present invention. The coupling of pyridin-3-yl boronic acid and 2-tert-butyl-7-chloro-benzo[d]isothiazol-3-one (35a) exemplifies the use of a Suzuki reaction to introduce a heteroaryl moiety onto the benzo[d]isothizole which is further reacted with 23 to introduce the pyrrolone ring and afford II-32 (Example 15). In contrast 38 was prepared by a Stille coupling with 2-tributylstannyl-6-methoxy pyridine carried out in the final step of the synthesis. The methyl ether was cleaved by contacting 38 with AlCl$_3$ to afford II-47 (Example 18). The Buchwald/Hartwig protocol was used to catalyze the condensation of tert-butyl carbamate and II-4 to afford 39 which was deprotected under standard conditions to afford II-51 (Example 20). Acylation and sulfonylation of II-51 affords amides and sulfonamides.

7-Aminoalkyl compounds of the present invention were prepared by displacement of (S)-5-tert-butyl-3-(7-chloromethyl-1,1-dioxo-1H-1λ$^6$-benzo[d]isothiazol-3-yl)-1-(4-fluoro-benzyl)-4-hydroxy-1,5-dihydro-pyrrol-2-one (43) with amine nucleophiles. The chloromethyl radical was prepared by allylic bromination of 40b which was prepared by Suzuki coupling of methylboronic acid and 40a. Chlorination of the dioxo-1,2-dihydro-isothiazol-3-one ring 41 resulted in the concomitant conversion of the bromomethyl to a chloromethyl radical. The conversion of 42 to 43 proceeded as previously described and the resulting chloromethyl compound was converted to II-38 by displacement with the sodium salt of methanesulfonamide. Other sulfonamides and amides were accessible from the corresponding sulfonamide or carboxyamide or by acylation of the corresponding amine.

SCHEME 8

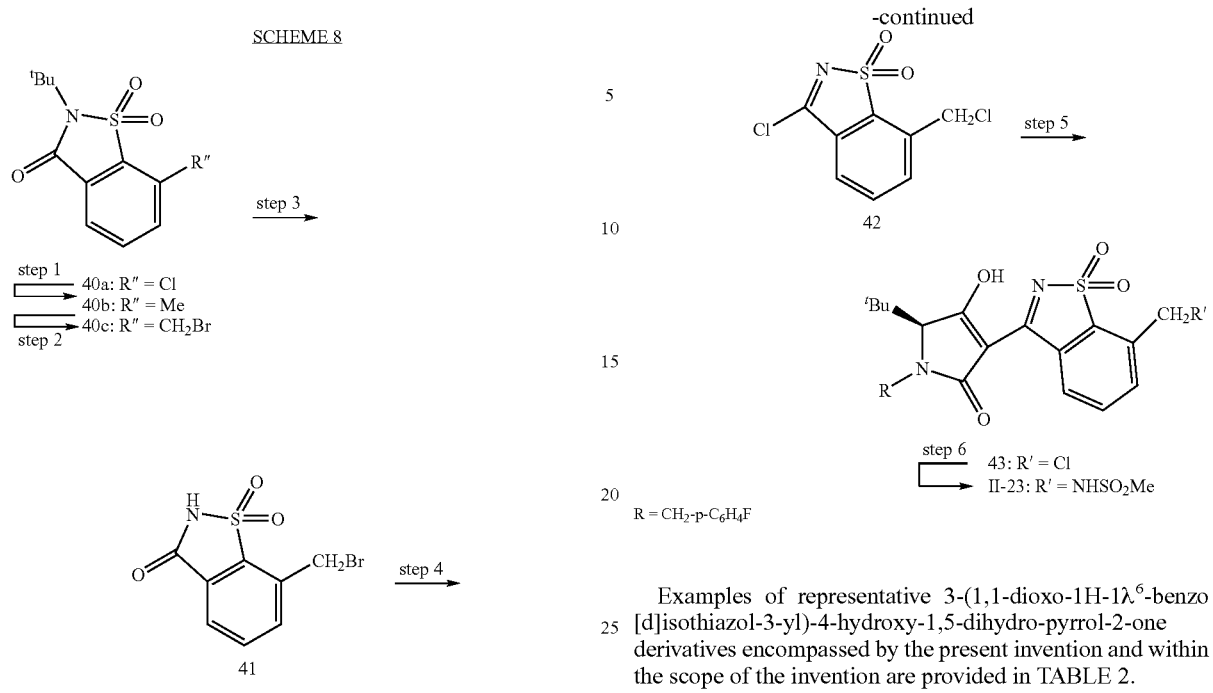

R = CH$_2$-p-C$_6$H$_4$F

Examples of representative 3-(1,1-dioxo-1H-1λ$^6$-benzo[d]isothiazol-3-yl)-4-hydroxy-1,5-dihydro-pyrrol-2-one derivatives encompassed by the present invention and within the scope of the invention are provided in TABLE 2.

TABLE 2

| Cpd. No. | NAME | mp | ms | mw |
|---|---|---|---|---|
| II-1 | (S)-1-Benzyl-5-cyclohexyl-3-(1,1-dioxo-1H-1λ$^6$-benzo[d]isothiazol-3-yl)-4-hydroxy-1,5-dihydro-pyrrol-2-one | 104-106 | 435 | 436.53 |
| II-2 | (S)-1-Benzyl-5-tert-butyl-3-(1,1-dioxo-1H-1λ$^6$-benzo[d]isothiazol-3-yl)-4-hydroxy-1,5-dihydro-pyrrol-2-one | 170-179 | 409 | 410.49 |
| II-3 | 5-tert-Butyl-3-(1,1-dioxo-1H-1λ$^6$-benzo[d]isothiazol-3-yl)-1-(4-fluoro-benzyl)-4-hydroxy-1,5-dihydro-pyrrol-2-one | >220 | 427 | 428.48 |
| II-4 | 5-tert-Butyl-3-(7-chloro-1,1-dioxo-1H-1λ$^6$-benzo[d]isothiazol-3-yl)-1-(4-fluoro-benzyl)-4-hydroxy-1,5-dihydro-pyrrol-2-one | 179-213 | 461 | 462.93 |
| II-5 | (S)-5-tert-Butyl-1-(4-fluoro-benzyl)-4-hydroxy-3-(7-methoxy-1,1-dioxo-1H-1λ$^6$-benzo[d]isothiazol-3-yl)-1,5-dihydro-pyrrol-2-one | 224-235 | 457 | 458.51 |
| II-6 | 5-tert-Butyl-1-(4-fluoro-benzyl)-4-hydroxy-3-(7-hydroxy-1,1-dioxo-1H-1λ$^6$-benzo[d]isothiazol-3-yl)-1,5-dihydro-pyrrol-2-one | >250 | 443 | 444.48 |
| II-7 | (S)-5-tert-Butyl-3-(1,1-dioxo-1H-1λ$^6$-naphtho[2,1-d]isothiazol-3-yl)-1-(4-fluoro-benzyl)-4-hydroxy-1,5-dihydro-pyrrol-2-one | 205 (dec) | 477 | 478.54 |
| II-8 | (S)-3-(7-Chloro-1,1-dioxo-1H-1λ$^6$-benzo[d]isothiazol-3-yl)-1-(4-fluoro-benzyl)-4-hydroxy-5-isobutyl-1,5-dihydro-pyrrol-2-one | | 461 | 462.93 |
| II-9 | (S)-5-tert-Butyl-3-(1,1-dioxo-1H-1λ$^6$-benzo[d]isothiazol-3-yl)-4-hydroxy-1-(4-methyl-benzyl)-1,5-dihydro-pyrrol-2-one | 93-107 | | 424.52 |
| II-10 | (S)-5-tert-Butyl-3-(1,1-dioxo-1H-1λ$^6$-benzo[d]isothiazol-3-yl)-1-(4-fluoro-3-methoxy-benzyl)-4-hydroxy-1,5-dihydro-pyrrol-2-one | 92-104 | 457 | 458.51 |

TABLE 2-continued

| Cpd. No. | NAME | mp | ms | mw |
|---|---|---|---|---|
| II-11 | (S)-5-tert-Butyl-3-(1,1-dioxo-1H-1$\lambda^6$-benzo[d]isothiazol-3-yl)-4-hydroxy-1-thiophen-2-ylmethyl-1,5-dihydro-pyrrol-2-one | 105-123 | 415 | 416.52 |
| II-12 | (S)-5-Cyclohexyl-3-(1,1-dioxo-1H-1$\lambda^6$-benzo[d]isothiazol-3-yl)-1-(4-fluoro-benzyl)-4-hydroxy-1,5-dihydro-pyrrol-2-one; sodium salt | 235-238 | | 454.52 |
| II-13 | (S)-5-tert-Butyl-1-(4-chloro-benzyl)-3-(1,1-dioxo-1H-1$\lambda^6$-benzo[d]isothiazol-3-yl)-4-hydroxy-1,5-dihydro-pyrrol-2-one | | 443.3 | 444.94 |
| II-14 | 4-[(S)-2-tert-Butyl-4-(1,1-dioxo-1H-1$\lambda^6$-benzo[d]isothiazol-3-yl)-3-hydroxy-5-oxo-2,5-dihydro-pyrrol-1-ylmethyl]-benzonitrile | | 434.3 | 435.5 |
| II-15 | (S)-5-tert-Butyl-3-(1,1-dioxo-1H-1$\lambda^6$-benzo[d]isothiazol-3-yl)-1-(4-fluoro-3-methyl-benzyl)-4-hydroxy-1,5-dihydro-pyrrol-2-one | 105-111 | 441.3 | 442.51 |
| II-16 | (S)-5-((S)-sec-Butyl)-3-(1,1-dioxo-1H-1$\lambda^6$-benzo[d]isothiazol-3-yl)-1-(4-fluoro-benzyl)-4-hydroxy-1,5-dihydro-pyrrol-2-one | 155-160 | 427 | 428.48 |
| II-17 | (S)-5-tert-Butyl-1-cyclobutylmethyl-3-(1,1-dioxo-1H-1$\lambda^6$-benzo[d]isothiazol-3-yl)-4-hydroxy-1,5-dihydro-pyrrol-2-one | 69-78 | 387 | 388.49 |
| II-18 | (S)-3-(1,1-Dioxo-1H-1$\lambda^6$-benzo[d]isothiazol-3-yl)-1-(4-fluoro-benzyl)-4-hydroxy-5-isobutyl-1,5-dihydro-pyrrol-2-one | 200 (d) | 427.3 | 428.48 |
| II-19 | 3-(1,1-Dioxo-1H-1$\lambda^6$-benzo[d]isothiazol-3-yl)-1-(4-fluoro-benzyl)-4-hydroxy-5-isobutyl-1,5-dihydro-pyrrol-2-one | 200 (d) | 427 | 428.48 |
| II-20 | (R)-3-(1,1-Dioxo-1H-1$\lambda^6$-benzo[d]isothiazol-3-yl)-1-(4-fluoro-benzyl)-4-hydroxy-5-isobutyl-1,5-dihydro-pyrrol-2-one | 200 (d) | 427 | 428.48 |
| II-21 | (S)-5-tert-Butyl-1-(3,3-dimethyl-butyl)-3-(1,1-dioxo-1H-1$\lambda^6$-benzo[d]isothiazol-3-yl)-4-hydroxy-1,5-dihydro-pyrrol-2-one | 88-93 | 403 | 404.53 |
| II-22 | (S)-1-(3-Bromo-4-fluoro-benzyl)-5-tert-butyl-3-(1,1-dioxo-1H-1$\lambda^6$-benzo[d]isothiazol-3-yl)-4-hydroxy-1,5-dihydro-pyrrol-2-one | 114-119 | 507 | 507.38 |
| II-23 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 105-128 | 534 | 535.61 |
| II-24 | (S)-5-tert-Butyl-1-(3,4-difluoro-benzyl)-3-(1,1-dioxo-1H-1$\lambda^6$-benzo[d]isothiazol-3-yl)-4-hydroxy-1,5-dihydro-pyrrol-2-one | 80-89 | | 446.47 |
| II-25 | 5-[(S)-2-tert-Butyl-4-(1,1-dioxo-1H-1$\lambda^6$-benzo[d]isothiazol-3-yl)-3-hydroxy-5-oxo-2,5-dihydro-pyrrol-1-ylmethyl]-2-fluoro-benzonitrile | 105-112 | 452 | 453.49 |
| II-26 | (S)-5-tert-Butyl-3-(1,1-dioxo-1H-1$\lambda^6$-benzo[d]isothiazol-3-yl)-1-(4-fluoro-3-trifluoromethyl-benzyl)-4-hydroxy-1,5-dihydro-pyrrol-2-one | 85-91 | 495 | 496.48 |
| II-27 | (S)-3-(1,1-Dioxo-1H-1$\lambda^6$-benzo[d]isothiazol-3-yl)-1-(4-fluoro-benzyl)-4-hydroxy-5-phenyl-1,5-dihydro-pyrrol-2-one | 145-155 | 447 | 448.47 |
| II-28 | (S)-5-Benzyl-3-(1,1-dioxo-1H-1$\lambda^6$-benzo[d]isothiazol-3-yl)-1-(4-fluoro-benzyl)-4-hydroxy-1,5-dihydro-pyrrol-2-one | 85-92 | 461 | 462.5 |
| II-29 | 5-[(S)-2-tert-Butyl-4-(1,1-dioxo-1H-1$\lambda^6$-benzo[d]isothiazol-3-yl)-3-hydroxy-5-oxo-2,5-dihydro-pyrrol-1-ylmethyl]-1H-pyridin-2-one | 149-190 (indistinct) | 426.3 | 427.48 |
| II-30 | (S)-5-tert-Butyl-1-(3-cyclopropyl-4-fluoro-benzyl)-3-(1,1-dioxo-1H-1$\lambda^6$-benzo[d]isothiazol-3-yl)-4-hydroxy-1,5-dihydro-pyrrol-2-one | 71-85 | | 468.55 |
| II-31 | (S)-5-tert-Butyl-1-(3-chloro-4-fluoro-benzyl)-3-(1,1-dioxo-1H-1$\lambda^6$-benzo[d]isothiazol-3-yl)-4-hydroxy-1,5-dihydro-pyrrol-2-one | 81-96 | | 462.93 |
| II-32 | (S)-5-tert-Butyl-3-(1,1-dioxo-7-pyridin-3-yl-1H-1$\lambda^6$-benzo[d]isothiazol-3-yl)-1-(4-fluoro-benzyl)-4-hydroxy-1,5-dihydro-pyrrol-2-one | >275 | 504.2 | 505.57 |
| II-33 | (S)-5-tert-Butyl-1-(4-fluoro-benzyl)-4-hydroxy-3-[7-(6-methoxy-pyridin-3-yl)-1,1-dioxo-1H-1$\lambda^6$-benzo[d]isothiazol-3-yl]-1,5-dihydro-pyrrol-2-one | 185-190 | | 535.59 |
| II-34 | 5-{3-[(S)-5-tert-Butyl-1-(4-fluoro-benzyl)-4-hydroxy-2-oxo-2,5-dihydro-1H-pyrrol-3-yl]- | >275 | 520.3 | 521.57 |

TABLE 2-continued

| Cpd. No. | NAME | mp | ms | mw |
|---|---|---|---|---|
| | 1,1-dioxo-1H-1$\lambda^6$-benzo[d]isothiazol-7-yl}-1H-pyridin-2-one | | | |
| II-35 | N-{3-[5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-methanesulfonamide | 115-125 | | 549.64 |
| II-36 | (S)-5-tert-Butyl-1-(4-fluoro-benzyl)-4-hydroxy-3-[7-(2-methoxy-pyrimidin-5-yl)-1,1-dioxo-1H-1$\lambda^6$-benzo[d]isothiazol-3-yl]-1,5-dihydro-pyrrol-2-one | >250 | 535.3 | 536.58 |
| II-37 | N-(3-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-phenyl)-acetamide | 255-260 | | 561.63 |
| II-38 | N-{3-[5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 125-132 | | 549.64 |
| II-39 | Dimethylamino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | 102-115 | | 564.66 |
| II-40 | 2-{3-[5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-acetamide | >250 | | 501.53 |
| II-41 | Amino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | | 535.2 | 536.6 |
| II-42 | Pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | 112-125 | 589.3 | 590.69 |
| II-43 | 5-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-1H-pyrimidin-2-one | >260 | 521.3 | 522.56 |
| II-44 | (S)-5-tert-Butyl-3-(1,1-dioxo-7-pyrimidin-5-yl-1H-1$\lambda^6$-benzo[d]isothiazol-3-yl)-1-(4-fluoro-benzyl)-4-hydroxy-1,5-dihydro-pyrrol-2-one | >250 | 505.3 | 506.56 |
| II-45 | Cyclopropanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | 102-105 | 560.3 | 561.65 |
| II-46 | Ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | | 548.3 | 549.64 |
| II-47 | 6-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-1H-pyridin-2-one | >250 | 520.3 | 521.57 |
| II-48 | (S)-5-tert-Butyl-3-[1,1-dioxo-7-(1H-pyrazol-4-yl)-1H-1$\lambda^6$-benzo[d]isothiazol-3-yl]-1-(4-fluoro-benzyl)-4-hydroxy-1,5-dihydro-pyrrol-2-one | >250 | 493.3 | 494.55 |
| II-49 | (R)-5-tert-Butyl-3-(1,1-dioxo-1H-1$\lambda^6$-benzo[d]isothiazol-3-yl)-1-(4-fluoro-benzyl)-4-hydroxy-1,5-dihydro-pyrrol-2-one | | 427 | 428.48 |
| II-50 | (S)-5-tert-Butyl-3-(1,1-dioxo-1H-1$\lambda^6$-benzo[d]isothiazol-3-yl)-1-(3-ethyl-4-fluoro-benzyl)-4-hydroxy-1,5-dihydro-pyrrol-2-one | 205-210 | | 456.54 |
| II-51 | (S)-3-(7-Amino-1,1-dioxo-1H-1$\lambda^6$-benzo[d]isothiazol-3-yl)-5-tert-butyl-1-(4-fluoro-benzyl)-4-hydroxy-1,5-dihydro-pyrrol-2-one | 155-160 | | 443.5 |
| II-52 | 2-({3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amino)-acetamide | 118-124 | | 514.58 |
| II-53 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-acetamide | 164.167 | | |

TABLE 2-continued

| Cpd. No. | NAME | mp | ms | mw |
|---|---|---|---|---|
| II-54 | (S)-5-tert-Butyl-3-[7-(1,1-dioxo-1$\lambda^6$-isothiazolidin-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one | 224-230 | | 561.65 |
| II-55 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methylcarbamoylmethyl-acetamide | 150-154 | | 570.64 |
| II-56 | N-{3-[(S)-5-tert-Butyl-1-(4-fluoro-3-methoxy-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 121-126 | | 565.64 |
| II-57 | 2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-N,N-dimethyl-acetamide | 185-190 | | 528.6 |
| II-58 | 2-({3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amino)-N-methyl-acetamide | 175-180 | | 528.6 |
| II-59 | N-{3-[(S)-5-tert-Butyl-1-(3-chloro-4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 125-132 | | 570.06 |
| II-60 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide | 245-250 | 520 | 521.59 |
| II-61 | 2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N,N-dimethyl-acetamide | 137 | 528 | 529.59 |
| II-62 | (S)-5-tert-Butyl-1-(2-cyclopropyl-ethyl)-3-(1,1-dioxo-1H-1$\lambda^6$-benzo[d]isothiazol-3-yl)-4-hydroxy-1,5-dihydro-pyrrol-2-one | 135-140 | | 388.49 |
| II-63 | (S)-3-(1,1-Dioxo-1H-1$\lambda^6$-benzo[d]isothiazol-3-yl)-1-(4-fluoro-benzyl)-4-hydroxy-5-isopropyl-1,5-dihydro-pyrrol-2-one | 95-110 | | 414.46 |
| II-64 | {3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-methanesulfonamide | 140-165 | | 537.59 |
| II-65 | 2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-acetamide | >210 | | 515.56 |
| II-66 | 2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetamide; compound with ammonia | >250 | | 500.55 |
| II-67 | {3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetic acid ethyl ester | 148-152 | | 529.59 |
| II-68 | (S)-3-Hydroxy-pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide | >250 | | 606.69 |
| II-69 | N-{3-[(S)-1-(3-Bromo-4-fluoro-benzyl)-5-tert-butyl-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 138-159 | | 614.51 |
| II-70 | N-{3-[(S)-5-Cyclohexyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 130-137 | | 561.65 |
| II-71 | N-{3-[(S)-5-tert-Butyl-1-(2-cyclopentyl-ethyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | 74-86 | | 523.67 |

TABLE 2-continued

| Cpd. No. | NAME | mp | ms | mw |
|---|---|---|---|---|
| II-72 | N-{3-[1-(4-Fluoro-3-methyl-benzyl)-5-(4-fluoro-phenyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide | >250 | | 587.62 |
| II-73 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-benzenesulfonamide | 96-112 | | 597.69 |
| II-74 | 1-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-3-methyl-urea | >250 | | 514-58 |
| II-75 | (S)-5-tert-Butyl-1-(4-fluoro-benzyl)-4-hydroxy-3-[7-(2-methanesulfonyl-ethyl)-1,1-dioxo-1H-1$\lambda^6$-benzo[d]isothiazol-3-yl]-1,5-dihydro-pyrrol-2-one | 127-135 | | 534.63 |
| II-76 | (S)-5-tert-Butyl-1-(4-fluoro-benzyl)-4-hydroxy-3-(7-methyl-1,1-dioxo-1H-1$\lambda^6$-benzo[d]isothiazol-3-yl)-1,5-dihydro-pyrrol-2-one | >250 | | 442.51 |
| II-77 | N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-methanesulfonamide | 105-109 | | 563.67 |
| II-78 | N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-sulfamide | 134-145 | | 550.63 |
| II-79 | 2-Amino-ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide; hydrochloride salt | 172-179 | | 564.66 |
| II-80 | (S)-5-tert-Butyl-1-(4-fluoro-benzyl)-4-hydroxy-3-(7-isobutoxy-1,1-dioxo-1H-1$\lambda^6$-benzo[d]isothiazol-3-yl)-1,5-dihydro-pyrrol-2-one | 99-106 | | 500.59 |
| II-81 | (S)-5-tert-Butyl-1-(4-fluoro-benzyl)-4-hydroxy-3-(7-methanesulfonylmethoxy-1,1-dioxo-1H-1$\lambda^6$-benzo[d]isothiazol-3-yl)-1,5-dihydro-pyrrol-2-one | 143-151 | | 536.6 |
| II-82 | Dimethyl-sulfamic acid 3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl ester | 116-126 | | 551.61 |
| II-83 | {3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide | 159-173 | | 521.59 |
| II-84 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-N',N'-dimethyl-sulfamide | 109-115 | | 578.68 |
| II-85 | (S)-5-tert-Butyl-3-[7-(1,1-dioxo-1$\lambda^6$-[1,2]thiazinan-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one | | | 575.68 |
| II-86 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-(2-methoxy-ethyl)-methanesulfonamide | — | 592.3 | 593.69 |
| II-87 | N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-(2-methylamino-ethyl)-methanesulfonamide; hydrochloride salt | — | 592.2 | 592.7 |
| II-88 | (S)-5-tert-Butyl-3-[7-(1,1-dioxo-1$\lambda^6$-[1,2,5]thiadiazolidin-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one | — | 561.3 | 562.64 |
| II-89 | C-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-methanesulfonamide | 155-165 | 550.3 | 551.62 |

TABLE 2-continued

| Cpd. No. | NAME | mp | ms | mw |
|---|---|---|---|---|
| II-90 | Morpholine-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide | 118-129 | | 606.69 |
| II-91 | Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; compound with trifluoro-acetic acid | 95-115 | 604.4 | 605.71 |
| II-92 | 4-Acetyl-piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide | 248-260 | | 647.75 |
| II-93 | N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-N-propionyl-methanesulfonamide | 98.0-99.8 | | 605.71 |
| II-94 | N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-N-butyryl-methanesulfonamide | | | 619.73 |
| II-95 | (S)-5-tert-Butyl-1-(4-fluoro-benzyl)-4-hydroxy-3-(7-methylaminomethyl-1,1-dioxo-1H-1λ⁶-benzo[d]isothiazol-3-yl)-1,5-dihydro-pyrrol-2-one; 2,2,3,3,4,4,4-heptafluoro-butyrate salt | 162-168 | 471.2 | 471.54 |
| II-96 | (S)-5-tert-Butyl-3-(7-dimethylaminomethyl-1,1-dioxo-1H-1λ⁶-benzo[d]isothiazol-3-yl)-1-(4-fluoro-benzyl)-4-hydroxy-1,5-dihydro-pyrrol-2-one; 2,2,3,3,4,4,4-heptafluoro-butyrate salt | — | 484.4 | 485.57 |
| II-97 | (S)-3-(7-Aminomethyl-1,1-dioxo-1H-1λ⁶-benzo[d]isothiazol-3-yl)-5-tert-butyl-1-(4-fluoro-benzyl)-4-hydroxy-1,5-dihydro-pyrrol-2-one; 2,2,3,3,4,4,4-heptafluoro-butyrate salt | | | |
| II-98 | Piperazine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt | 135-151 | 618.3 | 619.73 |
| II-99 | Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-methyl-amide; trifluoro-acetic acid salt | 113-128 | 618.3 | 619.73 |
| II-100 | 3-Amino-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt | 128-134 | 618.3 | 619.74 |
| II-101 | N-[1-({3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-sulfamoyl)-pyrrolidin-3-yl]-acetamide | 239-259 | 660.4 | 661.76 |
| II-102 | 3-Methanesulfonyl-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide | 124-137 | 682.2 | 682.81 |
| II-103 | C-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-yloxy}-N,N-dimethyl-methanesulfonamide | | 578.3 | 579.6 |
| II-104 | (S)-5-tert-Butyl-3-[7-(1,1-dioxo-1λ⁶-[1,2,6]thiadiazinan-2-ylmethyl)-1,1-dioxo-1H-1λ⁶-benzo[d]isothiazol-3-yl]-1-(4-fluoro-benzyl)-4-hydroxy-1,5-dihydro-pyrrol-2-one | | 575.4 | 576.66 |
| II-105 | Thiophene-2-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide | 175-192 | 602.4 | 603.7 |

TABLE 2-continued

| Cpd. No. | NAME | mp | ms | mw |
|---|---|---|---|---|
| II-106 | 1,2-Dimethyl-1H-imidazole-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt | 110-116 | 614.4 | 615.96 |

Pyrazole compounds of the present invention were prepared as depicted in SCHEME 9. The tert-butyl imine is acylated with chlorocarbonyl-acetic acid ethyl ester and the imine is reduced and the resulting hydrazine undergoes intramolecular cyclization to afford 1-tert-butyl-2-(4-fluoro-benzyl)-pyrazolidine-3,5-dione (62a) which contains an acidic β-dicarbonyl system allowing introduction of the benzo[d]isothiazole ring as described previously.

4-Hydroxy-1H-quinolin-2-ones can be introduced into the 3 position of the 1,1-dioxo-1H-1λ⁶-benzo[d]isothiazole in an analogous fashion to the pyrrolidone synthesis (SCHEME 5 supra). 4-Hydroxy-1-alkyl-(1H)quinolin-2-ones are readily accessible by condensation of an N-alkyl-isotoic anhydride and a lithium enolate to afford a β-ketoester which undergoes an intramolecular cyclization. (G. M. Coppola, *J. Het. Chem.* 1983 20(5):1217-1221, see also L. A. Mitscher et al., *Heterocycles* 1975 3(11):913-919 for a variant utilizing malonic esters). The quinolinone 63 also is an acidic 1,3-dicarbonyl which undergoes an addition-elimination reaction with 26 to afford III-1.

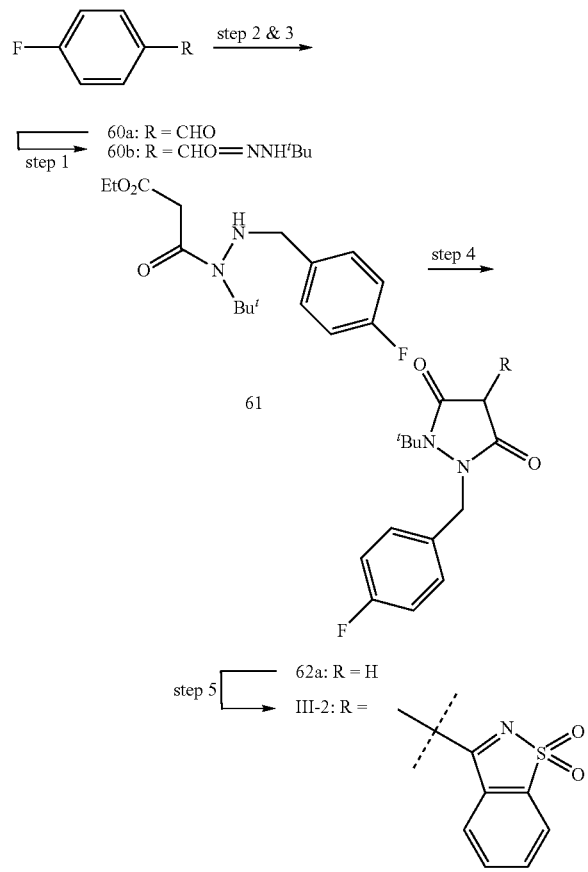

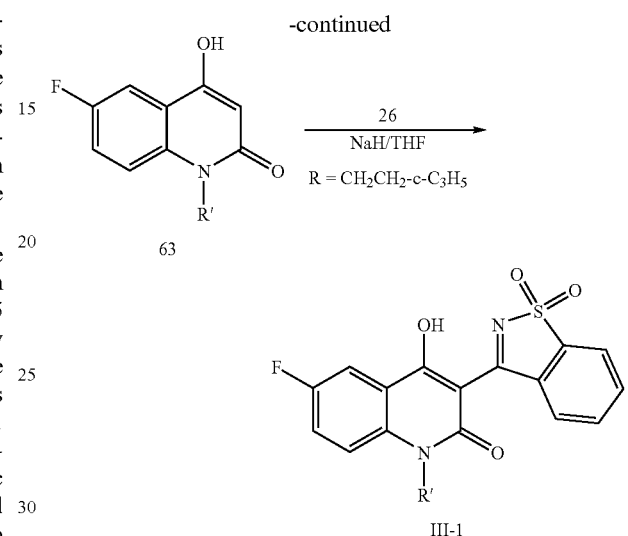

TABLE 3

| Cpd. No | NAME | mp | ms | mw |
|---|---|---|---|---|
| III-1 | 1-(2-Cyclopropyl-ethyl)-3-(1,1-dioxo-1H-1λ⁶-benzo[d]isothiazol-3-yl)-6-fluoro-4-hydroxy-1H-quinolin-2-one | | 413, 414 | 412.44 |
| III-2 | 1-tert-Butyl-4-(1,1-dioxo-1H-1λ⁶-benzo[d]isothiazol-3-yl)-2-(4-fluoro-benzyl)-5-hydroxy-1,2-dihydro-pyrazol-3-one | | 428.2 | 429.47 |

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use.

Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent. It will be understood that references herein to treatment extend to prophylaxis as well as to the treatment of existing conditions.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

3-(1,1-Dioxo-1H-1$\lambda^6$-benzo[d]isothiazol-3-yl)-1-(3-methyl-butyl)-isoquinolin-4-ol (I-1, SCHEME 1)

step 1—POCl$_3$ (40 mL) was added to a flask containing 4-hydroxy-1-oxo-1,2-dihydro-isoquinoline-3-carboxylic acid methyl ester (2, 5.00 g, 22.8 mmol). After stirring at 70° C. for 3 h, the POCl$_3$ was removed in vacuo, and water was added to the residue. The resulting solid was collected by filtration, and the solid was further washed with water and hexanes then dissolved in DCM. The DCM solution was dried (MgSO$_4$), filtered and the solvent was removed in vacuo to afford 5.10 g, (94% theory) of 3a: LCMS RT 3.6 min, M+H.

step 2—To a suspension of 3a (1.20 g, 5.05 mmol) in DMF (15 mL) was added Cs$_2$CO$_3$ (1.97 g, 6.06 mmol) followed by CH$_3$I (1.57 mL, 25.5 mmol). After stirring at RT for 20 h, the reaction mixture was diluted with EtOAc and twice washed with water and twice with brine. The organic extract was dried (MgSO$_4$), filtered and the solvent was removed in vacuo to afford 1.25 g, (98% theory) of 3b: LCMS RT 3.0 min, M+H.

step 3—To a solution of 3b (1.25 g, 4.97 mmol) and THF (12 mL) was added Pd(PPh$_3$)$_4$ (0.570 g, 0.500 mmol) followed by isoamylzinc bromide (11.9 mL, 0.5M in THF, 5.96 mmol). This mixture was stirred vigorously for 3.5 h at 70° C. and quenched with an aqueous solution of NH$_4$Cl. The resulting mixture was extracted twice with EtOAc, and the combined EtOAc extracts were washed with brine, dried (MgSO$_4$), filtered and the solvent was removed in vacuo. The product was purified by column chromatography on SiO$_2$ eluting with EtOAc/hexanes to afford 0.705 g (49% theory) of 3c: LCMS RT 3.6 min, M+H.

step 4—To a solution of 3c (700 mg, 2.44 mmol) in THF (6 mL) was added a 1M aqueous NaOH solution (24 mL, 24.0 mmol). After stirring for 18 h at 80° C., organic components were removed in vacuo. The remaining aqueous solution was twice washed with ether and acidified with 10% aqueous HCl. The aqueous acid solution was then extracted twice with EtOAc and once with DCM, and the combined organic extracts were dried (MgSO$_4$), filtered and the solvent was removed in vacuo to afford 665 mg (100% theory) 4a. LCMS RT 2.7 min, M-CO$_2$.

step 5—To a solution of 4a (0.665 g, 2.43 mmol) and DIPEA (0.53 mL, 3.00 mmol) in DCM (10 mL) was added diethyl pyrocarbonate (0.48 mL, 2.90 mmol) followed by a solution of N, O-dimethyl hydroxylamine hydrochloride (0.285 g, 2.90 mmol) and DIPEA (0.53 mL, 3.00 mmol) in CH$_2$Cl$_2$ (3 mL). The reaction mixture was stirred at RT for 3 h and then quenched with an aqueous NaHCO$_3$ solution. The resulting mixture was thrice extracted with DCM. The combined organic extracts were dried (MgSO$_4$), filtered and the solvent was removed in vacuo. The crude product was purified by column chromatography on SiO$_2$ eluting with ethyl acetate/hexanes to afford 720 mg (94% theory) of 4b: LCMS RT 3.4 min, M+H.

step 6—To a solution of N-tert-butylbenzene sulfonamide (172 mg, 0.81 mmol) in THF (2 mL) cooled to −35° C. was added a 1.6M n-BuLi solution in hexane (1.10 mL, 1.78 mmol). The reaction mixture was stirred at −35° C. for 2 h, warmed to 0° C. for 1 h, and a solution of the 4b (170 mg, 0.537 mmol) in THF (1 mL) was added. The reaction mixture was stirred at 0° C. for 1 h. The reaction was diluted with EtOAc, and the EtOAc solution was washed with water and brine. The organics were dried (MgSO$_4$), filtered and the solvent was removed in vacuo. The product was purified by column chromatography on SiO$_2$ eluting with EtOAc/hexanes to afford 50 mg, (20%) of 5: LCMS RT 4.2 min, M+H.

step 7—To a solution of 5 (50 mg, 0.11 mmol) and DCM (4 mL) cooled to 0° C. was added a 1.0 M BCl$_3$ solution in DCM (1.10 mL, 1.10 mmol). The reaction mixture was stirred at RT for 17 h and the solvent removed in vacuo. Water was added to the residue, and the resulting orange solid was collected by filtration and further washed with water. The solid was dissolved in DCM and dried (MgSO$_4$), filtered and the solvent was removed in vacuo. The product was purified by column chromatography on SiO$_2$ eluting with EtOAc/hexanes to afford 31 mg (74% theory) of 6 (I-1): LCMS RT 4.3 min, M+H.

3-(1,1-Dioxo-1H-1$\lambda^6$-benzo[d]isothiazol-3-yl)-1-(4-fluoro-benzyl)-isoquinolin-4-ol (I-2) was prepared as described for I-1 except in step 3 isoamylzinc bromide was replaced by 4-fluoro-benzylzinc bromide to afford I-5: LCMS RT 4.1 min, M+H.

3-(1,1-Dioxo-1H-1$\lambda^6$-benzo[d]isothiazol-3-yl)-1-(4-fluoro-benzyl)-isoquinolin-4-ol was prepared as described for I-1 except isoamylzinc bromide was replaced by 2-cyclopropylethylzinc chloride to afford I-3: LCMS RT 4.3 min, M+H.

3-(7-Chloro-1,1-dioxo-1H-1$\lambda^6$-benzo[d]isothiazol-3-yl)-1-(4-fluoro-benzyl)-isoquinolin-4-ol was prepared as described in Example 1 except in step 3 isoamylzinc bromide was replaced by 4-fluoro-benzylzinc bromide and in step 6 N-tert-butyl-benzenesulfonamide was replaced with N-tert-butyl-2-chloro-benzenesulfonamide which afforded 470 mg (56% theory) of I-6: LCMS RT 3.2 min, M−H.

1-(4-Fluoro-benzyl)-3-(7-methoxy-1,1-dioxo-1H-1$\lambda^6$-benzo[d]isotbiazol-3-yl)-isoquinolin-4-ol was prepared as described in Example 1 except in step 3 isoamylzinc bromide was replaced by 4-fluoro-benzylzinc bromide and in step 6 N-tert-butyl-benzenesulfonamide was replaced with N-tert-butyl-2-methoxy-benzenesulfonamide which afforded 25 mg (22% theory) of I-10: LCMS RT 3.3 min, M+H.

EXAMPLE 2

3-(1,1-Dioxo-1H-1$\lambda^6$-benzo[d]isothiazol-3-yl)-6-fluoro-1-(4-fluoro-benzyl)-isoquinolin-4-ol (I-4, SCHEME 3)

step 1—To a reddish-brown solution of 5-fluoro-isobenzofuran-1,3-dione (11 15.0 g, 90.3 mmol) and isocyano-acetic acid methyl ester (8.21 mL, 90.3 mmol) in THF (120 mL) was added dropwise a solution of 1,8-diazabicyclo[5.4.0]undec-7-ene (13.5 mL, 90.3 mmol) in THF (60 mL). The resulting red solution was stirred at RT for 1.5 h and then quenched with water (150 mL). The THF was removed in vacuo and the resulting aqueous solution was acidified to pH<3 with 10% HCl. The resulting mixture was thrice extracted with EtOAc and the combined organic extracts were washed with water, dried (MgSO$_4$), filtered and the solvent was removed in vacuo to afford 12a and 12b in a 2.5:1 ratio which was used directly in the next step.

step 2—To a solution of a mixture of the regioisomeric oxazoles 12a and 12b (24 g, 91 mmol) in MeOH (150 mL) warmed to 55° C. was added con HCl (31 mL). The resulting mixture was stirred at 55° C. for 3.5 h. The reaction mixture was diluted with water, and the resulting solid was collected by filtration and washed with water and ether to afford 20.7 g (96% theory) of a regioisomeric mixture of 13a and 13b: LCMS RT 2.6 min, M+H.

step 3—3-(1,1-Dioxo-1H-1λ⁶-benzo[d]isothiazol-3-yl)-6-fluoro-1-(4-fluoro-benzyl)-isoquinolin-4-ol was prepared by the procedure described in Example 1 except in step 1,4-hydroxy-1-oxo-1,2-dihydro-isoquinoline-3-carboxylic acid methyl ester was replaced with 13a and in step 3, isoamylzinc bromide was replaced with 4-fluoro-benzylzinc bromide to afford 107 mg of I-4: LCMS RT 4.6 min, M+H. 1-Chloro-6-fluoro-4-methoxy-isoquinoline-3-carboxylic acid methyl ester and 1-chloro-7-fluoro-4-methoxy-isoquinoline-3-carboxylic acid methyl ester were separated by SiO₂ column chromatography.

EXAMPLE 3

3-(1,1-Dioxo-1H-1λ⁶-benzo[d]isothiazol-3-yl)-1-(4-fluoro-benzyl)-6-methyl-isoquinolin-4-ol (I-5, SCHEME 2)

step 1—A mixture of 5-methyl-isobenzofuran-1,3-dione (7, 16.2 g, 100 mmol), glycine (8.25 g, 110 mmol), and xylenes (100 mL) was heated at reflux for 20 h. The resulting suspension was cooled to RT and filtered. The precipitated solid was then washed with water and hexanes to afford 7a which was used in the next step without further purification.

step 2—To a solution of 7a (20 g, 91 mmol) in MeOH (400 mL) was added H₂SO₄ (8 mL). The solution was stirred at RT for 2 d. About 200 mL of MeOH was removed in vacuo, and the remaining solution was poured into ice water and the mixture neutralized with saturated aqueous NaHCO₃. The resulting solid was then filtered, washed with water and hexanes and dissolved in DME. The organic solution was dried (MgSO₄), filtered and the solvent was removed in vacuo to afford 18.1 g (85% theory) of 7b: LCMS RT 2.9 min, did not ionize.

step 3—To NaH (1.71 g: 43 mmol; 60% suspension in mineral oil) was added MeOH (75 mL). When the mixture was homogeneous solid 7b (5.00 g, 21 mmol) was added. The resulting suspension was heated in a sealed tube at 120° C. for 3 h. The mixture became a homogeneous solution upon heating and began turning brown. After about 30 min, the reaction was green and a precipitate had formed. After 3 h, the tube was cooled to RT, opened, and water (175 mL) was added. The solution was acidified with 1M HCl (until mixture turns pink), and the resulting solid was collected by filtration. The solid was washed with water then ether to afford 4.0 g (80% theory) of a regioisomeric mixture of the isoquinolones 8 and 9 in a 1.3:1 ratio respectively: LCMS RT 2.7 min, M+H.

step 4—3-(1,1-Dioxo-1H-1λ⁶-benzo[d]isothiazol-3-yl)-1-(4-fluoro-benzyl)-6-methyl-isoquinolin-4-ol. was prepared by the procedure described in Example 1 except in step 1,4-hydroxy-1-oxo-1,2-dihydro-isoquinoline-3-carboxylic acid methyl ester was replaced with 8 and isoamylzinc bromide was replaced by 4-fluoro-benzylzinc bromide in step 3 to afford 85 mg of I-5: LCMS RT 4.8 min, M+H. 1-Chloro-6-methyl-4-methoxy-isoquinoline-3-carboxylic acid methyl ester and 1-chloro-7-methyl-4-methoxy-isoquinoline-3-carboxylic acid methyl ester were separated by fractional crystallization from MeOH and H₂O.

EXAMPLE 4

3-(1,1-Dioxo-1H-1λ⁶-benzo[d]isothiazol-3-yl)-1-[(4-fluoro-phenyl)-methyl-amino]-isoquinolin-4-ol (I-7)

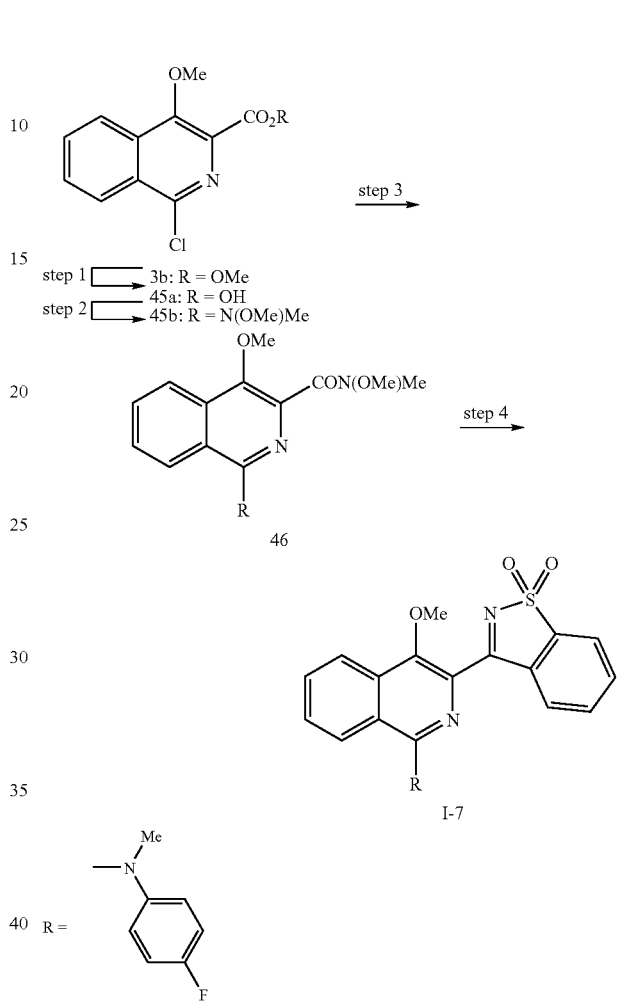

step 1—To a solution of the 3b (1.0 g, 4.0 mmol; see SCHEME 1) in THF (10 mL) was added 1M aqueous NaOH solution (40 mL, 40 mmol). The resulting suspension was heated at 80-85° C. for 1.5 h which produced a homogenous solution. The organic solvents were removed in vacuo and the resulting aqueous solution was washed with ether. The aqueous layer was acidified with 10% HCl, and resulting precipitate was filtered and washed with water. The solid was then dissolved in DCM, and the organic solution was dried (MgSO₄), filtered and the solvent was removed in vacuo to afford 850 mg (90% theory) of 45a: LCMS RT 2.4 min, M-CO₂.

step 2—To a solution of 45a (755 mg, 3.2 mmol) in DCM (10 mL) was added DIPEA (0.7 mL, 3.8 mmol) and diethyl pyrocarbonate (0.62 mL, 3.8 mmol). After stirring for several minutes, a solution of HN(OMe)Me-HCl (372 mg, 3.8 mmol) and DIPEA (0.7 mL, 3.8 mmol) in DCM (5 mL) was added. The orange reaction mixture was stirred at RT for 5 h. The reaction mixture was then quenched with saturated aqueous NaHCO₃, and the product was thrice extracted into DCM. The combined extracts were dried (MgSO₄), filtered and the solvent was removed in vacuo. The crude product was purified by column chromatography on SiO$_2$ eluting with EtOAc/hexanes to afford 889 mg (100% theory) of 45b: LCMS RT 3.0 min, M+H.

step 3—To a solution of 45b (250 mg, 0.89 mmol) in toluene (2.5 mL) was added (4-fluoro-phenyl)-methyl-amine (0.12 mL, 1.07 mmol), NaO$^t$Bu (120 mg, 1.25 mmol), (2'-dicyclohexylphosphanyl-biphenyl-2-yl)-dimethyl-amine (52.6 mg, 0.134 mmol), and Pd$_2$(dba)$_3$ (40.8 mg, 0.045 mmol). The red reaction mixture was heated at 80° C. for 3 d, and the solvent was removed in vacuo. The crude product was purified by column chromatography on SiO$_2$ eluting with EtOAc/hexanes to afford 285 mg (87% theory) of 46 (R=NMe(p-C$_6$H$_4$F)): LCMS RT 3.6 min, M+H.

step 4—3-(1,1-Dioxo-1H-1λ$^6$-benzo[d]isothiazol-3-yl)-1-[(4-fluoro-phenyl)-methyl-amino]-isoquinolin-4-ol was synthesized from 46 (R=NMe(p-C$_6$H$_4$F)) using a procedure similar to steps 6 and 7 of Example 1 except in step 6,4-hydroxy-1-oxo-1,2-dihydro-isoquinoline-3-carboxylic acid methyl ester was replaced with 46 to afford 140 mg (51% theory) of I-7: LCMS RT 4.5 min, M+H.

1-(Cyclopropylmethyl-amino)-3-(1,1-dioxo-1H-1λ$^6$-benzo[d]isothiazol-3-yl)-isoquinolin-4-ol was prepared as described for I-7 except in step 3 (fluoro-phenyl)-methyl-amine was replaced with cyclopropylmethyl amine and the final product was prepared utilizing using a procedure similar to steps 6 and 7 of Example 1 except in step 6,4-hydroxy-1-oxo-1,2-dihydro-isoquinoline-3-carboxylic acid methyl ester was replaced with 46 (R=CH$_2$-c-C$_3$H$_5$) which afforded 100 mg (51%) of I-8: LCMS RT 4.3 min, M+H.

EXAMPLE 5

1-(4-Fluoro-benzyl)-3-(7-morpholin-4-yl-1,1-dioxo-1H-1λ$^6$-benzo[d]isothiazol-3-yl)-isoquinolin-4-ol (I-11)

A mixture of 18a (R=CH$_2$-p-C$_6$H$_4$F, 120 mg, 0.27 mmol), morpholine (0.058 mL, 0.66 mmol), sodium tert-butoxide (89 mg, 0.93 mmol), (2'-dicyclohexylphosphanyl-biphenyl-2-yl)-dimethyl-amine (16 mg, 0.040 mmol), and tris-(dibenzylideneacetone)-palladium (0)(12 mg, 0.013 mmol) was stirred in toluene (1.0 mL) at 100° C. for 20 h. The toluene was removed in vacuo and water was added to the residue. The resulting solid was filtered and washed sequentially with water MeOH and Et$_2$O. The resulting solid was recrystallized from DCM/hexanes to afford 31 mg (23% theory) of I-11: LCMS RT 3.6 min, M+H.

EXAMPLE 6

1-(4-Fluoro-benzyl)-3-(7-methyl-1,1-dioxo-1H-1λ$^6$-benzo[d]isothiazol-3-yl)-isoquinolin-4-ol (I-9)

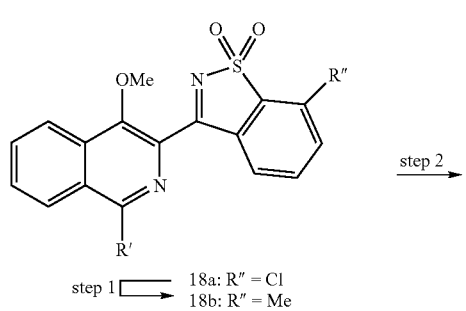

R' = CH$_2$-p-C$_6$H$_4$F

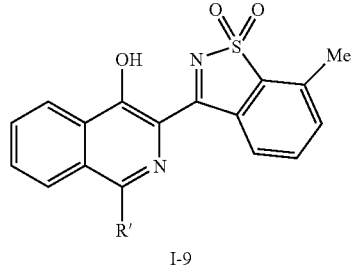

I-9 step 1—A capped tube was charged with 18a (R=CH$_2$-p-C$_6$H$_4$F, 50 mg, 0.11 mmol, Example 1), CsF (49 mg, 0.32 mmol), (2'-dicyclohexylphosphanyl-biphenyl-2-yl)-dimethyl-amine (6.3 mg, 0.016 mmol), CH$_3$B(OH)$_2$ (9.6 mg, 0.16 mmol), Pd(OAc)$_2$ (2.4 mg, 0.011 mmol) and 1,4-dioxane (0.5 mL). After heating at 100° C. for 20 h, the dioxane was removed in vacuo and 1M HCl was added. The resulting sticky solid was filtered and washed with water. The solid was then recrystallized from MeOH/water and the crude product containing 18b was used directly in the next step.

step 2—To a 0° C. solution of the crude 18b in DCM (1.5 mL) was added a 1.0 M solution of BCl$_3$ in DCM (1.5 mL, 1.5 mmol). The reaction mixture was warmed to RT, stirred for 2 h, and the solvents were removed in vacuo. Water was added to the residue, and the resulting solid was filtered, washed well with water and dissolved in DCM. The organic solution was dried (MgSO$_4$), filtered and the solvent was removed in vacuo. The crude product was purified by column chromatography on SiO$_2$ eluting with DCM and then recrystallized from MeCN to afford 19 mg (33% theory) of I-9: LCMS RT 3.7 min, M+H.

3-(1,1-Dioxo-7-phenyl-1H-1λ$^6$-benzo[d]isothiazol-3-yl)-1-(4-fluoro-benzyl)-isoquinolin-4-ol was prepared as described in example 6 except in step 3, CH$_3$B(OH)$_2$ was replaced with C$_6$H$_5$B(OH)$_2$ to afford 26 mg (39% theory) of I-12: LCMS RT 4.3 min, M+H.

1-(4-Fluoro-benzyl)-3-[7-(4-fluoro-phenyl)-1,1-dioxo-1H-1λ$^6$-benzo[d]isothiazol-3-yl]-isoquinolin-4-ol was prepared as described in example 6 except in step 3, CH$_3$B(OH)$_2$ was replaced with p-F—C$_6$H$_4$B(OH)$_2$ to afford 20 mg (62% theory) of I-14: LCMS RT 4.2 min, M+H.

1-(4-Fluoro-benzyl)-3-[7-(3-hydroxy-phenyl)-1,1-dioxo-1H-1λ$^6$-benzo[d]isothiazol-3-yl]-isoquinolin-4-ol was prepared as described in example 6 except in step 3, CH$_3$B(OH)$_2$ was replaced with m-HO—C$_6$H$_4$B(OH)$_2$ to afford 37 mg (67% theory) of I-13: LCMS RT 3.4 min, M+H.

3-(1,1-Dioxo-7-m-tolyl-1H-1λ$^6$-benzo[d]isothiazol-3-yl)-1-(4-fluoro-benzyl)-isoquinolin-4-ol was prepared as described in example 6 except in step 3, CH$_3$B(OH)$_2$ was replaced with m-Me-C$_6$H$_4$B(OH)$_2$ to afford 17 mg (49% theory) of I-15: LCMS RT 4.5 min, M+H.

1-(4-Fluoro-benzyl)-3-[7-(3-fluoro-phenyl)-1,1-dioxo-1H-1λ$^6$-benzo[d]isothiazol-3-yl]-isoquinolin-4-ol was prepared as described in example 6 except in step 3, CH$_3$B(OH)$_2$ was replaced with m-F—C$_6$H$_4$B(OH)$_2$ to afford 24 mg (40% theory) of I-17: LCMS RT 4.2 min, M+H.

N-(3-{3-[1-(4-Fluoro-benzyl)-4-hydroxy-isoquinolin-3-yl]-1,1-dioxo-1H-1λ$^6$-benzo[d]isothiazol-7-yl}-phenyl)-acetamide was prepared as described in example 6 except in step 3, CH₃B(OH)₂ was replaced with m-AcNH—C₆H₄B(OH)₂ to afford 48 mg (82% theory) of I-16: LCMS RT 3.3 min, M+H₂O.

N-(3-{3-[1-(4-Fluoro-benzyl)-4-hydroxy-isoquinolin-3-yl]-1,1-dioxo-1H-1λ⁶-benzo[d]isothiazol-7-yl}-phenyl)-methanesulfonamide was prepared as described in example 6 except in step 3, CH₃B(OH)₂ was replaced with m-MeSO₂NH—C₆H₄B(OH)₂ to afford 32 mg (47% theory) of I-18: LCMS RT 3.3 min, M+H₂O.

EXAMPLE 7

5-{3-[1-(4-Fluoro-benzyl)-4-hydroxy-isoquinolin-3-yl]-1,1-dioxo-1H-1λ⁶-benzo[d]isothiazol-7-yl}-1H-pyridin-2-one (I-25)

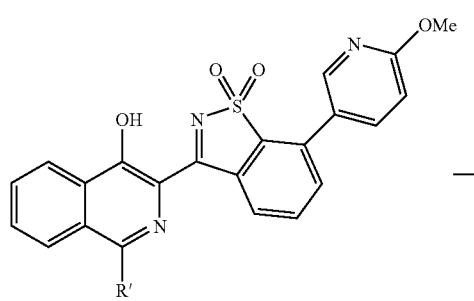

I-23

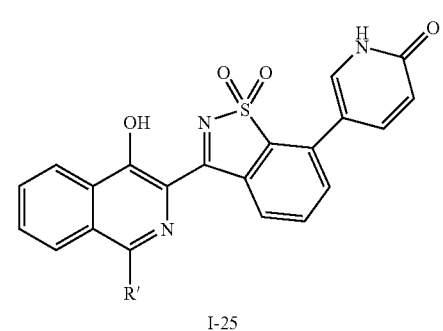

I-25

R' = CH₂-p-C₆H₄F

I-25 was synthesized using a procedure similar to Example 6 except in step 3, CH₃B(OH)₂ was replaced with 4-methoxy-3-pyridylboronic acid to afford I-23 (75 mg, 0.14 mmol). I-23 and pyridinium hydrochloride (320 mg, 2.8 mmol) were heated neat at 130° C. for 1 h. After cooling the mixture to RT, water was added. The resulting orange solid was filtered and washed sequentially with water, hexanes, and ether. The product was purified by SiO₂ column chromatography eluting with DCM/MeOH to afford 50 mg (70% theory) of I-25: LCMS RT 2.6 min, M+H.

EXAMPLE 8

6-{3-[1-(4-Fluoro-benzyl)-4-hydroxy-isoquinolin-3-yl]-1,1-dioxo-1H-1λ⁶-benzo[d]isothiazol-7-yl}-1H-pyridin-2-one (I-27)

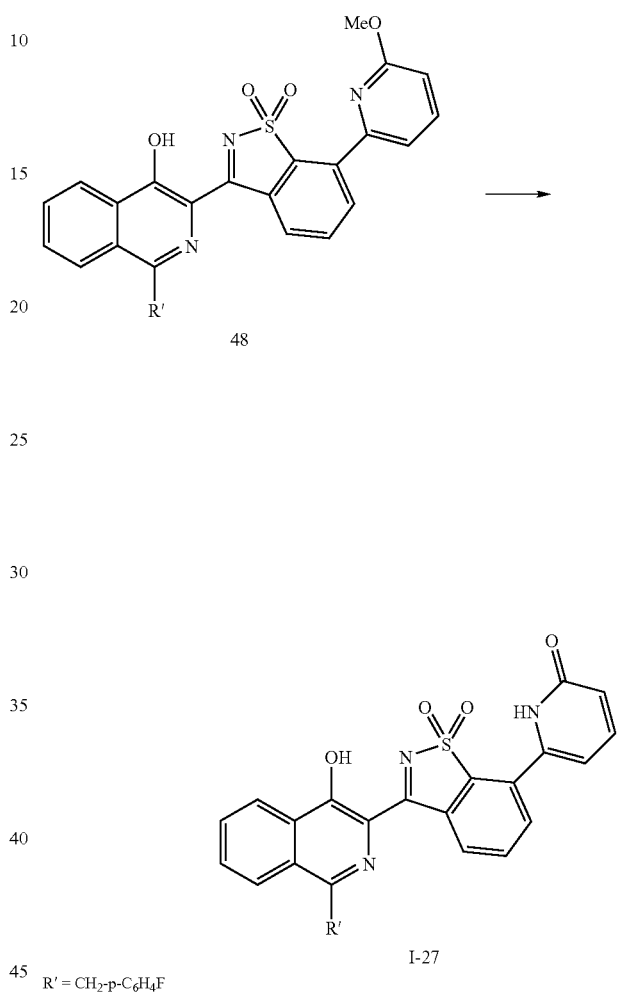

48

I-27

R' = CH₂-p-C₆H₄F

A flask was charged with I-6 (100 mg, 0.21 mmol), 2-methoxy-6-trimethylstannanyl-pyridine (64 mg, 0.24 mmol), TEA (0.090 mL, 0.64 mmol), (2'-dicyclohexylphosphanyl-biphenyl-2-yl)-dimethyl-amine (8.4 mg, 0.021 mmol), tris(dibenzylideneacetone)palladium(0) (9.8 mg, 0.011 mmol) and DMF. The solution was degassed with a stream of N₂ bubbled through the mixture for 1 min, then was heated at 100° C. for 18 h. After cooling to RT, EtOAc was added, and the organic layer was washed sequentially with 1M HCl, water, and brine. The organics were dried (MgSO₄), filtered and the solvent was removed in vacuo. The product was purified by SiO₂ chromatography eluting with DCM/EtOAc, and then heated neat at 130° C. in the presence of pyridinium hydrochloride (430 mg, 3.7 mmol) for 2 h. After cooling the mixture to RT, water was added. The resulting orange solid was collected by filtration and washed sequentially with water, hexanes and ether. The product was purified by SiO₂ chromatography eluting with DCM/MeOH to afford 30 mg (32% theory) of I-27: LCMS RT 2.6 min, M+H.

EXAMPLE 9

3-(1,1-Dioxo-7-pyridin-3-yl-1H-1λ⁶-benzo[d]
isothiazol-3-yl)-1-(4-fluoro-benzyl)-isoquinolin-4-ol
(I-19)

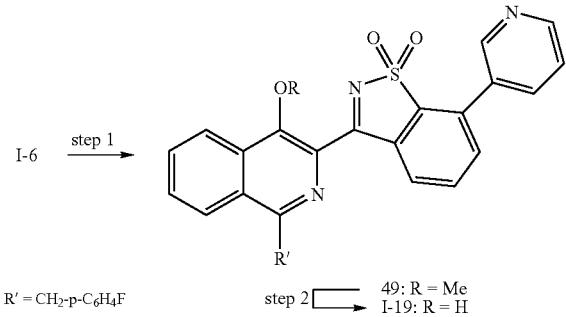

R' = CH₂-p-C₆H₄F    step 2 ⟶ 49: R = Me
                              I-19: R = H step 1—To a capped tube containing I-6 (75 mg, 0.16 mmol), 3-[1,3,2]dioxaborinan-2-yl-pyridine (31 mg, 0.19 mmol), and Pd(PPh₃)₄ (19 mg, 0.016 mmol) was added degassed DME (0.5 mL) and a degassed 2M Na₂CO₃ solution (0.16 mL). The resulting suspension was heated at 100° C. for 20 h. The reaction mixture was transferred to a flask with DCM and the solvents removed in vacuo. Water was added to the residue and the resulting orange solid was filtered. The solid was washed sequentially with water and hexanes. The product was purified by SiO₂ chromatography eluting with DCM/MeOH to afford 49.

step 2—The methyl ether was deprotected as in step 2 of Example 6 to afford 20 mg (25% theory) of I-19: LCMS RT 3.8 min, M+H.

3-[1,1-Dioxo-7-(1H-pyrazol-4-yl)-1H-1λ⁶-benzo[d]isothiazol-3-yl]-1-(4-fluoro-benzyl)-isoquinolin-4-ol was prepared as described in example 10 except in step 1, 3-[1,3,2]dioxaborinan-2-yl-pyridine was replaced with 4-(4,4,5,5-tetramethyl-[1,3,2]dioxaborolan-2-yl)pyrazole-1-carboxylic acid tert-butyl ester which afforded 4 mg (12%) of I-22: LCMS RT 3.1 min, M+MeCN.

3-(1,1-Dioxo-7-pyrimidin-5-yl-1H-1λ⁶-benzo[d]isothiazol-3-yl)-1-(4-fluoro-benzyl)-isoquinolin-4-ol was prepared as described in example 10 except in step 1 3-[1,3,2]dioxaborinan-2-yl-pyridine was replaced with 5-(4,4,5,5-tetramethyl-[1,3,2]dioxaborolan-2-yl)-pyrimidine which afforded 55 mg (81% theory) of I-24: LCMS RT 3.3 min, M+H.

EXAMPLE 10

N-{3-[1-(4-Fluoro-benzyl)-4-hydroxy-isoquinolin-3-yl]-1,1-dioxo-1H-1λ⁶-benzo[d]isothiazol-7-yl}-methanesulfonamide (I-21)

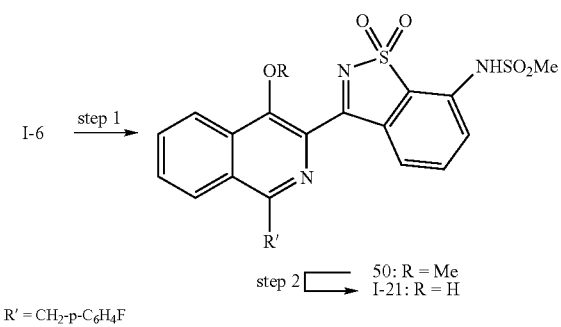

R' = CH₂-p-C₆H₄F    step 2 ⟶ 50: R = Me
                              I-21: R = H A mixture of I-6 (75 mg, 0.16 mmol), Cs₂CO₃ (73 mg, 0.23 mmol), methanesulfonamide (18 mg, 0.19 mmol), (2'-dicyclohexylphosphanyl-biphenyl-2-yl)-dimethyl-amine (9.5 mg, 0.024 mmol), and Pd₂(dba)₃ (7.4 mg, 0.008 mmol) in 1,4-dioxane (0.6 mL) was heated at 100° C. in a capped tube for 18 h. The dioxane was removed under reduced pressure, and 1M HCl and water were added. The resulting solid was filtered and washed sequentially with water and hexanes. The product was purified by SiO₂ chromatography eluting with EtOAc/hexanes. The methyl ether was deprotected as in step 2 of Example 6 to afford 49 mg (80% theory) of I-21: LCMS RT 2.7 min, M+H.

EXAMPLE 11

5-tert-Butyl-3-(1,1-dioxo-1H-1λ⁶-benzo[d]isothiazol-3-yl)-1-(4-fluoro-benzyl)-4-hydroxy-1,5-dihydro-pyrrol-2-one (II-3, SCHEME 5)

step 1—To a solution of 21 (0.87 g, 3.9 mmol) in DME (10 mL) was added 4-fluoro-benzaldehyde (0.97 g, 7.8 mmol) and HOAc (10 mL). After stirring at RT for 4 h, sodium triacetoxyborohydride (2.5 g, 12 mmol) was added. The reaction was stirred for an additional 4 h, and the solvent was removed in vacuo. The residue was then basified with aq. NaOH, and the product was extracted into DCM. The combined organic extracts were dried (MgSO₄), filtered and the solvent removed in vacuo. The product was purified by SiO₂ chromatography eluting with EtOAc/hexanes to afford 540 mg (47% theory) of 22a: LCMS RT 2.7 min, M+H.

step 2—To a solution of 22a (1.4 g, 4.7 mmol) in DCM (20 mL) was added chlorocarbonyl-acetic acid ethyl ester (1.1 g, 7.1 mmol). After stirring overnight, DIPEA (2.5 g, 19 mmol) was added, and the reaction mixture was partitioned between aqueous HCl and DCM. The organic phase was dried (MgSO₄) and removed in vacuo. The product was purified by SiO₂ chromatography eluting with EtOAc/hexanes to afford 1.2 g (62% theory) of 22b: LCMS RT 4.0 min, M+H.

step 3—To 22b (1.2 g, 2.9 mmol) was added a 0.5 M NaOMe solution in MeOH (10 mL). The reaction mixture was heated at reflux for 3 h, and the solvent was removed in vacuo. The residual phase was acidified with aqueous HCl and then heated to reflux in THF (10 mL) for 4 h. The reaction mixture was cooled to RT and extracted into DCM, and the combined extracts were dried (MgSO₄) and the solvent removed in vacuo to afford 500 mg (65% theory) of 23: LCMS RT 2.7 min, no parent molecular ion was observed.

step 4—To a solution of saccharin (25, 5.0 g, 27 mmol) in dioxane (100 mL) was added thionyl chloride (3.0 mL, 41 mmol) and DMF (5 drops). The reaction mixture was heated at reflux for 2 d, and the lightly colored solution was cooled to RT. The solvent was removed in vacuo to afford 4.2 g of 26 as an off-white solid that was recrystallized from toluene: LCMS RT 2.6 min, M+H.

step 5—To a solution of 23 (0.40 g, 1.6 mmol) in THF (8 mL) was added NaH (0.14 g, 3.6 mmol, 60% suspension in mineral oil), and the reaction was stirred at RT for 10 min. The chloride 26 (0.30 g, 1.5 mmol) was then added, and the reaction mixture was heated at 60° C. for 1 h. The solvent was then removed in vacuo, and the residue partitioned between DCM and aqueous HCl. The organic layer was dried (MgSO₄), and the solvent was removed in vacuo. The product was purified by SiO$_2$ chromatography eluting with EtOAc/DCM to afford 100 mg (16% theory) of II-3: LCMS RT 1.5 min, M–H.

1-Benzyl-5-tert-butyl-3-(1,1-dioxo-1H-1λ$^6$-benzo[d]isothiazol-3-yl)-4-hydroxy-1,5-dihydro-pyrrol-2-one was prepared as described in example 11 except in step 1 4-fluoro-benzaldehyde was replaced with benzaldehyde to afford 100 mg (16% theory) of II-2: LCMS RT 1.5 min, M–H.

1-Benzyl-5-cyclohexyl-3-(1,1-dioxo-1H-1λ$^6$-benzo[d]isothiazol-3-yl)-4-hydroxy-1,5-dihydro-pyrrol-2-one was prepared as described in example 11 except in step 1, (S)-2-Amino-3,3-dimethyl-butyric acid tert-butyl ester was replaced with (S)-amino-cyclohexyl-acetic acid methyl ester and 4-fluoro-benzaldehyde was replaced with benzaldehyde to afford 35 mg (10% theory) of II-1: LCMS RT 2.5 min, M–H.

5-tert-Butyl-3-(1,1-dioxo-1H-1λ$^6$-benzo[d]isothiazol-3-yl)-4-hydroxy-1-(4-methyl-benzyl)-1,5-dihydro-pyrrol-2-one was prepared as described in example 11 except in step 1,4-fluoro-benzaldehyde was replaced with 4-methylbenzaldehyde and (S)-2-Amino-3,3-dimethyl-butyric acid tert-butyl ester was replaced with (S)-2-amino-3,3-dimethyl-butyric acid methyl ester to afford 56 mg (16% theory) of II-9: LCMS RT 2.4 min, M–H.

5-tert-Butyl-3-(1,1-dioxo-1H-1λ$^6$-benzo[d]isothiazol-3-yl)-1-(4-fluoro-3-methoxy-benzyl)-4-hydroxy-1,5-dihydro-pyrrol-2-one was prepared as described in example 11 except in step 1, 4-fluoro-benzaldehyde was replaced with 4-fluoro-3-methoxy-benzaldehyde and (S)-2-amino-3,3-dimethyl-butyric acid tert-butyl ester was replaced with (S)-2-amino-3,3-dimethyl-butyric acid methyl ester to afford 25 mg (7% theory) of II-10: LCMS RT 2.3 min, M–H.

5-tert-Butyl-3-(1,1-dioxo-1H-1λ$^6$-benzo[d]isothiazol-3-yl)-4-hydroxy-1-thiophen-2-ylmethyl-1,5-dihydro-pyrrol-2-one was prepared as described in example 11 except in step 1,4-fluoro-benzaldehyde was replaced with thiophene-2-carboxaldehyde and (S)-2-amino-3,3-dimethyl-butyric acid tert-butyl ester was replaced with (S)-2-amino-3,3-dimethyl-butyric acid methyl ester to afford 89 mg (18% theory) of II-11: LCMS RT 2.2 min, M–H.

5-tert-Butyl-1-(4-chloro-benzyl)-3-(1,1-dioxo-1H-1λ$^6$-benzo[d]isothiazol-3-yl)-4-hydroxy-1,5-dihydro-pyrrol-2-one was prepared as described in example 11 except in step 1,4-fluoro-benzaldehyde was replaced with 4-chloro-benzaldehyde and (S)-2-amino-3,3-dimethyl-butyric acid tert-butyl ester was replaced with (S)-2-amino-3,3-dimethyl-butyric acid methyl ester to afford 47 mg (12% theory) of II-13: LCMS RT 2.4 min, M–H 4-[2-tert-Butyl-4-(1,1-dioxo-1H-1λ$^6$-benzo[d]isothiazol-3-yl)-3-hydroxy-5-oxo-2,5-dihydro-pyrrol-1-ylmethyl]-benzonitrile was prepared as described in example 11 except in step 1, 4-fluoro-benzaldehyde was replaced with 4-formylbenzonitrile and (S)-2-amino-3,3-dimethyl-butyric acid tert-butyl ester was replaced with (S)-2-amino-3,3-dimethyl-butyric acid methyl ester to afford 66 mg (15% theory) of II-14: LCMS RT 2.2 min, M–H 5-tert-Butyl-3-(1,1-dioxo-1H-1λ$^6$-benzo[d]isothiazol-3-yl)-1-(4-fluoro-3-methyl-benzyl)-4-hydroxy-1,5-dihydro-pyrrol-2-one was prepared as described in example 11 except in step 1, 4-fluoro-benzaldehyde was replaced with 4-fluoro-3-methyl-benzaldehyde and (S)-2-amino-3,3-dimethyl-butyric acid tert-butyl ester was replaced with (S)-2-amino-3,3-dimethyl-butyric acid methyl ester to afford 64 mg (11% theory) of H-15: LCMS RT 2.4 min, M–H.

5-tert-Butyl-1-cyclobutylmethyl-3-(1,1-dioxo-1H-1λ$^6$-benzo[d]isothiazol-3-yl)-4-hydroxy-1,5-dihydro-pyrrol-2-one was prepared as described in example 11 except in step 1,4-fluoro-benzaldehyde was replaced with cyclobutanecarbaldehyde to afford 71 mg (15%.) of II-17: LCMS RT 2.2 min, M–H.

5-tert-Butyl-1-(3,3-dimethyl-butyl)-3-(1,1-dioxo-1H-1λ$^6$-benzo[d]isothiazol-3-yl)-4-hydroxy-1,5-dihydro-pyrrol-2-one was prepared as described in example 11 except in step 1,4-fluoro-benzaldehyde was replaced with 3,3-dimethylbutanal to afford 260 mg, (70%) of II-21: LCMS RT 2.5 min, M–H.

5-tert-Butyl-1-(3,4-difluoro-benzyl)-3-(1,1-dioxo-1H-1λ$^6$-benzo[d]isothiazol-3-yl)-4-hydroxy-1,5-dihydro-pyrrol-2-one was prepared as described in example 11 except in step 1,4-fluoro-benzaldehyde was replaced with 3,4-difluorobenzaldehyde to afford 62 mg (16%) of II-24: LCMS RT 2.4 min, M–H.

5-tert-Butyl-3-(1,1-dioxo-1H-1λ$^6$-benzo[d]isothiazol-3-yl)-1-(4-fluoro-3-trifluoromethyl-benzyl)-4-hydroxy-1,5-dihydro-pyrrol-2-one was prepared as described in example 11 except in step 1, 4-fluoro-benzaldehyde was replaced with 4-fluoro-3-(trifluoromethyl)benzaldehyde to afford 130 mg (29%) of II-26: LCMS RT 2.6 min, M–H.

1-(3-Bromo-4-fluoro-benzyl)-5-tert-butyl-3-(1,1-dioxo-1H-1λ$^6$-benzo[d]isothiazol-3-yl)-4-hydroxy-1,5-dihydro-pyrrol-2-one was prepared as described in example 11 except in step 1, fluoro-benzaldehyde was replaced with 3-bromo-4-fluorobenzaldehyde to afford 60 mg (14%) of II-22: LCMS RT 2.6 min, M–H.

5-[2-tert-Butyl-4-(1,1-dioxo-1H-1λ$^6$-benzo[d]isothiazol-3-yl)-3-hydroxy-5-oxo-2,5-dihydro-pyrrol-1-ylmethyl]-2-fluoro-benzonitrile was prepared as described in example 11 except in step 1, fluoro-benzaldehyde was replaced with 2-fluoro-5-formylbenzonitrile to afford 18 mg (4%) of II-25: LCMS RT 2.3 min, M–H.

5-tert-Butyl-1-(3-cyclopropyl-4-fluoro-benzyl)-3-(1,1-dioxo-1H-1λ$^6$-benzo[d]isothiazol-3-yl)-4-hydroxy-1,5-dihydro-pyrrol-2-one was prepared as described in example 11 except in step 1, fluoro-benzaldehyde was replaced with 3-cyclopropyl-4-fluorobenzaldehyde to afford 39 mg (8%) of II-30: LCMS RT 2.6 min, M–H.

5-tert-Butyl-1-(3-chloro-4-fluoro-benzyl)-3-(1,1-dioxo-1H-1λ$^6$-benzo[d]isothiazol-3-yl)-4-hydroxy-1,5-dihydro-pyrrol-2-one was prepared as described in example 11 except in step 1, fluoro-benzaldehyde was replaced with 3-chloro-4-fluorobenzaldehyde to afford 45 mg (9%) of II-31: LCMS RT 2.5 min, M–H.

EXAMPLE 12

5-[(S)-2-tert-Butyl-4-(1,1-dioxo-1H-1λ$^6$-benzo[d]isothiazol-3-yl)-3-hydroxy-5-oxo-2,5-dihydro-pyrrol-1-ylmethyl]-1H-pyridin-2-one (I-29)

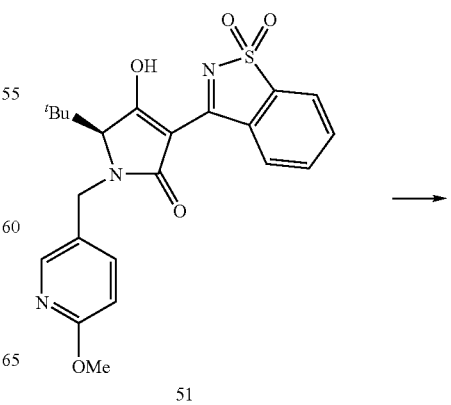

51

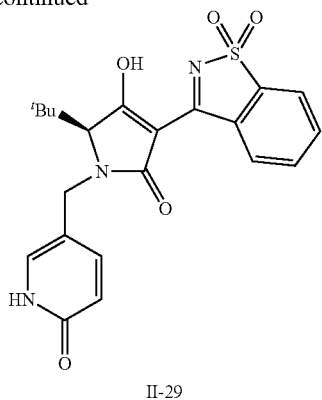

II-29

5-tert-Butyl-3-(1,1-dioxo-1H-1$\lambda^6$-benzo[d]isothiazol-3-yl)-4-hydroxy-1-(6-methoxy-pyridin-3-ylmethyl)-1,5-dihydro-pyrrol-2-one was prepared as described in example 11 except in step 1, p-fluorobenzaldehyde was replaced by 6-methoxynicotinaldehyde to afford 700 mg (100%) of 51: LCMS RT 2.1 min, M−H.

To a solution of 51 (400 mg, 0.9 mmol) in xylenes (5 mL) was added AlCl$_3$ (600 mg, 5 mmol) and the mixture heated to 80° C. for 1 h. The mixture was poured into 1M HCl, and the solid extracted into EtOAc (2×). The organic extracts were washed with brine, dried (MgSO$_4$), and concentrated in vacuo. The product was purified by column chromatography on SiO$_2$ eluting with DCM/MeOH/HOAc to afford 100 mg (26%) of II-29: LCMS RT 1.7 min, M−H.

EXAMPLE 13

5-tert-Butyl-3-(7-chloro-1,1-dioxo-1H-1$\lambda^6$-benzo[d]isothiazol-3-yl)-1-(4-fluoro-benzyl)-4-hydroxy-1,5-dihydro-pyrrol-2-one (II-4)

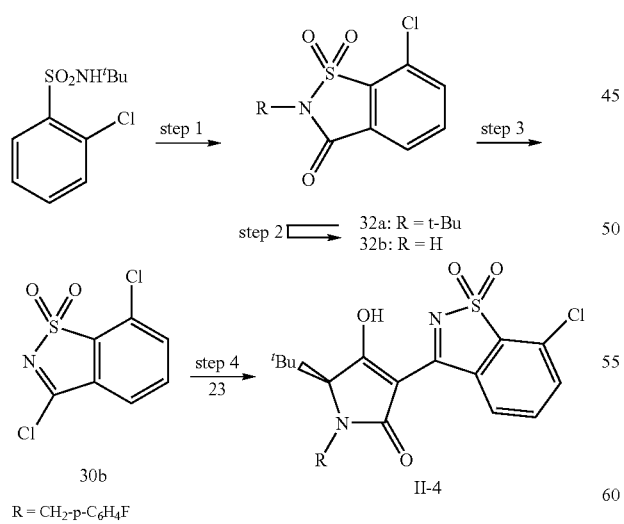

step 1—To a solution of N-tert-butyl-2-chloro-benzenesulfonamide (0.88 g, 3.6 mmol) in THF (10 mL) cooled to −23° C. was added a 2.5M solution of n-BuLi in hexanes (3.6 mL, 8.9 mmol). After stirring at −23° C. for 1 h, isobutylchloroformate (0.77 g, 7.1 mmol) was added. The reaction was warmed to RT, stirred overnight, and then poured into water. The organics were removed in vacuo, and the residue was extracted with DCM. The combined extracts were dried (MgSO$_4$) and the solvent was removed in vacuo. The product was purified by column chromatography on SiO$_2$ eluting with EtOAc/hexanes to afford 900 mg (93% theory) of 32a LCMS RT 2.7 min, no parent molecular ion was observed.

step 2—To a solution of 32a (900 mg, 3.3 mmol) in DCM (10 mL) cooled to 0° C. was added a 1.0M BCl$_3$ solution in DCM (15 mL, 15 mmol). The reaction mixture was warmed to RT, stirred for 4 h, and then poured into water. The product was extracted into DCM and the combined extracts were dried (MgSO$_4$) and the solvent was removed in vacuo. The crude product was purified by column chromatography on SiO$_2$ eluting with EtOAc/hexanes to afford 300 mg (42% theory) of 32b: LCMS RT 1.0 min, no parent molecular ion was observed.

step 3—A mixture of the 32b, thionyl chloride (10 mL), and DMF (0.2 mL) were heated at 75° C. for 8 h, and the solvents were removed in vacuo. The residue was twice azeotroped with toluene to afford 215 mg, (65% theory) of 30b: LCMS RT 3.0 min, no parent molecular ion was observed.

step 4—To a solution of 23 (R=CH$_2$-p-C$_6$H$_4$F, 0.18 g, 0.68 mmol) in THF (3 mL) was added NaH (55 mg, 1.4 mmol, 60% suspension in mineral oil). The reaction was stirred at RT for 20 min and 30b (0.16 g, 0.68 mmol) was added. The resulting mixture was stirred at RT for 3 h. The solvent was removed in vacuo, and the residue partitioned between DCM and aqueous HCl. The organic layer was dried (MgSO$_4$) and the solvent was removed in vacuo. The product was purified by column chromatography on SiO$_2$ eluting with EtOAc/DCM to afford 98 mg (31% theory) of II-4: LCMS RT 1.6 min, M−H.

5-tert-Butyl-1-(4-fluoro-benzyl)-4-hydroxy-3-(7-methoxy-1,1-dioxo-1H-1$\lambda^6$-benzo[d]isothiazol-3-yl)-1,5-dihydro-pyrrol-2-one was prepared as described in example 13 except in step 1 N-tert-butyl-2-chloro-benzenesulfonamide was replaced with N-tert-butyl-2-methoxy-benzenesulfonamide to afford 100 mg (29% theory) of II-5: LCMS RT 2.5 min, M−H.

5-tert-Butyl-3-(1,1-dioxo-1H-1$\lambda^6$-naphtho[2,1-d]isothiazol-3-yl)-1-(4-fluoro-benzyl)-4-hydroxy-1,5-dihydro-pyrrol-2-one was prepared as described in example 13 except in step 1 N-tert-butyl-2-chloro-benzenesulfonamide was replaced with naphthalene-1-sulfonic acid tert-butylamide to afford 70 mg (13% theory) of II-7: LCMS RT 1.7 min, M−H.

EXAMPLE 14

5-tert-Butyl-1-(4-fluoro-benzyl)-4-hydroxy-3-(7-hydroxy-1,1-dioxo-1H-1$\lambda^6$-benzo[d]isothiazol-3-yl)-1,5-dihydro-pyrrol-2-one (II-6)

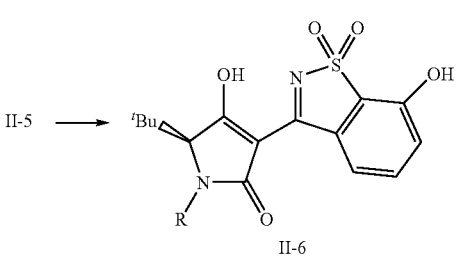

To a solution of the II-5 and xylenes (1 mL) was added AlCl$_3$ (81 mg, 0.61 mmol). The reaction was heated at 75° C. for 2 h, and then cooled to RT. Water was added, and the product was extracted into EtOAc. The organic layer was dried (MgSO$_4$), and the solvent was removed in vacuo. The product was purified by column chromatography on SiO$_2$ eluting with MeOH/DCM to afford 36 mg (53% theory) of II-6: LCMS RT 1.6 min, M−H.

EXAMPLE 15

(S)-5-tert-Butyl-3-(1,1-dioxo-7-pyridin-3-yl-1H-1$\lambda^6$-benzo[d]isothiazol-3-yl)-1-(4-fluoro-benzyl)-4-hydroxy-1,5-dihydro-pyrrol-2-one (II-32)

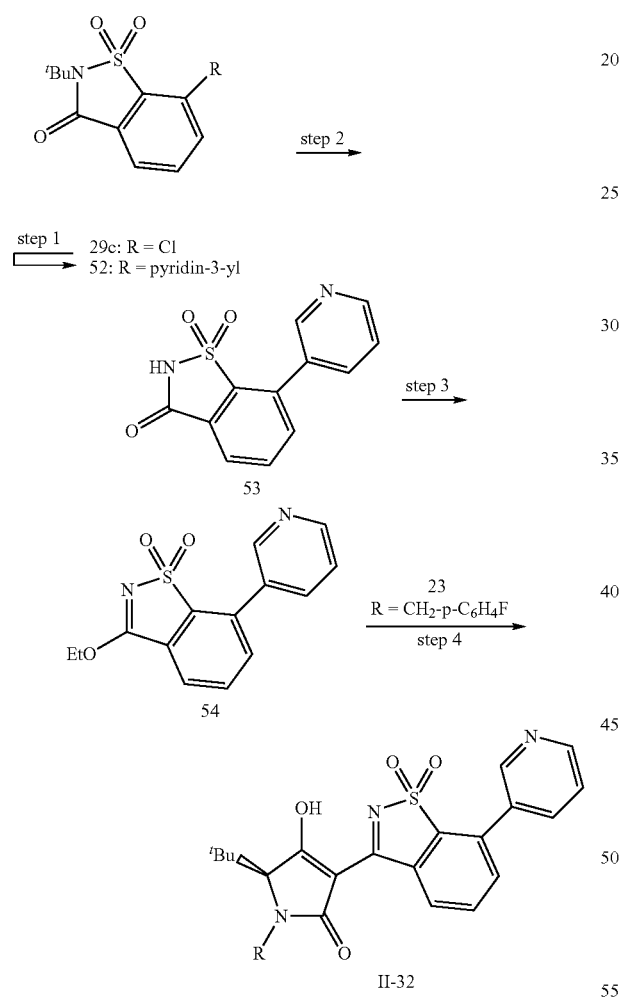

step 1—To a mixture of 32a (500 mg, 1.8 mmol), 3-(1,3,2-dioxaborinan-2-yl)pyridine (357 mg, 2.2 mmol), and Pd(PPh$_3$)$_4$ (211 mg, 0.18 mmol) was added DME (4.2 mL) and 2M aqueous Na$_2$CO$_3$ (1.8 mL, 3.6 mmol). Nitrogen was bubbled through the solution for 1 minute, and the mixture was capped and heated at 100° C. for 19 h (The solution became a yellow solution upon heating). The reaction mixture was concentrated under reduced pressure and diluted with EtOAc and water. The layers were separated, and the aqueous layer extracted one more time with EtOAc. The combined EtOAc extracts were washed with brine, dried (MgSO$_4$), filtered and concentrated under reduced pressure. The product was purified by SiO$_2$ chromatography eluting with hexanes/EtOAc to afford 210 mg (36%) of 52: LCMS RT 2.3 min, M+H.

step 2—To a solution of sulfonamide 52 (250 mg, 0.79 mmol) in DCM (1 mL) was added BCl$_3$ (3.95 ml, 3.95 mmol). The reaction mixture was stirred at RT for 2 h, concentrated under reduced pressure, and 1M HCl was added. The resulting solid was collected by filtration and washed with water and hexanes and then purified by SiO$_2$ chromatography eluting with EtOAc/MeOH to afford 53. The recovered product was about 80% pure and was used directly in the next step.

step 3—To a suspension of 53 (330 mg, 1.3 mmol) in dioxane (1.8 mL) was added thionyl choride (0.56 mL, 7.6 mmol), followed by DMF (0.015 mL, 0.19 mmol). The reaction mixture was heated at 100° C. for 17 h, and then another portion of thionyl chloride (0.56 mL) was added. The reaction was then heated at 100° C. for an additional 36 h and concentrated under reduced pressure. EtOH (5 mL) was added, and the mixture was refluxed for 2 h. (The solid did not dissolve upon heating.) The mixture was cooled in an ice bath and filtered. The solid was washed with cold EtOH then ether. A solid also formed in the filtrate after washing with ether and that solid was collected and washed with ether and the solids combined to afford 110 mg (30%) of 54.

step 4—To a solution of 23 (0.075 g, 0.28 mmol) in THF (1.5 mL) was added NaH (0.016 g, 0.40 mmol). The reaction mixture was stirred at RT for 20 min, and then 54 (0.11 g, 0.37 mmol) was added as a solid. The reaction was then stirred at RT for 18 h. The reaction was then concentrated under reduced pressure and partitioned between 1M HCl and CHCl$_3$. The aqueous layer was extracted one more time with CHCl$_3$, and the combined organics were dried (MgSO$_4$), filtered and concentrated under reduced pressure. The product was purified by SiO$_2$ chromatography eluting with DCM/MeOH to afford 29 mg (20%) of II-32: LCMS RT 2.5 min, M−H.

EXAMPLE 16

(S)-5-tert-Butyl-1-(4-fluoro-benzyl)-4-hydroxy-3-[7-(6-methoxy-pyridin-3-yl)-1,1-dioxo-1H-1$\lambda^6$-benzo[d]isothiazol-3-yl]-1,5-dihydro-pyrrol-2-one (II-33) and 5-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-1H-pyridin-2-one (II-34)

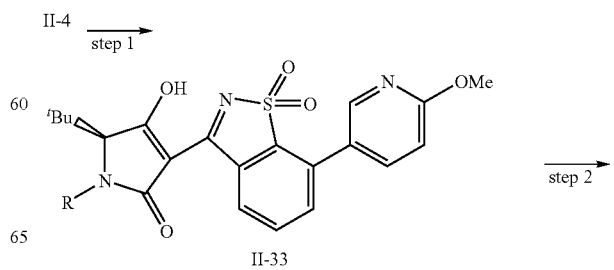

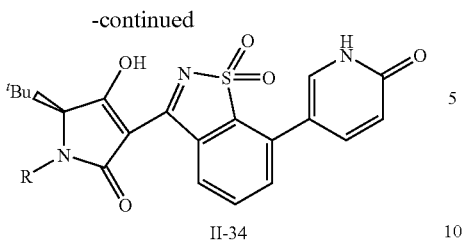

II-34

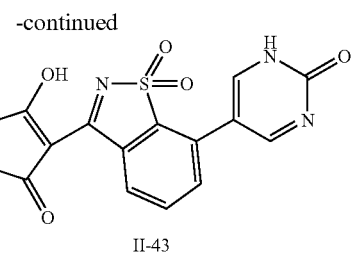

II-43 step 1—A tube containing a mixture of chloride II-4 (0.350 g, 0.756 mmol), CsF (0.345 g, 2.27 mmol), 6-methoxypyridin-3-ylboronic acid (0.231 g, 1.51 mmol), (2'-dicyclohexylphosphanyl-biphenyl-2-yl)-dimethyl-amine (0.0446 g, 0.113 mmol), Pd(OAc)$_2$ (0.0170 g, 0.0756 mmol) and dioxane (3 mL) was degassed by bubbling N$_2$ through the solution, sealed and heated at 100° C. for 18 h. The reaction mixture was concentrated under reduced pressure and diluted with EtOAc and 1M HCl. The layers were separated, and the aqueous layer was extracted once more with EtOAc. The combined organic extracts were washed with brine, dried (MgSO$_4$) and concentrated under reduced pressure. The product was purified by SiO$_2$ column chromatography eluting with DCM/MeOH to afford 385 mg (90%) of II-33: LCMS RT 2.2 min, M−H.

step 2—To a solution of II-33 (0.300 g, 0.560 mmol) in xylenes (3 mL) was added AlCl$_3$ (0.373 g, 2.80 mmol). The suspension was heated at 80° C. for 1 h, cooled to RT and poured into 1M HCl. The product was then extracted into EtOAc (1×) and CHCl$_3$ (1×), and the combined organic extracts were dried (Na$_2$SO$_4$), filtered and concentrated in vacuo. The product was purified by column chromatography on SiO$_2$ eluting with DCM/MeOH to afford 142 mg (40%) of II-34: LCMS RT 1.9 min, M−H.

5-tert-Butyl-3-(1,1-dioxo-7-pyrimidin-5-yl-1H-1λ$^6$-benzo[d]isothiazol-3-yl)-1-(4-fluoro-benzyl)-4-hydroxy-1,5-dihydro-pyrrol-2-one was prepared as described in example 15 except in step 1, 6-methoxypyridin-3-ylboronic acid was replaced by pyrimidin-5-ylboronic acid to afford 80 mg (52%) of II-44: LCMS RT 2.3 min, M−H.

5-tert-Butyl-1-(4-fluoro-benzyl)-4-hydroxy-3-[7-(2-methoxy-pyrimidin-5-yl)-1,1-dioxo-1H-1λ$^6$-benzo[d]isothiazol-3-yl]-1,5-dihydro-pyrrol-2-one was prepared as described in step 1 of example 15 except in step 1,6-methoxypyridin-3-ylboronic acid was replaced by 2-methoxypyrimidin-5-ylboronic acid to afford 132 mg (33%) of II-36 LCMS RT 2.1 min, M−H.

EXAMPLE 17

5-{3-[(S)-5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyrimidin-2-one (II-43)

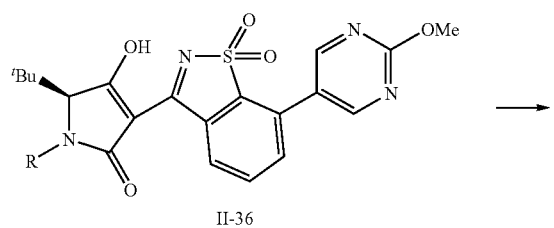

II-36

A mixture of II-36 50 (0.100 g, 0.19 mmol), dioxane (2 mL), and 2M HCl (1.9 ml, 3.7 mmol) was stirred at 100° C. for 4 h. The dioxane was removed in vacuo, and the resulting aqueous layer was diluted with water and the product was extracted into EtOAc (2×) and CHCl$_3$ (1×). The combined organics were dried (Na$_2$SO$_4$), filtered and concentrated in vacuo. The product was purified by column chromatography on SiO$_2$ eluting with DCM/MeOH to afford 70 mg (72%) of II-43: LCMS RT 1.8 min, M−H.

EXAMPLE 18

6-{3-[(S)-5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyridin-2-one (II-47)

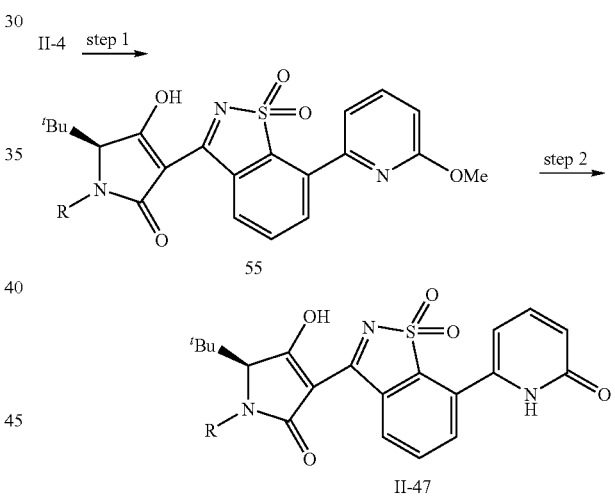

step 1—A mixture of II-4 (0.200 g, 0.43 mmol), 2-methoxy-6-(tributylstannyl)pyridine (0.38 g, 0.86 mmol), TEA (0.18 ml, 1.3 mmol), (dicyclohexylphosphanyl-biphenyl-2-yl)-dimethyl-amine (0.017 g, 0.043 mmol), and tris(dibenzylideneacetone)palladium(0) (0.020 g, 0.022 mmol) was dissolved in DMF (2 mL), degassed by bubbling N$_2$ through the solution and then heated at 100° C. over the weekend. The mixture was then diluted with EtOAc, and the organic extract was washed with 1M HCl, water, and brine, dried (MgSO$_4$), filtered and concentrated in vacuo. The product was purified by SiO$_2$ chromatography eluting with hexanes/EtOAc to 55 as slightly impure product that was used directly in the next step.

step 2—6-{3-[5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyridin-2-one was prepared from 55 by the procedure described in example 17 to afford 30 mg (21%) of II-47: LCMS RT 2.0 min, M−H.

EXAMPLE 19

(S)-5-tert-Butyl-3-[1,1-dioxo-7-(1H-pyrazol-4-yl)-1H-1λ⁶-benzo[d]isothiazol-3-yl]-1-(4-fluoro-benzyl)-4-hydroxy-1,5-dihydro-pyrrol-2-one (II-48)

To a capped tube was added II-4 (0.200 g, 0.43 mmol), tert-butyl 4-(4,4,5,5-tetramethyl-1,3,2-dioxaborolan-2-yl)-1H-pyrazole-1-carboxylate (0.25 g, 0.86 mmol), Pd(PPh$_3$)$_4$ (0.075 g, 0.065 mmol), DME (2 ml) and 2M aqueous Na$_2$CO$_3$ (0.43 mL, 0.86 mmol). The suspension was briefly degassed by bubbling nitrogen through it, and then heated at 100° C. for 19 h. The dark brown reaction was then concentrated under reduced pressure and partitioned between 1M HCl and CHCl$_3$. The aqueous layer was extracted one more time with CHCl$_3$, and the combined organic extracts were washed with brine, dried (MgSO$_4$), filtered and concentrated in vacuo. The product was purified by SiO$_2$ column chromatography eluting with DCM/MeOH to afford 46 mg (22%) of II-48: LCMS RT 2.3 min, M−H.

EXAMPLE 20

(S)-3-(7-Amino-1,1-dioxo-1H-1λ⁶-benzo[d]isothiazol-3-yl)-5-tert-butyl-1-(4-fluoro-benzyl)-4-hydroxy-1,5-dihydro-pyrrol-2-one (II-51)

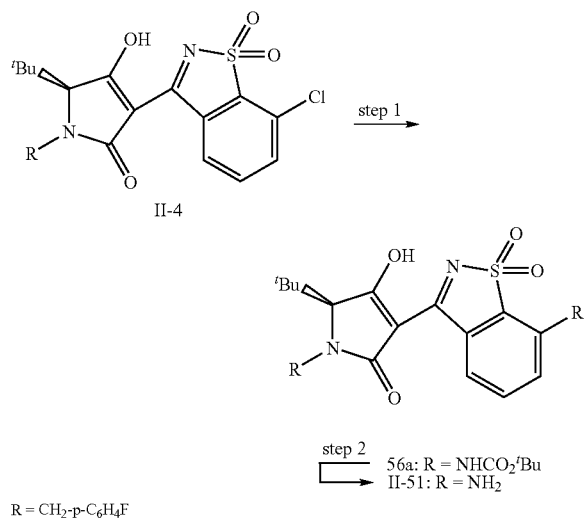

R = CH$_2$-p-C$_6$H$_4$F step 1—To a capped tube was added II-4 (0.100 g, 0.22 mmol), tert-butyl carbamate (0.051 g, 0.43 mmol), Cs$_2$CO$_3$ (0.14 g, 0.43 mmol), (dicyclohexylphosphanyl-biphenyl-2-yl)-dimethylamine (0.013 g, 0.032 mmol), tris(dibenzylideneacetone)palladium(0) (0.0099 g, 0.011 mmol) and dioxane (1.0 mL). The brown reaction mixture was heated at 100° C. for 22 h and then water was added. The solution was acidified to ca. pH 4 with 1M HCl The product was extracted into EtOAc (2×), and the combined organic extracts were washed with brine, dried (MgSO$_4$), filtered and concentrated in vacuo. The product was purified by column chromatography on SiO$_2$ eluting with hexanes/EtOAc to afford 87 mg (74%) of 56: LCMS RT 2.6 min, M−H.

step 2—A mixture of 56 (0.085 g, 0.16 mmol) and 4M HCl in dioxane (1.4 ml, 5.5 mmol) was stirred at RT for 17 h. The reaction mixture was concentrated in vacuo and ether was added followed by hexanes. The precipitated yellow solid was collected by filtration and further washed with hexanes to afford 50 mg (72%) of II-51: LCMS RT 1.9 min, M−H.

EXAMPLE 21

N-{3-[5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide (II-23, SCHEME 8)

step 1—A flask fitted with a pressure-release gas inlet was charged with 35a (5.0 g, 18 mmol), Pd(OAc)$_2$ (410 mg, 1.8 mmol), cesium fluoride (8.3 g, 55 mmol), methylboronic acid (4.4 g, 73 mmol) and dicyclohexylphosphanyl-biphenyl-2-yl)-dimethyl-amine (1.1 g, 2.7 mmol). After 3 vacuum/argon flush cycles, dioxane (50 mL) was added, and the reaction mixture was stirred at 90° C. for 12 h. The reaction was quenched with saturated aqueous NH$_4$Cl, filtered through a pad of CELITE®, and the product was extracted into EtOAc (2×). The combined organics were dried (Na$_2$SO$_4$) and concentrated in vacuo. The product was purified by column chromatography on SiO$_2$ eluting with EtOAc/hexanes to afford 3.2 g (69%) of 40b: LCMS RT 3.3 min, M-C$_4$H$_{10}$.

step 2—To a solution of 40b (4.0 g, 16 mmol) in CCl$_4$ (75 mL) was added NBS (3.4 g, 19 mmol). The reaction mixture was heated at 85° C. overnight, cooled and filtered. The solid succinimide was washed with CCl$_4$, and the filtrate was concentrated in vacuo. The product was purified by column chromatography on SiO$_2$ eluting with ether/hexanes to afford 2.1 g (40%) of 40c: LCMS RT 3.3 min, M-C$_4$H$_{10}$.

step 3—To a 0° C. solution of 40c (1.77 g, 5.3 mmol) in DCM (10 mL) was added BCl$_3$ (53 mL, 53 mmol of a 1M solution in DCM). The reaction mixture was stirred at RT for 3 h and quenched with water. The product was extracted into EtOAc (2×), and the combined extracts were washed with brine, dried (MgSO$_4$), filtered and concentrated in vacuo. The product was purified by SiO$_2$ chromatography eluting with EtOAc/hexanes to afford 1.1 g (77%) of 41: LCMS RT 1.6 min, M−H.

step 4—A solution of 41 (390 mg, 1.4 mmol), thionyl chloride (1.0 mL, 14 mmol), and DMF (0.2 mL) was heated at 80° C. for 3 days. The reaction mixture was concentrated in vacuo and azeotroped with toluene (2×), ether (2×), hexanes (2×), and DCM/hexanes (2×) to afford 350 mg (100%) of 42.

step 5—To a solution of 23 (R=CH$_2$-p-C$_6$H$_4$F) (370 mg, 1.4 mmol) in THF (10 mL) was added NaH (120 mg, 3.1 mmol) and the reaction stirred for 10 min. This mixture was then added to a solution of 42 (350 mg, 1.4 mmol) in THF (10 mL). The reaction was stirred for 1 h and concentrated in vacuo. The resulting residue was quenched with 1N HCl, and the product was extracted into EtOAc (2×). The combined organics were washed with water and brine, dried (MgSO$_4$), filtered and concentrated in vacuo. The product was purified by SiO$_2$ chromatography eluting with EtOAc/hexanes/acetic acid to afford 600 mg (90%) of 43: LCMS RT 2.5 min, M−H.

step 6—To a solution of methanesulfonamide (1.0 g, 13 mmol) in DMF (20 mL) was added NaH (500 mg, 13 mmol), and the reaction mixture was stirred at RT for 30 min. A solution of 43 (600 mg, 1.0 mmol) in DMF (10 mL) was added, and the reaction was stirred overnight. The reaction was poured into HCl (1M), and the product was extracted into EtOAc (2×). The combined organic extracts were washed with water (2×) and brine, dried (MgSO$_4$), filtered and concentrated in vacuo. The product was purified by SiO$_2$ chromatography eluting with EtOAc/DCM/HOAc to afford 400 mg (59%) of 1H-23 LCMS RT 1.9 min, M−H.

N-{3-[5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide was prepared as described in example 21 except in step 5, 23 (R=CH₂-p-C₆H₄F) was replaced with 5-tert-butyl-1-(4-fluoro-3-methyl-benzyl)-4-hydroxy-1,5-dihydro-pyrrol-2-one 23 (R=CH₂-4-F-3-Me-C₆H₃) to afford II-38.

N-{3-[5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-N,N-dimethylsulfamide was prepared as described in example 21 except in step 6, methanesulfonamide was replaced by N,N-dimethylsulfamide to afford 45 mg (19%) of II-39: LCMS RT 2.4 min, M−H.

N-{3-[5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-sulfamide was prepared as described in example 21 except in step 6, methanesulfonamide was replaced by N-BOC-sulfamide (CAS Reg. No. 148017-28-1; T. Matsui et al., *Org. Proc. Res. Dev.* 2004 8(3):408-410) to afford the N-BOC protected sulfamide which was deprotected with TFA (10 equivalents)/DCM at RT and the crude product purified by SiO₂ chromatography eluting with a MeOH/DCM gradient containing 0.7% HOAc (1 to 3% MeOH) to afford 100 mg of II-41: ms [M−H]=535.3.

Pyrrolidine-1-sulfonic acid {3-[5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared as described in example 21 except in step 6, methanesulfonamide was replaced by pyrrolidine-1-sulfonic acid amide to afford 45 mg (18%) of II-42: LCMS RT 2.5 min, M−H.

Cyclopropanesulfonic acid {3-[5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared as described in example 21 except in step 6, methanesulfonamide was replaced by cyclopropane-sulfonamide to afford 20 mg (11%) of II-45: LCMS RT 2.4 min, M−H.

Ethanesulfonic acid {3-[5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared as described in example 21 except in step 6, methanesulfonamide was replaced by ethanesulfonamide to afford 44 mg (25%) of II-46: LCMS RT 2.4 min, M−H.

2-({3-[5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amino)-acetamide was prepared as described in example 21 except in step 6, methanesulfonamide was replaced by 2-aminoacetamide to afford 20 mg (6%) of II-52: LCMS RT 2.7 min, M−H.

N-{3-[(S)-1-(3-Bromo-4-fluoro-benzyl)-5-tert-butyl-4-hydroxy-2-oxo-2,5-dihydro-1H-pyrrol-3-yl]-1,1-dioxo-1H-1λ⁶-benzo[d]isothiazol-7-ylmethyl}-methanesulfonamide was prepared as described in example 21 except in step 5, 23 (R=CH₂-p-C₆H₄F) was replaced with 5-tert-butyl-1-(3-bromo-4-fluoro-benzyl)-4-hydroxy-1,5-dihydro-pyrrol-2-one 23 (R=CH₂-3-Br-4-F—C₆H₃) to afford II-69.

N-{3-[(S)-5-Cyclohexyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide was prepared as described in example 21 except in step 5, 23 (R=CH₂-p-C₆H₄F) was replaced with (S)-5-cyclohexyl-1-(4-fluoro-benzyl)-4-hydroxy-1,5-dihydro-pyrrol-2-one to afford II-70. (S)-5-Cyclohexyl-1-(4-fluoro-benzyl)-4-hydroxy-1,5-dihydro-pyrrol-2-one was prepared from N-(cyclohexyl-ethoxycarbonyl-methyl)-N-(4-fluoro-benzyl)-malonamic acid ethyl ester which was in turn prepared from (αS)-α-amino-cyclohexaneacetic acid HCl salt (CAS Reg. No. 191611-20-8) by reductive amination and acylation of the secondary amine.

N-{3-[(S)-5-tert-Butyl-1-(2-cyclopentyl-ethyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide was prepared as described in example 21 except in step 5, 23 (R=CH₂-p-C₆H₄F) was replaced with (S)-5-tert-butyl-1-(2-cyclopentyl-ethyl)-4-hydroxy-1,5-dihydro-pyrrol-2-one to afford II-71.

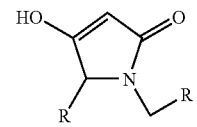

94: R = p-C₆H₄F

N-{3-[1-(4-Fluoro-3-methyl-benzyl)-5-(4-fluoro-phenyl)-4-hydroxy-2-oxo-2,5-dihydro-1H-pyrrol-3-yl]-1,1-dioxo-1H-1λ⁶-benzo[d]isothiazol-7-ylmethyl}-methanesulfonamide was prepared as described in example 21 except in step 5, 23 (R=CH₂-p-C₆H₄F) was replaced with 1-(4-fluoro-3-methyl-benzyl)-5-(4-fluoro-phenyl)-4-hydroxy-1,5-dihydro-pyrrol-2-one (94) to afford II-72.

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-benzenesulfonamide was prepared as described in example 21 except in step 6 methanesulfonamide was replaced by benzenesulfonamide to afford II-73.

Morpholine-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared by the procedure described for II-41 (supra) except N-Boc-sulfamide was replaced with 4-morpholinesulfonamide (CAS Reg. No. 25999-04-6). The crude product was purified by two SiO₂ chromatographies eluting with 2.5% EtOAc/DCM containing 0.7% HOAc to afford 0.052 g of II-90: ms [M−H]=605.3.

Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt was prepared by the procedure described for II-41 (supra) except N-Boc-sulfamide was replaced with 4-sulfamoyl-piperazine-1-carboxylic acid tert-butyl ester (CAS Reg. No. 162046-65-3; T. Shibata et al. WO2004083167) to afford II-91: ms [M−H]=604.4.

4-Acetyl-piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared by acetylation of II-91. To a solution of II-91 (0.14 g, 0.20 mmol) was added DIPEA (0.14 mL 0.78 mmol) and acetyl chloride (0.018 g, 0.23 mmol). The reaction mixture was stirred for 2 h at RT and worked up using standard procedures. Purification of the crude product by SiO₂ chromatography eluting with a MeOH/DCM gradient (2.5 to 5% MeOH) afforded 0.13 g of II-92: ms [M−H]=646.3.

Piperazine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt was prepared by the procedure described for II-91 except 43 (R=4-F-3-Me-C₆H₃CH₂) replaced 43 (R=4-F—C₆H₄CH₂) to afford 0.052 g of II-98: ms [M–H]=618.3.

Piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-methyl-amide; trifluoro-acetic acid salt was prepared by as described for II-41 except in step 6, methanesulfonamide was replaced by 4-(N-methylsulfamoyl)-piperazine-1-carboxylic acid tert-butyl ester which is prepared from piperazine-1-carboxylic acid tert-butyl ester (CAS Reg. No. 57260-71-6) and N-methylsulfamoyl chloride (CAS Reg. No. 10438-96-7). The preparation of piperazinyl-sulfamic acid amides is disclosed by P. Lehr in WO03/082842 published Oct. 9, 2003. The N-BOC protected sulfamide which was deprotected with TFA (10 equivalents)/DCM at RT and the crude product was azeotroped with hexane/DCM to afford 0.050 g of II-99: ms [M–H]=618.3.

3-Amino-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetate salt was prepared as described for II-99 except 4-(N-methylsulfamoyl)-piperazine-1-carboxylic acid tert-butyl ester was replaced with (1-sulfamoyl-pyrrolidin-3-yl)-carbamic acid tert-butyl ester. Removal of the BOC protecting group with DCM/TFA afforded 0.061 g of II-100: ms [M–H]=618.3.

N-[1-({3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-sulfamoyl)-pyrrolidin-3-yl]-acetamide was prepared by acetylation of II-100 with acetyl chloride and DIPEA in DMF and purified by SiO₂ chromatography eluting with 3% MeOH/DCM to afford 0.060 g (47%) of H-101: ms [M–H]=660.4.

3-Methanesulfonyl-pyrrolidine-1-sulfonic acid {3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-amide was prepared as described for II-100 except (1-sulfamoyl-pyrrolidin-3-yl)-carbamic acid tert-butyl ester was replaced with 3-methanesulfonyl-pyrrolidine-1-sulfonic acid amide and the BOC deprotection was omitted to afford 0.24 g (43%) of II-102: ms [M]=682.2.

EXAMPLE 22

N-{3-[5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-N-methyl-methanesulfonamide (II-35)

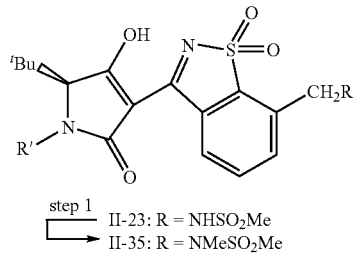

step 1
II-23: R = NHSO₂Me
II-35: R = NMeSO₂Me

R' = CH₂-p-C₆H₄F

To a solution of II-23 (60 mg, 0.11 mmol) in DMF was added NaH (10 mg, 0.3 mmol). The reaction mixture was stirred at RT for 30 min, and MeI (50 mg, 0.3 mmol) was added. After stirring for an additional 4 h at RT, the reaction was poured into 1M HCl, and the product was extracted into EtOAc (2×). The combined organics extracts were washed with water and brine, dried (MgSO₄), and concentrated in vacuo. The product was purified by crystallization from DCM/hexanes to afford 40 mg (65%) of II-35: LCMS RT 2.4 min. M–H.

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-N-methyl-methanesulfonamide was prepared analogously to II-35 and purified by SiO₂ chromatography eluting with 2.5% EtOAc/DCM containing 0.7% HOAc to afford II-77: mp 105-109° C.; ms [M–H]=562.3.

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-N-(2-methoxy-ethyl)-methanesulfonamide was prepared analogously to II-35 except methyl iodide was replaced with N-(2-methoxy-ethyl)-methanesulfonamide (CAS Reg. No. 93901-85-0) and sodium hydride was replaced with cesium carbonate. The product was purified by SiO₂ chromatography eluting with EtOAc/hexane gradient (50% then 80% EtOAc) to afford II-86: ms [M–H]=592.4.

EXAMPLE 23

(R)-5-tert-Butyl-3-(1,1-dioxo-1H-1λ⁶-benzo[d]isothiazol-3-yl)-1-(4-fluoro-benzyl)-4-hydroxy-1,5-dihydro-pyrrol-2-one (II-40)

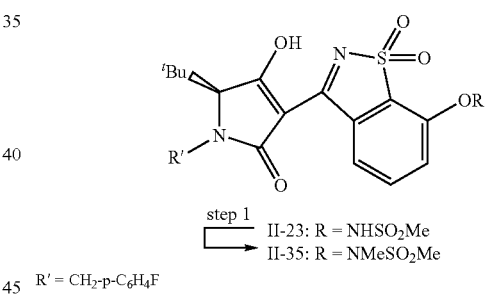

step 1
II-23: R = NHSO₂Me
II-35: R = NMeSO₂Me

R' = CH₂-p-C₆H₄F

To a solution of II-6 (80 mg, 0.18 mmol) in acetone (3 mL) was added K₂CO₃ (500 mg, 3.6 mmol) and 2-bromoacetamide (74 mg, 0.54 mmol). The reaction mixture was heated at reflux for 2 h, and the solvent was removed in vacuo. The mixture was diluted with 1M HCl, and the product was extracted into EtOAc (2×). The combined organic extracts were dried (MgSO₄) and concentrated in vacuo. The product was purified by column chromatography on SiO₂ eluting with DCM/MeOH to afford 45 mg, (50%) of II-40: LCMS RT 2.3 min, M–H.

EXAMPLE 24

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-yl}-methanesulfonamide (II-60)

A tube was charged with II-4 (0.100 g, 0.22 mmol), methanesulfonamide (0.041 g, 0.43 mmol), Cs₂CO₃ (0.14 g, 0.43 mmol), dicyclohexylphosphanyl-biphenyl-2-yl)-dimethyl-amine (0.013 g, 0.032 mmol), Pd$_2$(dba)$_3$ (0.0099 g, 0.011 mmol) and dioxane (1 mL). The reaction mixture was degassed with a stream of N$_2$. The tube was capped and heated to 100° C. for 20 h. The dioxane was evaporated in vacuo and the residue partitioned between EtOAc and 1M HCl. The EtOAc layer was removed and the aqueous layer twice extracted with EtOAc. The combined EtOAc extracts were dried (MgSO$_4$), filtered and evaporated. The crude product was purified by SiO$_2$ chromatography eluting with a hexane/EtOAc gradient (20% to 100% EtOAc) to afford 65 mg (58%) II-60 as an orange solid which was dried under high vacuum to remove traces of EtOAc: mp 245-250° C.

EXAMPLE 25

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-acetamide (II-53)

To a solution of II-51 (0.075 g, 0.17 mmol) in DCM was added pyridine (0.41 mL, 0.040 g, 0.51 mmol) and Ac$_2$O (0.048 mL, 0.052 g, 0.51 mmol) and the resulting solution was stirred at RT for 20 h. The mixture was diluted with EtOAc and extracted twice with 1M HCl, water and brine. The resulting solution was dried (MgSO$_4$), filtered and concentrated in vacuo. The residue was triturated with Et$_2$O and sonicated. Hexane was added to the Et$_2$O solution and the resulting precipitate was filtered and washed with hexane to afford 25 mg (30%) of II-53: mp 164-167° C.

EXAMPLE 26

{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-methanesulfonamide (II-64)

A solution of II-6 (0.010 g, 0.0225 mmol), bromomethanesulfonamide (0.0117 g, 0.0675 mmol) Cs$_2$CO$_3$ (0.147 g, 0.450 mmol), tetrabutylammonium iodide (catalytic amount) and DMF (3 mL) was heated to 85° C. overnight. The reaction mixture cooled to RT and the solvent evaporated in vacuo. The residual material was neutralized with 1N HCl and extracted with EtOAc. The organic layer was dried and concentrated to afford 17 mg of II-64: mp 165° C.

(S)-5-tert-Butyl-1-(4-fluoro-benzyl)-4-hydroxy-3-(7-isobutoxy-1,1-dioxo-1H-1$\lambda^6$-benzo[d]isothiazol-3-yl)-1,5-dihydro-pyrrol-2-one was prepared analogously except bromomethanesulfonamide was replaced by 1-iodo-2-methyl-propane and tetrabutylammonium iodide was omitted. The crude product was purified by SiO$_2$ chromatography eluting with a EtOAc/hexane gradient (30 to 50% EtOAc) to afford II-80: ms [M]=500.2.

(S)-5-tert-Butyl-1-(4-fluoro-benzyl)-4-hydroxy-3-(7-methanesulfonylmethoxy-1,1-dioxo-1H-1$\lambda^6$-benzo[d]isothiazol-3-yl)-1,5-dihydro-pyrrol-2-one was prepared from (S)-5-tert-butyl-1-(4-fluoro-benzyl)-4-hydroxy-3-(7-methylsulfanylmethoxy-1,1-dioxo-1H-1$\lambda^6$-benzo[d]isothiazol-3-yl)-1,5-dihydro-pyrrol-2-one (66). To a solution of 66 (0.079 g, 0.16 mmol) and DCM was added MCPBA (0.14 g, 0.64 mmol). After the starting material was consumed the reaction mixture was partitioned between EtOAc and 1.0 M HCl. The organic layer was separated, dried (Na$_2$SO$_4$), filtered and concentrated in vacuo. The residue was purified by SiO$_2$ chromatography eluting with an EtOAc/hexane gradient (50 to 90% EtOAc) to afford 0.084 g (100%) of II-81 as a yellow solid. mp 143-151° C., ms [M−H]=535.3.

The precursor 66 is prepared by alkylation of II-6 with chloromethylmethyl sulfide (CAS Reg No. 2373-51-5) as described for II-64 (supra)

EXAMPLE 27

2-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-acetamide (II-65)

A solution of II-6 (0.100 g, 0.2250 mmol), N-methyl 2-chloroacetamide (0.09678 g, 0.899 mmol), K$_2$CO$_3$ (0.6219 g, 4.5 mmol), KI (0.0373 g, 0.2250 mmol) and acetone (5 mL) was heated at reflux for 3 h. The reaction mixture was cooled to RT and the solvent removed in vacuo. The residue was partitioned between EtOAc and 1N HCl. The layers were separated and the aqueous layer extracted with EtOAc. The combined EtOAc extracts were dried (Na$_2$SO$_4$), filtered and evaporated in vacuo. The crude product was purified by SiO$_2$ chromatography eluting with 3% MeOH/DCM to afford 0.022 g of II-65: mp contracts at 175° C., mp>225° C.

EXAMPLE 28

1-tert-Butyl-4-(1,1-dioxo-1H-1$\lambda^6$-benzo[d]isothiazol-3-yl)-2-(4-fluoro-benzyl)-5-hydroxy-1,2-dihydro-pyrazol-3-one (III-2, SCHEME 9)

step 1—To a suspension of 1-tert-butylhydrazine hydrochloride (5.0 g, 40 mmol) in ether (200 mL) was added TEA (5.6 mL, 40 mmol) and 4-fluorobenzaldehyde (5.0 g, 40 mmol). After stirring at room temperature for 30 min, MgSO$_4$ (5.8 g, 48 mmol) was added. The resulting reaction mixture was stirred at RT for 2 d and filtered. The filtrate was evaporated under reduced pressure which afforded 7.0 g (90%) of 60a which was used in step 2 without additional purification.

step 2 To a solution of the hydrazone 60a (1.65 g, 8.5 mmol) in EtOAc (50 mL) was added pyridine (0.82 mL, 10.2 mmol) followed by ethyl 3-chloro-3-oxopropanoate (1.3 mL, 10.2 mmol). After stirring at RT for 3 h, the reaction mixture was filtered. The filtrate was evaporated under reduced pressure which afforded 2.6 g (100%) of 60b used in step 3 without additional purification.

step 3—The hydrazone 60b (2.6 g, 8.5 mmol) was dissolved in EtOH (50 mL), and 10% Pd/C (90 mg, 0.85 mmol) was added. The reaction mixture was maintained under a H$_2$ atmosphere (1 atm pressure) at RT for 12 h. The reaction was filtered and the solvent was removed under reduced pressure. The resulting yellow oil was taken up in EtOAc, washed with water, dried (MgSO$_4$), filtered and the solvent was removed under reduced pressure. The product was purified by column chromatography on SiO$_2$ eluting with EtOAc/hexanes to afford 2.5 g (95%) of 61: LCMS RT 3.0 min, did not ionize well.

step 4—To a solution of the hydrazine 61 (400 mg, 1.3 mmol) in THF (5 mL) was added NaH (100 mg, 2.6 mmol). After heating for 30 min at reflux, the reaction was quenched with saturated aqueous NH$_4$Cl and extracted into EtOAc (2×). The combined organics were dried (MgSO$_4$), filtered and the solvent was removed under reduced pressure to afford 300 mg (88%) of 62a: LCMS RT 2.0 min, does not ionize well.

step 5—To a solution of the pyrazolone 62a (300 mg, 1.1 mmol) in THF (5 mL) was added NaH (54 mg, 1.4 mmol). The reaction mixture was stirred at RT for 20 min, and 3-chloro-benzo[d]isothiazole 1,1-dioxide (270 mg, 1.4 mmol) was added. The reaction mixture was then stirred at RT for 2 h, quenched with saturated aqueous NH$_4$Cl and extracted into ethyl acetate (2×). The combined organics were dried (MgSO$_4$), filtered and the solvent was removed under reduced pressure. The crude product was purified by reverse-phase column chromatography eluting with acetonitrile/water which afforded 15 mg (3%) of III-2; LCMS RT 2.3 min, M−H.

EXAMPLE 29

1-(2-Cyclopropyl-ethyl)-3-(1,1-dioxo-1H-1λ$^6$-benzo [d]isothiazol-3-yl)-6-fluoro-4-hydroxy-1H-quinolin-2-one (III-1)

Sodium hydride was suspended in THF and 63 was added as a solid. Hydrogen evolution observed and within 1-2 min the solution was homogeneous. The mixture was stirred for 1 h at RT, at which point the enolate precipitated out of solution. The reaction mixture was heated to 60° C. and 26 was added. Immediately, the mixture became a homogeneous yellow solution. The reaction mixture was stirred at 60° C. and monitored by HPLC and stirring was continued until the quinolindione consumed. Added additional NaH and saccharin chloride along with toluene and raised the temperature to 80° C. After addition was completed, the reaction mixture was stirred overnight. The HPLC revealed two product peaks and two additional peaks presumably for saccharin chloride and the quinolindione starting materials, however LCMS (Southpark) only shows a single product peak and ionization was only observed in negative ion mode. After stirring overnight the quinolindione consumed. The reaction mixture was concentrated in vacuo and the residue extracted with DCM (3×). The combined extracts were dried (Na$_2$SO$_4$), filtered and concentrated in vacuo. The crude mixture was purified by SiO$_2$ chromatography eluting with EtOAc/hexanes (1:1). A non-polar spot highly visible under long wave UV light was first to elute followed by the product, which eluted with other impurities visible under long wave UV light. The top spot was checked by LCMS and gave a positive ion mode mass of 578, which corresponds to the addition of two saccharin units. In negative ion mode a mass of 411 was observed. This material was collected (17 mg) and hydrolyzed with 1N NaOH for ca. 1 h. The mixture was neutralized with HCl and extracted with EtOAc (3×). The combined organic phases were washed with brine, dried (Na$_2$SO$_4$). Multiple columns with hexane/EtOAc (2:1, 3% HOAC) and hexane/DCM/EtOAc/MeOH (2:1:0.5, 2% MeOH) afforded 13.5 mg of III-1 which contained an impurity.

EXAMPLE 30

1-{3-[(S)-5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-3-methylurea (II-74)

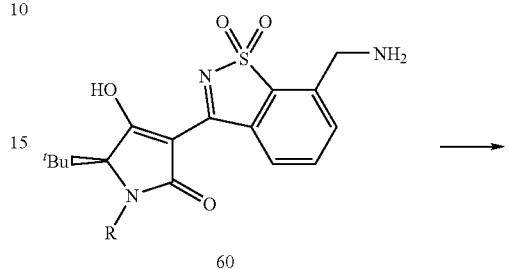

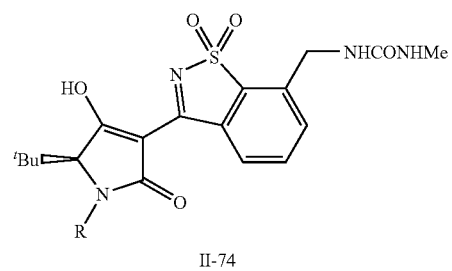

R = CH$_2$—4-F—C$_6$H$_4$

To a solution of 60 (0.19 g, 0.12 mmol), DIPEA (0.75 mL, 4.2 mmol) and THF was added methylisocyanate and the reaction stirred for 1 h. Several drops of MeOH were added and the mixture was stirred for 20 min. The reaction mixture was concentrated in vacuo and partitioned between 1 N HCl and EtOAc. The aqueous layer was extracted with EtOAc and the combined organic extracts washed with brine, dried (MgSO$_4$), filtered and concentrated in vacuo. The crude product was purified by SiO$_2$ chromatography eluting a MeOH/DCM gradient (2 to 5% MeOH) to afford 0.06 g of II-74: mp>250° C.

EXAMPLE 31

(S)-5-tert-Butyl-1-(4-fluoro-benzyl)-4-hydroxy-3-[7-(2-methanesulfonyl-ethyl)-1,1-dioxo-1H-1λ$^6$-benzo [d]isothiazol-3-yl]-1,5-dihydro-pyrrol-2-one (II-75)

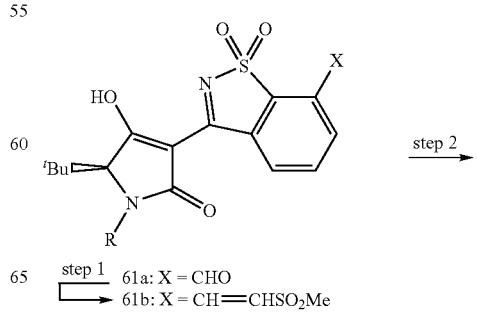

step 1   61a: X = CHO
→ 61b: X = CH═CHSO$_2$Me

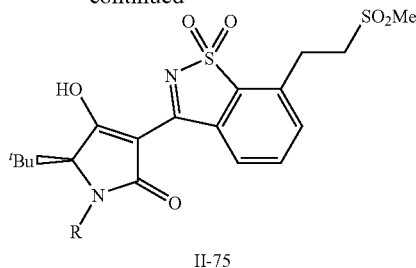

II-75

R = CH₂—4-F—C₆H₄

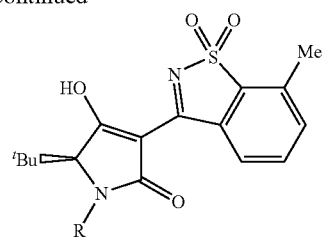

II-76

R' = CH₂—4-F—C₆H₄ step 1—To a solution of diethyl methylsulfonylmethylphosphonate (0.098 g, 0.43 mmol) and THF was added NaH (0.034 g, 0.85 mmol, 60% in mineral oil) and the reaction was stirred at RT for 20 min. The aldehyde 61a (0.13 g, 0.28 mmol) was added and the reaction stirred for 1 h at which time the LCMS shows mostly vinyl sulfone. The reaction was poured into water containing HCl (1 mL). The organics were immediately extracted with EtOAc, washed with brine, dried (MgSO₄), filtered and concentrated in vacuo. The crude product was purified by SiO₂ chromatography eluting a gradient of 1:1 EtOAc/hexane to 5% EtOAc/DCM containing 0.7% HOAc to afford 61b. The product thus obtained was used directly in step 2.

step 2—To a solution of 61b (0.050 g, 0.094 mmol) in MeOH (20 mL) was added ammonium formate (0.059 g, 0.94 mmol) and the resulting solution degassed with N₂ and Pd/C (~15 mg) was added. The solution degassed with H₂ and maintained under an H₂ atmosphere with stirring for 1 h. The reaction was filtered through CELITE® and filter cake washed with MeOH (50 mL). The filtrate was concentrated in vacuo and partitioned between EtOAc and HCl (1 N). The combined organic extracts were washed with brine, dried (MgSO₄), filtered and concentrated in vacuo. The residue was purified by SiO₂ chromatography eluting with 6% EtOAc/DCM containing 0.7% HOAc to afford 0.025 g (50%) of II-75: mp 127-135° C.

EXAMPLE 32

(S)-5-tert-Butyl-1-(4-fluoro-benzyl)-4-hydroxy-3-(7-methyl-1,1-dioxo-1H-1λ⁶-benzo[d]isothiazol-3-yl)-1,5-dihydro-pyrrol-2-one (II-76)

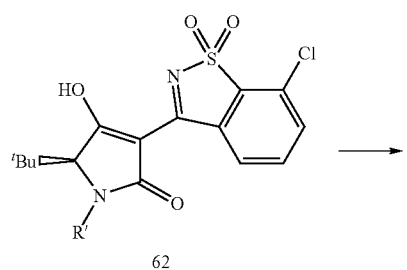

62

A mixture of II-3 (0.150 g, 0.324 mmol), cesium fluoride (0.148 g, 0.972 mmol), methylboronic acid (0.0582 g, 0.972 mmol), (2'-dicyclohexylphosphanyl-biphenyl-2-yl)-dimethyl-amine (0.0191 g, 0.0486 mmol), Pd(OAc)₂ (0.00727 g, 0.0324 mmol) and dioxane (1 mL) was purged with N₂ and heated at reflux for 18 h The reaction mixture was partitioned between EtOAc and 1M HCl. The aqueous layer was separated and extracted once with EtOAc. The combined organic extracts were washed with brine, dried (MgSO₄), filtered and concentrated in vacuo. The crude product was purified by SiO₂ chromatography eluting with a EtOAc/hexane gradient (25, 33 then 40% EtOAc) to afford 103 mg (71.8%) of II-76 as a greenish-yellow solid: mp>250° C.

EXAMPLE 33

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-sulfamide (II-78)

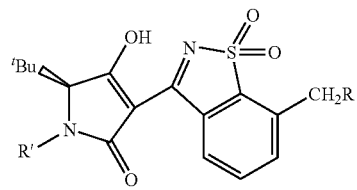

step 1 ⌐ 63a: R = Cl
       └→ 63b: R = NHSO₂NH—BOC
step 2 └→ II-78: R = NHSO₂NH₂

R = CH₂—(4-F—3-Me—C₆H₃)

The chloromethyl precursor 63a was prepared as described in steps 1-5 of example 21 except in step 5, 23 (R=CH₂-p-C₆H₄F) was replaced with 23 (R=CH₂-(4-F-3-Me-C₆H₃).

step 1—The displacement of the benzylic chloride was carried out as described in step 6 of example 21, except methansulfonamide was replaced by N-(tert-butoxycarbonyl)sulfamide to afford 63b.

step 2—To a solution of 63b (0.30 g, 0.461 mmol) and DCM was added TFA (0.526 g, 4.61 mmol) and the reaction was stirred at RT for 2 h. The reaction mixture was concentrated in vacuo and purified by $SiO_2$ chromatography eluting with a MeOH/DCM gradient containing 0.7% HOAc (1 to 3% MeOH) to afford II-78.

EXAMPLE 34

2-Amino-ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide; hydrochloride salt (II-79)

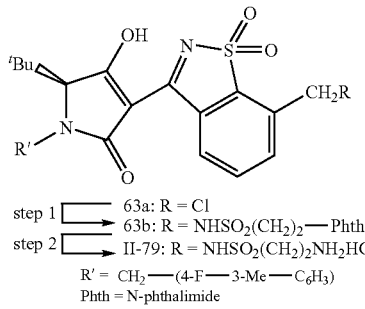

step 1 ⎡ 63a: R = Cl
       ⎣→ 63b: R = NHSO$_2$(CH$_2$)$_2$—Phth
step 2 ⎣→ II-79: R = NHSO$_2$(CH$_2$)$_2$NH$_2$HCl salt R' = CH$_2$—(4-F—3-Me—C$_6$H$_3$)
Phth = N-phthalimide $R^1$=CH$_2$-(4-F-3-Me-C$_6$H$_3$) Phth=N-phthalimide step 1—To a solution of 63a (0.20 g, 0.42 mmol) in MeOH was added a 2M methanolic ammonia solution. The reaction was stirred in a sealed tube for 4 days. The reaction mixture was evaporated and the residue re-dissolved in DCM and re-evaporated. The crude amine was dissolved in DMF and DIPEA (0.30 mL, 1.7 mmol) and 1,3-dihydro-1,3-dioxo-2H-isoindole-2-ethanesulfonyl chloride (0.16 g, 0.59 mmol, CAS Reg. No. 4403-36-5) was added and the reaction mixture stirred overnight at RT. The reaction mixture was partitioned between EtOAc and dilute aqueous HCl. The aqueous phase was separated and extracted with EtOAc. The combined EtOAc extracts were washed water and brine, dried (MgSO4), filtered and concentrated in vacuo. The crude product was purified by $SiO_2$ eluting with 5% EtOAc/hexane containing 0.7% HOAc to afford 63b.

step 2—

To a solution of the 63b (0.12 g, 0.17 mmol) and DCM was added hydrazine and the reaction mixture stirred overnight at RT. The reaction was concentrated in vacuuo. The crude product was re-dissolved in DCM and gaseous HCl was introduced. The solid was filtered and re-suspended in DCM and the suspension filtered through CELITE® and the cake washed with DCM. The DCM extracts were dried and evaporated to afford II-79: mp 172-179° C., ms [M−H]=565.2

EXAMPLE 35

Dimethyl-sulfamic acid 3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl ester (II-82)

The title compound is prepared by treating II-6 with dimethylsulfamoyl chloride and DIPEA in THF to afford II-82: mp 116-126° C.

EXAMPLE 36

{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide (II-83)

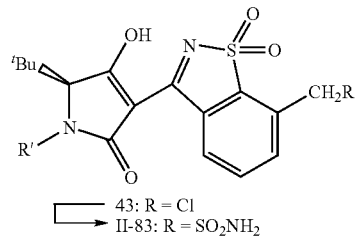

43: R = Cl
→ II-83: R = SO$_2$NH$_2$

R' = CH$_2$-p-C$_6$H$_4$F

The procedure is that of A. M. Baskin and Z. Wang, *Tetrahedron Lett.* 2002 43:8479-8483. To a solution of 43 (0.113 g, 0.237 mmol, SCHEME 8) and DMSO was added one equivalent of 3-sulfino-propanoic acid 1-methyl ester sodium salt (0.413 g, 2.37 mmol, CAS Reg No. 90030-48-1). After 1 h the reaction appeared sluggish and 9 additional equivalents of sulfinic acid sodium salt were. The reaction was stirred overnight at RT. To the resulting reaction mixture was added NaOMe (0.512 g, 2.37 mmol, 25% solution in MeOH) and the reaction was stirred for 10 min. Finally, an aqueous solution of hydroxylamino-O-sulfonic acid (0.804 g, 7.11 mmol) and sodium acetate (0.466 g, 5.69 mmol) was added and the reaction stirred for 1 h. The reaction was poured into HCl (1N, 250 mL) and filtered. The solid collected was washed with water and redissolved into DCM. The organic solution was washed with HCl (1N) and brine, dried (MgSO$_4$), filtered and concentrated in vacuo. The crude product was purified by $SiO_2$ chromatographed eluting with a EtOAc/hexane gradient (5 to 15% EtOAc) containing 0.7% HOAc to afford 0.05 g (40.5%) of II-83: ms [M−H]=520.4.

EXAMPLE 37

N-{3-[(S)-5-tert-Butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-N',N'-dimethyl-sulfamide (II-84)

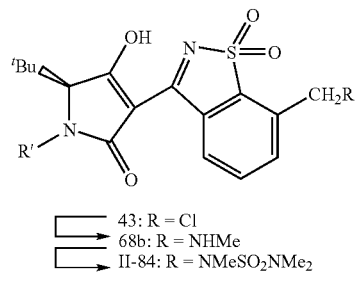

43: R = Cl
→ 68b: R = NHMe
→ II-84: R = NMeSO$_2$NMe$_2$

R' = CH$_2$-p-C$_6$H$_4$F

To a solution of 43 (0.25 g, 0.524 mmol) in MeOH was added methyl amine (1.63 g, 52.4 mmol, 2.0 M methanolic solution) and the resulting solution was stirred in a sealed tube overnight at RT. The solvents were evaporated to afford 68b. To a solution of 68b (0.24 g, 0.51 mmol) in DCM was added sequentially DIPEA (0.27 mL, 1.5 mmol) and dimethyl sulfamoyl chloride (0.088 g, 0.61 mmol). The resulting reaction mixture was stirred for 3 h and concentrated in vacuo. The residue was partitioned between EtOAc and aqueous HCl. The organic phase was separated, washed with brine, dried (MgSO$_4$), filtered and evaporated. The crude product was purified by SiO$_2$ chromatography eluting with 2.5% EtOAc/DCM containing 0.7% HOAc to afford 0.100 g (34%) of 1H-84: ms [M]=578.2.

EXAMPLE 38

(S)-5-tert-Butyl-3-[7-(1,1-dioxo-1λ$^6$-[1,2]thiazinan-2-ylmethyl)-1,1-dioxo-1H-1λ$^6$-benzo[d]isothiazol-3-yl]-1-(4-fluoro-benzyl)-4-hydroxy-1,5-dihydro-pyrrol-2-one (II-85)

A 25 mL flask was charged with NaH (0.0377 g, 0.7862 mmol, 50% in mineral oil) and a mixture of THF (1.5 mL) and DMF (0.5 mL) was added. A solution of [1,2]thiazinane 1,1-dioxide (0.1063 g, 0.7862 mmol) in DMF was added and the resulting solution stirred for 1 h after which solid 43 (0.075 g, 0.1572 mmol) was added in one batch. The vial containing 43 was washed with DMF (0.5 mL) and transferred to the reaction mixture via pipet. The resulting yellow mixture was stirred at RT and monitored by HPLC for consumption of starting material. After stirring for 72 h, the HPLC analysis showed 23% starting material remaining. The reaction mixture was heated to 45° C. for an additional 20 h. The reaction mixture was cooled to RT and H$_2$O (2 mL) and 1N HCl (1 mL) were added. The resulting mixture was thrice extracted with EtOAc. The combined EtOAc extracts were washed with brine, dried (Na$_2$SO$_4$), filtered and concentrated in vacuo. The crude mixture was purified by SiO$_2$ chromatography (Biotage 40S column) eluting with 3:1 hexane/EtOAc to remove the non-polar impurities. The product was removed from the column, concentrated in vacuo, and rechromatographed (Biotage 40S column) eluting with 5% DCM/MeOH. The material obtained was dissolved in DCM, passed through a syringe filter and concentrated in vacuo. The recovered product was dissolved in EtOAc and washed with 1N HCl (10 mL). The organic phase was washed with brine, dried (Na$_2$SO$_4$), filtered and concentrated in vacuo to afford II-85 as a yellow foam. The material was dissolved in a minimal amount of DCM and the solid precipitated with hexane to afford 29.7 mg (32.8%) of II-85: ms [M−H]=574.2.

(S)-5-tert-Butyl-3-[7-(1,1-dioxo-1λ$^6$-[1,2,5]thiadiazolidin-2-ylmethyl)-1,1-dioxo-1H-1λ$^6$-benzo[d]isothiazol-3-yl]-1-(4-fluoro-benzyl)-4-hydroxy-1,5-dihydro-pyrrol-2-one was prepared in analogously except for the alkylation of 67a, [1,2]thiazinane 1,1-dioxide was replaced with 1,2,5-thiadiazolidine 1,2-dimethyl-ethyl ester 1,1-dioxide (CAS Reg No. 263719-76-2) to afford 70. Then sulfamide 70 (0.0892 g, 0.1346 mmol) was dissolved in 2-3 mL DCM (3 mL) and then TFA (1 mL) was added. The mixture was stirred overnight at RT. The mixture was concentrated in vacuo and the crude residue was purified by SiO$_2$ chromatography (Biotage 40S) eluting with EtOAc/hexane gradient (33% to 100% EtOAc) to afford 30 mg of II-88; ms [M−H]=561.4.

EXAMPLE 39

N-{3-[(S)-5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-N-(2-methylamino-ethyl)-methanesulfonamide; hydrochloride salt (II-87)

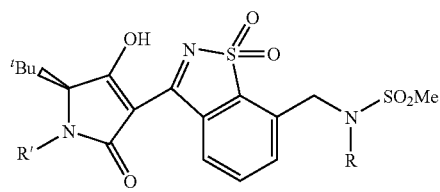

step 1 → II-23: R = H
69: R = (CH$_2$)$_2$N(BOC)Me
step 2 → II-87: R = (CH$_2$)$_2$NHMe R' = CH$_2$-p-C$_6$H$_4$F step 1—The sulfonamide II-23 is prepared by the procedure described for II-86 in Example 22 except methyl iodide is replaced with (2-chloro-ethyl)-methyl-carbamic acid tert-butyl ester (CAS Reg. No. 220074-38-4).

step 2—The carbamate 69 (0.045 g, 0.065 mmol) was dissolved in 1,4-dioxane (0.5 mL) and HCl (4.0M in dioxane) was added. The reaction mixture was stirred at RT until deprotection was complete to afford 0.037 g of II-87: ms [M]+=592.2.

EXAMPLE 40

C-{3-[(S)-5-tert-Butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yloxy}-N-methyl-methanesulfonamide (II-89)

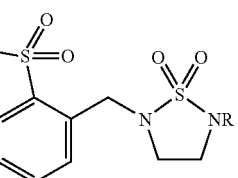

70: R = BOC
II-88: R = H

R' = CH$_2$-p-C$_6$H$_4$F

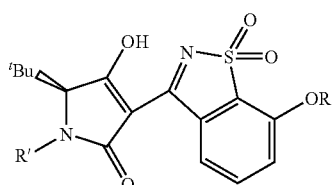

II-6: R = H
II-89: R = CH$_2$SO$_2$NHMe

R' = CH$_2$-p-C$_6$H$_4$F

To a solution of II-6 (0.115 g, 0.259 mmol) in DMF (2 mL) was added $Cs_2CO_3$ (0.337 g, 1.03 mmol) and C-bromo-N-methyl-methanesulfonamide (0.0681 g, 0.362 mmol). The reaction mixture was heated at 55° C. for 4 h, cooled to 0° C., quenched with 3.0 M aqueous HCl (3.0 M) and partitioned between water and EtOAc. The organic layer was separated, dried ($Na_2SO_4$), filtered and concentrated in vacuo. The residue was purified by $SiO_2$ chromatography eluting with 80% EtOAc/hexanes to afford II-89 as a yellow solid: ms [M−H]= 550.3.

EXAMPLE 41

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-propionyl-methanesulfonamide (II-93)

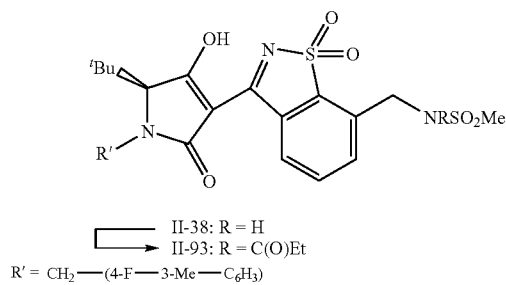

II-38: R = H
II-93: R = C(O)Et
R' = $CH_2$—(4-F—3-Me—$C_6H_3$)

To a solution of II-38 (0.097 g, 0.18 mmol), DMAP (0065 g, 0.53 mmol) and THF (3 mL) was added propionic anhydride (0.2 mL, 1.8 mmol). The reaction was stirred at RT for 2.2 h. The reaction mixture was partitioned between water and EtOAc. The EtOAc solution was washed with 0.5 M $KHSO_4$, dried ($Na_2SO_4$), filtered and concentrated in vacuo. The residue was suspended in DCM and warmed with a heat gun to dissolve the solid which precipitated and was filtered to afford II-93: mp 98.0-99.8° C.

EXAMPLE 42

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-butyryl-methanesulfonamide (II-94)

To a solution of II-38 (0.560 g; 0.82 mmol; approximately 80% pure), butyric acid (0.9 mL, 0.98 mmol), DIPEA (0.72 mL), DMAP (one crystal) and THF (5 mL) was added EDCI (0.185 g, 0.98 mmol) and the reaction was stirred at RT. After 3 days HPLC analysis indicated ca 20% starting material, 5% bis-acylated product and 65% of the desired product was present. An additional 0.09 mL of butyric acid and 160 mg of EDCI was added and stirring continued for another 4 days. To the solution was added $K_2CO_3$ (330 mg), water (5 mL) and THF (20 mL) and the resulting mixture stirred for 15 min then partitioned between 0.5M $KHSO_4$ and EtOAc. The organic phase was dried ($Na_2SO_4$), filtered and concentrated in vacuo. The crude product was purified by $SiO_2$ chromatography eluting with an EtOAc/hexane gradient (50 to 66% EtOAc) to afford 220 mg of II-94: mp 225.7-226.5° C.

EXAMPLE 43

(S)-5-tert-Butyl-1-(4-fluoro-benzyl)-4-hydroxy-3-(7-methylaminomethyl-1,1-dioxo-1H-1$\lambda^6$-benzo[d]isothiazol-3-yl)-1,5-dihydro-pyrrol-2-one; compound with 2,2,3,3,4,4,4-heptafluoro-butyric acid (II-95)

The title compound was prepared from 43 (0.25 g, 0.524 mmol) and methanolic methyl amine (26.2 mL, 52.4 mmol) in a sealed tube. The reaction mixture was concentrated in vacuo and purified by HPLC. The eluent contain heptafluoropropionic acid which afforded I-95 as the perfluoropropioate salt: mp 162-168° C.

II-96 and II-97 were prepared analogously using methanolic dimethylamine and methanolic ammonia respectively.

EXAMPLE 44

C-{3-[(S)-5-tert-Butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-yloxy}-N,N-dimethyl-methanesulfonamide

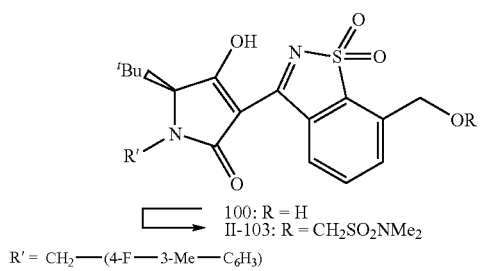

100: R = H
II-103: R = $CH_2SO_2NMe_2$
R' = $CH_2$—(4-F—3-Me—$C_6H_3$)

A mixture of 100 (0.150 g, 0.327 mmol), bromo-N,N-dimethylmethanesulfonamide (0.0992 g, 0.491 mmol, CAS Reg. No. 51270-39-4) and $Cs_2CO_3$ (0.426 g, 1.31 mmol) in DMA (3 mL) was heated at 55° C. for 16 h then 100° C. for 4 h. Little reaction was apparent by LCMS so an additional portion of bromo-N,N-dimethyl-methanesulfonamide (0.0992 g, 0.491 mmol) was added and stirring was continued for an additional 20 h. The reaction was cooled to RT, and quenched with 1M HCl. The product was twice extracted into EtOAc and the combined organic layers were washed with brine, dried ($MgSO_4$), filtered and purified via preparative TLC (4:1 EtOAc:hexane) to give 35 mg of a yellow foamy solid. A second prep TLC plate (1:1 hexane:EtOAc) was run to afford 20 mg (11%) of II-103: ms [M−H]=578.3.

EXAMPLE 45

(S)-5-tert-Butyl-3-[7-(1,1-dioxo-1λ⁶-[1,2,6]thiadi-azinan-2-ylmethyl)-1,1-dioxo-1H-1λ⁶-benzo[d]isothiazol-3-yl]-1-(4-fluoro-benzyl)-4-hydroxy-1,5-dihydro-pyrrol-2-one (II-104)

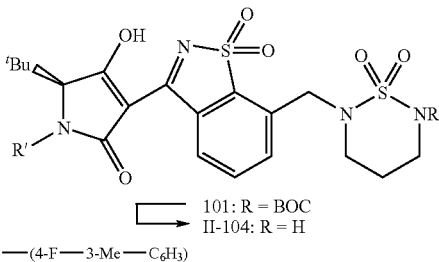

101: R = BOC
II-104: R = H

R' = CH$_2$—(4-F—3-Me—C$_6$H$_3$)

1,1-Dioxo-1λ⁶-[1,2,6]thiadiazinane-2-carboxylic acid tert-butyl ester can be prepared by the procedure described by K. C. Nicolau et al., *Angew. Chem. Int. Ed.* (English) 2002 41(20):3866-3870. The monoprotected thiadiazinane was reacted with the corresponding chloromethyl derivative to afford 101 as disclosed in example 21.

To a solution of 101 (0.0531 g, 0.0785 mmol) and DCM (1.5 mL) was added TFA (0.604 ml, 7.85 mmol) at RT via pipet. The resulting yellow solution was stirred at RT and monitored by LCMS. After 3 h, the starting material was consumed. The reaction mixture was concentrated.

The residue was taken up in DCM and hexanes added until a the product precipitated. The product was dried under high vacuum to afford 0.0403 g (89%) of II-104: ms [M−H]= 575.4.

EXAMPLE 46

Thiophene-2-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide (II-105)

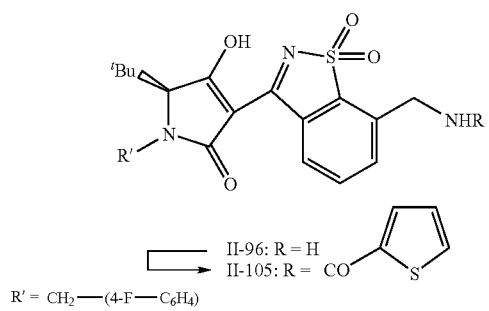

II-96: R = H
II-105: R = CO—[thiophene]

R' = CH$_2$—(4-F—C$_6$H$_4$)

To a solution of the II-97 (0.2 g, 0.44 mmol), DIPEA (0.24 mL, 1.3 mmol) and DCM was added thiophene-2-sulfonyl chloride and the reaction was stirred overnight RT. The reaction was next concentrated in vacuo and the solid dissolved in EtOAc. The EtOAc solution was washed HCl (1N), brine and dried (MgSO$_4$). The crude product was purified by SiO$_2$ chromatography eluting with an EtOAc/DCM gradient containing 0.7% HOAc to afford 0.076 g (19%) of II -105: ms [M−H]=602.4.

1,2-Dimethyl-1H-imidazole-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; trifluoro-acetic acid salt was prepared as described above except thiophene-2-sulfonyl chloride was replaced with 1,2-dimethyl-1H-imidazole-4-sulfonyl chloride to afford 0.095 g (32.8%) of II-106.

EXAMPLE 47

HCV NS5B RNA Polymerase Activity

The enzymatic activity of HCV NS5B570n-BK is measured as incorporation of radiolabeled nucleotide monophosphates into acid insoluble RNA products. Unincorporated radiolabel substrate is removed by filtration and scintillant is added to the washed and dried filter plate containing radiolabeled RNA product. The light emitted by the scintillant is proportional to the amount of RNA product generated by NS5B570n-BK at the endpoint of the reaction.

The N-terminally histidine tagged HCV polymerase, derived from HCV BK strain, genotype 1b (NS5B570n-BK) contains a 21 amino acid deletion at the C-terminus relative to the full-length HCV polymerase and is purified from *E. coli* strain M15. The construct containing the coding sequence of HCV BK strain amino acid residues 2421-2999 (GenBank accession number M58335) downstream of a Taq promoter expression cassette was inserted into plasmid constructs. The plasmid constructs are transformed in *E. coli* and colonies are inoculated and grown overnight in 10 L of Terrific broth (Tartoff and Hobbs) supplemented with 100 μg/mL ampicillin at 37° C. Protein expression is induced by addition of 1 mM isopropyl-β-D -thiogalactopyranoside (IPTG), when optical densities reaches between 1.5 and 3.5 OD$_{600}$ and the culture is then incubated for 16- to 18 h at 22° C. NS5B570n -BK is purified to homogeneity using a three step protocol including subsequent column chromatography on Ni-NTA, SP-Sepharose HP and Superdex 75 resins.

Each 50 μl enzymatic reaction contains 8:4 μg/mL poly A:oligo U$_{16}$ (template:primer), 200 nM NS5B570n-BK enzyme, 2.1 μCi of tritiated UTP (Perkin Elmer catalog no. TRK -412; specific activity: 30 to 60 Ci/mmol; stock solution concentration from $7.5 \times 10^{-5}$ M to $20.6 \times 10^{-6}$ M), 1 μM ATP, CTP, and GTP, 40 mM Tris-HCl pH 8.0, 2 to 40 mM NaCl, 4 mM DTT (dithiothreitol), 4 mM MgCl$_2$, and 5 μl of compound serial diluted in DMSO. Reaction mixtures are assembled in MADVN0B 96-well filter plates (Millipore Co.) and incubated for 2 h at 30° C. Reactions are stopped by addition of 10% (v/v) trichloroacetic acid and incubated for 40 min at 4° C. Reactions are filtered, washed with 6 reaction volumes of 10% (v/v) trichloroacetic acetic acid, 2 reaction volumes of 70% (v/v) ethanol, air dried, and 25 μl of scintillant (Microscint 20, Perkin-Elmer) is added to each reaction well.

The amount of light emitted from the scintillant is converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data is analyzed with GraphPad® Prism® and/or Microsoft® Excel®. The reaction in the absence of enzyme is used to determine the background signal, which is subtracted from the enzymatic reactions. Positive control reactions are performed in the absence of compound, from which the background corrected activity is set as 100% polymerase activity.

All data is expressed as a percentage of the positive control. The compound concentration at which the enzyme-catalyzed rate of RNA synthesis is reduced by 50% ($IC_{50}$) is calculated by fitting equation (i) to $$Y = \% \text{Min} + \frac{(\% \text{Max} - \% \text{Min})}{\left[1 + \frac{X}{(IC_{50})^S}\right]} \quad (i)$$

the data, where "Y" corresponds to the relative enzyme activity (in %), "% Min" is the residual relative enzymatic activity at saturating compound concentration, "% Max" is the maximal relative enzymatic activity compared to positive control, X corresponds to the compound concentration, and "S" is the Hill coefficient (or slope). Representative data is in Table 4 (infra).

EXAMPLE 48

*Renilla luciferase* Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a replicon construct NK5.1 (Krieger et al., *J. Virol.* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

*Renilla luciferase* HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960). All the reagents described in the following paragraph were included in the manufacturer's kit, and the manufacturer's instructions were followed for preparations of the reagents. The cells were washed twice with 200 μl of phosphate buffered saline (pH 7.0) (PBS) per well and lysed with 25 μl of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 μl of Stop & Glob reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microliter of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

TABLE 4

| Compound Number | Polymerase Assay $IC_{50}$ (μM) | R. luciferase Activity $IC_{50}$ (μM) |
| --- | --- | --- |
| II-6  | 0.052 | 3.257 |
| II-23 | 0.076 | 0.056 |
| II-15 | 0.138 | 0.125 |
| II-35 | 0.154 | 0.108 |
| II-31 | 0.208 | 0.288 |
| II-41 | —     | 0.058 |
| II-38 | —     | 0.035 |
| II-64 |       | 0.228 |
| II-77 | —     | 0.129 |
| II-81 | —     | 0.235 |
| II-91 |       | 0.143 |

EXAMPLE 49

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

| Parenteral Formulation (D) | |
|---|---|
| Ingredient | % wt./wt. |
| Active ingredient | 0.25 g |
| Sodium Chloride | q.s. to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

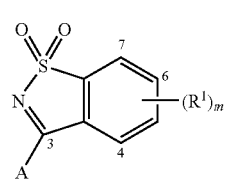

wherein:

A is A-3;

$X^1$ is a bond;

$R^1$ in each occurrence is independently selected from the group consisting of $C_{1-6}$ alkyl, $C_{1-6}$ alkenyl, $C_{1-6}$ alkynyl, $C_{3-7}$ cycloalkyl, $C_{3-7}$ cycloalkyl-$C_{1-4}$ alkyl, $C_{1-6}$ alkoxy, optionally substituted phenyl, optionally substituted heteroaryl selected from the group consisting of pyridine, pyridone, pyrimidine, pyrimidone, pyrazole and imidazole, optionally substituted aryl-$C_{1-6}$ alkyl, $C_{1-6}$ hydroxyalkyl, $C_{1-3}$ alkoxy-$C_{1-6}$ alkyl, optionally substituted phenoxy, optionally substituted phenyl-$C_{1-3}$ alkoxy, $C_{1-6}$ heteroalkoxy, hydroxyl, halogen, $(CH_2)_{o_1}NR^aR^b$, $X^2(CH_2)_uNR^aR^b$, $X^2(CH_2)_{o_1}COR^9$, $X^2(CH_2)_{o_1}SO_2NR^cR^d$, $(CH_2)_{r_1}SO_2R^5$, $O(CH_2)_{o_1}SO_2$—$C_{1-6}$ alkyl, $COR^9$, nitro, and cyano wherein optionally substituted phenyl or heteroaryl groups are independently substituted with one to three substituents selected from the group consisting of $C_{1-3}$ alkyl, $C_{3-6}$ cycloalkyl, $C_{1-3}$ alkoxy, $C_{1-3}$ haloalkyl, halogen, $NR^cR^d$, cyano and nitro;

$R^2$ in each occurrence is independently selected from the group consisting of $C_{1-6}$ alkyl, pyrid-2-on-5-ylmethyl, thien-2-ylmethyl, $C_{3-7}$ cycloalkyl, $C_{3-7}$ cycloalkyl-$C_{1-3}$ alkyl, and phenyl-$C_{1-3}$ alkyl optionally substituted with one to three substituents selected from the group consisting of $C_{1-3}$ alkyl, $C_{3-6}$-cycloalkyl, $C_{1-3}$ alkoxy, $C_{1-3}$ haloalkyl, halogen, $NR^cR^d$, cyano and nitro;

$R^4$ is hydrogen, $C_{1-6}$ alkyl, $C_{3-7}$ cycloalkyl, $C_{3-7}$ cycloalkyl-$C_{1-4}$ alkyl, $C_{1-6}$ heteroalkyl, phenyl or phenyl-$C_{1-4}$ alkyl said phenyls optionally independently substituted with one to three groups selected from the group consisting of $C_{1-6}$ alkyl, halogen, $C_{1-6}$ alkoxy, hydroxyl, cyano and nitro;

$R^5$ is $C_{1-6}$ alkyl, $C_{3-7}$ cycloalkyl, $C_{3-7}$ cycloalkyl-$C_{1-4}$ alkyl, —$NR^cR^d$, amino-$C_{1-6}$ alkyl, $C_{1-6}$ heteroalkyl, thiophen-2-yl, 1,2-dimethyl-imidazol-4-yl, phenyl or phenyl-$C_{1-3}$ alkyl said phenyl each optionally independently substituted with one to three $C_{1-3}$ alkyl, $C_{1-3}$ alkoxy, halogen, nitro or cyano;

$R^{6a}$ and $R^{6b}$ are independently hydrogen or $C_{1-3}$ alkyl;

$R^8$ is $C_{1-6}$ acyl or hydrogen or $C_{1-3}$ alkyl;

$R^9$ is hydroxyl, $C_{1-6}$ alkoxy, amino, $-NR^cR^d$, providing that $R^9$ is other than hydroxyl when $o_1$ is zero;

$R^{10}$ is alkoxy, amino, $-NR^cR^d$, $C_{1-6}$ alkyl, $C_{3-7}$ cycloalkyl or $C_{1-6}$ heteroalkoxy;

$R^a$ and $R^b$ are (i) independently hydrogen, $C_{1-6}$ alkyl, $C_{1-6}$ acyl, $C_{1-6}$ heteroalkyl, $C_{1-6}$ alkyl-$C_{1-3}$ alkoxy, $C_{1-3}$ alkyl-amino-$C_{1-6}$ alkyl, or (ii) one of $R^a$ and $R^b$ is $(CH_2)_{r_2}$ $CONR^{6a}R^{6a}$, $COR^{10}$ or $(CH_2)_{o_2}SO_2R^5$, and the other of $R^a$ and $R^b$ is hydrogen, $C_{1-6}$ alkyl or $C_{1-6}$ acyl, or (iii) taken together are $(CH_2)_q$, $(CH_2)_wSO_2$, $(CH_2)_w$ $NR^{6a}SO_2$, $(CH_2)_2X^3(CH_2)_2$, or taken together with the nitrogen atom to which they are attached are 3-amino pyrrolidine, 3-methylsulfonylpyrrolidine or 3-acetamido-pyrrolidine;

$R^c$ and $R^d$ are (i) independently hydrogen, $C_{1-6}$ alkyl, $C_{1-6}$ acyl, $C_{1-6}$ sulfonyl or $C_{1-6}$ heteroalkyl, or (ii) taken together are $(CH_2)_q$, $(CH_2)_2X^3(CH_2)_2$, or 3-hydroxy-pyrrolidin-1-yl;

$X^2$ is O, or $NR^{6a}$;

$X^3$ is O or $NR^8$;

m is an integer from 0 to 3;

$o_1$ and $o_2$ are independently integers from 0 to 6;

q is an integer from 3 to 6;

$r_1$ and $r_2$ are independently integers from 1 to 6;

u is an integer from 2 to 6;

w is an integer from 2 to 4; and, pharmaceutically acceptable salts thereof.

2. A compound of claim 1 wherein:

$R^1$ is hydroxyl, $(CH_2)_{o_1}NR^aR^b$, $X^2(CH_2)_uNR^aR^b$, $X^2(CH_2)_{o_1}COR^9$, $X^2(CH_2)_{o_1}SO_2NR^cR^d$, $(CH_2)_{r_1}$ $SO_2R^5$, optionally substituted aryl, optionally substituted heteroaryl or halogen;

$R^2$ is $C_{1-6}$ alkyl, aryl-$C_{1-4}$ alkyl or $C_{3-7}$ cycloalkyl-$C_{1-4}$ alkyl; and, $R^4$ is hydrogen, $C_{1-6}$ alkyl, $C_{3-7}$ cycloalkyl, aryl or aryl-$C_{1-4}$ alkyl said aryl optionally substituted independently with one to three groups selected from the group consisting of $C_{1-6}$ alkyl, halogen, $C_{1-6}$ alkoxy, hydroxyl, cyano and nitro.

3. A compound of claim 2 wherein m is one, $R^1$ is $(CH_2)_{o_1}$ $NR^aR^b$, $X^2(CH_2)_{o_1}COR^9$ or $X^2(CH_2)_{o_1}SO_2NR^cR^d$ and $R^5$ is $C_{1-6}$ alkyl, $C_{3-7}$ cycloalkyl, $C_{3-7}$ cycloalkyl-$C_{1-4}$ alkyl or $NR^cR^d$.

4. A compound according to claim 3 wherein the $R^1$ substituent is attached to the 7-position of the 1,1-dioxo-1H-1$\lambda^6$-benzo[d]isothiazol-3-yl ring.

5. A compound according to claim 4 wherein $R^1$ is $(CH_2)_{o_1}$ $NR^aR^b$, and $o_1$ is an integer from zero to two, $R^a$ is $(CH_2)_{o_2}$ $SO_2R^5$, $o_2$ is zero and $R^b$ is hydrogen.

6. A compound according to claim 4 wherein $R^1$ is $X^2(CH_2)_{o_1}SO_2NR^cR^d$, $X^2$ is O, $o_1$ is an integer from one to three.

7. A compound according to claim 4 wherein $R^1$ is $X^2(CH_2)_{o_1}COR^9$, $X^2$ is O, $o_1$ is an integer from one to three.

8. A compound according to claim 2 wherein $R^1$ is optionally substituted aryl or optionally substituted heteroaryl ring and the $R^1$ substituent is attached to the 7-position of the 1,1-dioxo-1H-1$\lambda^6$-benzo[d]isothiazol-3-yl ring.

9. A method for treating a Hepatitis C Virus (HCV) infection comprising administering to a patient in need thereof, a therapeutically effective quantity of a compound according to claim 1.

10. The method of claim 9 further comprising co-administering at least one immune system modulator selected from the group consisting of interferon α-2a, interferon α-2b, PEGASYS and PEGINTRON and/or at least one antiviral selected from ribavirin or viramidine.

11. The method of claim 10 wherein the immune system modulator is selected from the group consisting of interferon α-2a, interferon α-2b, PEGASYS and PEGINTRON.

12. The method of claim 10 wherein the antiviral compound is ribavirin or viramidine.

13. A pharmaceutical composition comprising a therapeutically effective quantity of a compound according to claim 1 admixed with at least one pharmaceutically acceptable carrier, diluent or excipient.

14. A compound according to claim 1 selected from the group consisting of:

(S)-1-benzyl-5-cyclohexyl-3-(1,1-dioxo-1H-1$\lambda^6$-benzo[d]isothiazol-3-yl)-4-hydroxy-1,5-dihydro-pyrrol-2-one;

(S)-1-benzyl-5-tert-butyl-3-(1,1-dioxo-1-H-1$\lambda^6$-benzo[d]isothiazol-3-yl)-4-hydroxy-1,5-dihydro-pyrrol-2-one;

5-tert-butyl-3-(1,1-dioxo-1H-1$\lambda^6$-benzo[d]isothiazol-3-yl)-1-(4-fluoro-benzyl)-4-hydroxy-1,5-dihydro-pyrrol-2-one;

5-tert-butyl-3-(7-chloro-1,1-dioxo-1-H-1$\lambda^6$-benzo[d]isothiazol-3-yl)-1-(4-fluoro-benzyl)-4-hydroxy-1,5-dihydro-pyrrol-2-one;

(S)-5-tert-butyl-1-(4-fluoro-benzyl)-4-hydroxy-3-(7-methoxy-1,1-dioxo-1H-1$\lambda^6$-benzo[d]isothiazol-3-yl)-1,5-dihydro-pyrrol-2-one;

5-tert-butyl-1-(4-fluoro-benzyl)-4-hydroxy-3-(7-hydroxy-1,1-dioxo-1H-1$\lambda^6$-benzo[d]isothiazol-3-yl)-1,5-dihydro-pyrrol-2-one;

(S)-5-tert-butyl--3-(1,1-dioxo-1H-1$\lambda^6$-naphtho[2,1-d]isothiazol-3-yl)-1-(4-fluoro-benzyl)-4-hydroxy-1,5-dihydro-pyrrol-2-one;

(S)-3-(7-chloro-1,1-dioxo-1H-1$\lambda^6$-benzo[d]isothiazol-3-yl)-1-(4-fluoro-benzyl)-4-hydroxy-5-isobutyl-1,5-dihydro-pyrrol-2-one;

(S)-5-tert-butyl-3-(1,1-dioxo-1H-1$\lambda^6$-benzo[d]isothiazol-3-yl)-4-hydroxy-1-(4-methyl-benzyl)-1,5-dihydro-pyrrol-2-one;

(S)-5-tert-butyl-3-(1,1-dioxo-1H-1$\lambda^6$-benzo[d]isothiazol-3-yl)-1-(4-fluoro-3-methoxy-benzyl)-4-hydroxy-1,5-dihydro-pyrrol-2-one;

(S)-5-tert-butyl-3-(1,1-dioxo-1H-1$\lambda^6$-benzo[d]isothiazol-3-yl)-4-hydroxy-1-thiophen-2-ylmethyl-1,5-dihydro-pyrrol-2-one;

(S)-5-cyclohexyl-3-(1,1-dioxo-1H-1$\lambda^6$-benzo[d]isothiazol-3-yl)-1-(4-fluoro-benzyl)-4-hydroxy-1,5-dihydro-pyrrol-2-one; sodium salt;

(S)-5-tert-butyl-1-(4-chloro-benzyl)-3-(1,1-dioxo-1H-1$\lambda^6$-benzo[d]isothiazol-3-yl)-4-hydroxy-1,5-dihydro-pyrrol-2-one;

4-[(S)-2-tert-butyl-4-(1,1-dioxo-1H-1$\lambda^6$-benzo[d]isothiazol-3-yl)-3-hydroxy-5-oxo-2,5-dihydro-pyrrol-1-ylmethyl]-benzonitrile;

(S)-5-tert-butyl-3-(1,1-dioxo-1H-1$\lambda^6$-benzo[d]isothiazol-3-yl)-1-(4-fluoro-3-methyl-benzyl)-4-hydroxy-1,5-dihydro-pyrrol-2-one;

(S)-5-((S)-sec-butyl)-3-(1,1-dioxo-1H-1$\lambda^6$-benzo[d]isothiazol-3-yl)-1-(4-fluoro-benzyl)-4-hydroxy-1,5-dihydro-pyrrol-2-one;

(S)-5-tert-butyl-1-cyclobutylmethyl-3-(1,1-dioxo-1H-1$\lambda^6$-benzo[d]isothiazol-3-yl)-4-hydroxy-1,5-dihydro-pyrrol-2-one;

(S)-3-(1,1-dioxo-1H-1λ$^6$-benzo[d]isothiazol-3-yl)-1-(4-fluoro-benzyl)-4-hydroxy-5-isobutyl-1,5-dihydro-pyrrol-2-one;

3-(1,1-dioxo-1H-1λ$^6$-benzo[d]isothiazol-3-yl)-1-(4-fluoro-benzyl)-4-hydroxy-5-isobutyl-1,5-dihydro-pyrrol-2-one;

(R)-3-(1,1-dioxo-1H-1λ$^6$-benzo[d]isothiazol-3-yl)-1-(4-fluoro-benzyl)-4-hydroxy-5-isobutyl-1,5-dihydro-pyrrol-2-one;

(S)-5-tert-butyl-1-(3,3-dimethyl-butyl)-3-(1,1-dioxo-1H-1λ$^6$-benzo[d]isothiazol-3-yl)-4-hydroxy-1,5-dihydro-pyrrol-2-one;

(S)-1-(3-bromo-4-fluoro-benzyl)-5-tert-butyl-3-(1,1-dioxo-1H-1λ$^6$-benzo[d]isothiazol-3-yl)-4-hydroxy-1,5-dihydro-pyrrol-2-one;

N-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-methanesulfonamide;

(S)-5-tert-butyl-1-(3,4-difluoro-benzyl)-3-(1,1-dioxo-1H-1λ$^6$-benzo[d]isothiazol-3-yl)-4-hydroxy-1,5-dihydro-pyrrol-2-one;

5-[(S)-2-tert-butyl-4-(1,1-dioxo-1H-1λ$^6$-benzo[d]isothiazol-3-yl)-3-hydroxy-5-oxo-2,5-dihydro-pyrrol-1-ylmethyl]-2-fluoro-benzonitrile;

(S)-5-tert-butyl-3-(1,1-dioxo-1H-1λ$^6$-benzo[d]isothiazol-3-yl)-1-(4-fluoro-3-trifluoromethyl-benzyl)-4-hydroxy-1,5-dihydro-pyrrol-2-one;

(S)-3-(1,1-dioxo-1H-1λ$^6$-benzo[d]isothiazol-3-yl)-1-(4-fluoro-benzyl)-4-hydroxy-5-phenyl-1,5-dihydro-pyrrol-2-one;

(S)-5-benzyl-3-(1,1-dioxo-1H-1λ$^6$-benzo[d]isothiazol-3-yl)-1-(4-fluoro-benzyl)-4-hydroxy-1,5-dihydro-pyrrol-2-one;

5-[(S)-2-tert-butyl-4-(1,1-dioxo-1H-1λ$^6$-benzo[d]isothiazol-3-yl)-3-hydroxy-5-oxo-2,5-dihydro-pyrrol-1-ylmethyl]-1H-pyridin-2-one;

(S)-5-tert-butyl-1-(3-cyclopropyl-4-fluoro-benzyl)-3-(1,1-dioxo-1H-1λ$^6$-benzo[d]isothiazol-3-yl)-4-hydroxy-1,5-dihydro-pyrrol-2-one;

(S)-5-tert-butyl-1-(3-chloro-4-fluoro-benzyl)-3-(1,1-dioxo-1H-1λ$^6$-benzo[d]isothiazol-3-yl)-4-hydroxy-1,5-dihydro-pyrrol-2-one;

(S)-5-tert-butyl-3-(1,1-dioxo-7-pyridin-3-yl-1H-1λ$^6$-benzo[d]isothiazol-3-yl)-1-(4-fluoro-benzyl)-4-hydroxy-1,5-dihydro-pyrrol-2-one;

(S)-5-tert-butyl-1-(4-fluoro-benzyl)-4-hydroxy-3-[7-(6-methoxy-pyridin-3-yl)-1,1-dioxo-1H-1λ$^6$-benzo[d]isothiazol-3-yl]-1,5-dihydro-pyrrol-2-one;

5-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyridin-2-one;

N-{3-[5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-N-methyl-methanesulfonamide;

(S)-5-tert-butyl-1-(4-fluoro-benzyl)-4-hydroxy-3-[7-(2-methoxy-pyrimidin-5-yl)-1,1-dioxo-1H-1λ$^6$-benzo[d]isothiazol-3-yl]-1,5-dihydro-pyrrol-2-one;

N-(3-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-phenyl)-acetamide;

N-{3-[5-tert-butyl-1-(4-fluoro-3-methyl-benzyl)-4-hydroxy-2-oxo-2,5-dihydro-1H-pyrrol-3-yl]-1,1-dioxo-1H-1λ$^6$-benzo[d]isothiazol-7-ylmethyl}-methanesulfonamide;

dimethylamino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amide;

2-{3-[5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yloxy}-acetamide;

amino-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amide;

pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amide;

5-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyrimidin-2-one;

(S)-5-tert-butyl-3-(1,1-dioxo-7-pyrimidin-5-yl-1H-1λ$^6$-benzo[d]isothiazol-3-yl)-1-(4-fluoro-benzyl)-4-hydroxy-1,5-dihydro-pyrrol-2-one;

cyclopropanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amide;

ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amide;

6-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-1H-pyridin-2-one;

(S)-5-tert-butyl-3-[1,1-dioxo-7-(1H-pyrazol-4-yl)-1H-1λ$^6$-benzo[d]isothiazol-3-yl]-1-(4-fluoro-benzyl)-4-hydroxy-1,5-dihydro-pyrrol-2-one;

(R)-5-tert-butyl-3-(1,1-dioxo-1H-1λ$^6$-benzo[d]isothiazol-3-yl)-1-(4-fluoro-benzyl)-4-hydroxy-1,5-dihydro-pyrrol-2-one;

(S)-5-tert-butyl-3-(1,1-dioxo-1H-1λ$^6$-benzo[d]isothiazol-3-yl)-1-(3-ethyl-4-fluoro-benzyl)-4-hydroxy-1,5-dihydro-pyrrol-2-one;

(S)-3-(7-amino-1,1-dioxo-1H-1λ$^6$-benzo[d]isothiazol-3-yl)-5-tert-butyl-1-(4-fluoro-benzyl)-4-liydroxy-1,5-dihydro-pyrrol-2-one;

2-({3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-amino)-acetamide;

N-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-yl}-acetamide;

(S)-5-tert-butyl-3-[7-(1,1-dioxo-1λ$^6$-isothiazolidin-2-ylmethyl)-1,1-dioxo-1H-1λ$^6$-benzo[d]isothiazol-3-yl]-1-(4-fluoro-benzyl)-4-hydroxy-1,5-dihydro-pyrrol-2-one;

N-{3-[(S)-5-tert-butyl-1-(4-fluoro-benzyl)-4-hydroxy-2-oxo-2,5-dihydro-1H-pyrrol-3-yl]-1,1-dioxo-1H-1λ$^6$-benzo[d]isothiazol-7-ylmethyl}-N-methylcarbamoylmethyl-acetamide;

N-{3-[(S)-5-tert-butyl-1-(4-fluoro-3-methoxy-benzyl)-4-hydroxy-2-oxo-2,5-dihydro-1H-pyrrol-3-yl]-1,1-dioxo-1H-1λ$^6$-benzo[d]isothiazol-7-ylmethyl}-methanesulfonamide;

2-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-N,N-dimethyl-acetamide;

2-({3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amino)-N-methyl-acetamide;

N-{3-[(S)-5-tert-butyl-1-(3-chloro-4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide;

2-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N,N-dimethyl-acetamide;

(S)-5-tert-butyl-1-(2-cyclopropyl-ethyl)-3-(1,1-dioxo-1H-1$\lambda^6$-benzo[d]isothiazol-3-yl)-4-hydroxy-1,5-dihydro-pyrrol-2-one;

(S)-3-(1,1-dioxo-1H-1$\lambda^6$-benzo[d]isothiazol-3-yl)-1-(4-fluoro-benzyl)-4-hydroxy-5-isopropyl-1,5-dihydro-pyrrol-2-one;

{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-methanesulfonamide;

2-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-acetamide;

2-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetamide;

{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylamino}-acetic acid ethyl ester;

(S)-3-hydroxy-pyrrolidine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

N-{3-[(S)-1-(3-bromo-4-fluoro-benzyl)-5-tert-butyl-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-cyclohexyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-butyl-1-(2-cyclopentyl-ethyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[1-(4-fluoro-3-methyl-benzyl)-5-(4-fluoro-phenyl)-4-hydroxy-2-oxo-2,5-dihydro-1H-pyrrol-3-yl]-1,1-dioxo-1H-1$\lambda^6$-benzo[d]isothiazol-7-ylmethyl}-methanesulfonamide;

N-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-benzenesulfonamide;

1-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-3-methyl-urea;

(S)-5-tert-butyl-1-(4-fluoro-benzyl)-4-hydroxy-3-[7-(2-methanesulfonyl-ethyl)-1,1-dioxo-1H-1$\lambda^6$-benzo[d]isothiazol-3-yl]-1,5-dihydro-pyrrol-2-one;

(S)-5-tert-butyl-1-(4-fluoro-benzyl)-4-hydroxy-3-(7-methyl-1,1-dioxo-1H-1$\lambda^6$-benzo[d]isothiazol-3-yl)-1,5-dihydro-pyrrol-2-one;

N-{3-[(S)-5-tert-butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-methanesulfonamide;

N-{3-[(S)-5-tert-butyl-1-(4-fluoro-3-methyl-benzyl)-4-hydroxy-2-oxo-2,5-dihydro-1H-pyrrol-3-yl]-1,1-dioxo-1H-1$\lambda^6$-benzo[d]isothiazol-7-ylmethyl}-sulfamide;

2-amino-ethanesulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

(S)-5-tert-butyl-1-(4-fluoro-benzyl)-4-hydroxy-3-(7-isobutoxy-1,1-dioxo-1H-1$\lambda^6$-benzo[d]isothiazol-3-yl)-1,5-dihydro-pyrrol-2-one;

(S)-5-tert-butyl-1-(4-fluoro-benzyl)-4-hydroxy-3-(7-methanesulfonylmethoxy-1,1-dioxo-1H-1$\lambda^6$-benzo[d]isothiazol-3-yl)-1,5-dihydro-pyrrol-2-one;

dimethyl-sulfamic acid 3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl ester;

{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yl}-methanesulfonamide;

N-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-methyl-N',N'-dimethyl-sulfamide;

(S)-5-tert-butyl-3-[7-(1,1-dioxo-1$\lambda^6$-[1,2]thiazinan-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one;

N-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-(2-methoxy-ethyl)-methanesulfonamide;

N-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-N-(2-methylamino-ethyl)-methanesulfonamide;

(S)-5-tert-butyl-3-[7-(1,1-dioxo-1$\lambda^6$-[1,2,5]thiadiazolidin-2-ylmethyl)-1,1-dioxo-1H-1$\lambda^6$-benzo[d]isothiazol-3-yl]-1-(4-fluoro-benzyl)-4-hydroxy-1,5-dihydro-pyrrol-2-one;

C-{3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-yloxy}-N-methyl-methanesulfonamide;

morpholine-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

4-acetyl-piperazine-1-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1$\lambda^6$-benzo[d]isothiazol-7-ylmethyl}-amide;

N-{3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-N-propionyl-methanesulfonamide;

N-{3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-ylmethyl}-N-butyryl-methanesulfonamide;

(S)-5-tert-butyl-1-(4-fluoro-benzyl)-4-hydroxy-3-(7-methylaminomethyl-1,1-dioxo-1H-1λ⁶-benzo[d]isothiazol-3-yl)-1,5-dihydro-pyrrol-2-one;

(S)-5-tert-butyl-3-(7-dimethylaminomethyl-1,1-dioxo-1H-1λ⁶-benzo[d]isothiazol-3-yl)-1-(4-fluoro-benzyl)-4-hydroxy-1,5-dihydro-pyrrol-2-one;

(S)-3-(7-aminomethyl-1,1-dioxo-1H-1λ⁶-benzo[d]isothiazol-3-yl)-5-tert-butyl-1-(4-fluoro-benzyl)-4-hydroxy-1,5-dihydro-pyrrol-2-one;

C-{3-[(S)-5-tert-butyl-1-(4-fluoro-3-methyl-benzyl)-4-hydroxy-2-oxo-2,5-dihydro-1H-pyrrol-3-yl]-1,1-dioxo-1H-1λ⁶-benzo[d]isothiazol-7-yloxy}-N,N-dimethyl-methanesulfonamide;

(S)-5-tert-butyl-3-[7-(1,1-dioxo-1λ⁶-[1,2,6]thiadiazinan-2-ylmethyl)-1,1-dioxo-1H-1λ⁶-benzo[d]isothiazol-3-yl]-1-(4-fluoro-benzyl)-4-hydroxy-1,5-dihydro-pyrrol-2-one;

thiophene-2-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; and, 1,2-dimethyl-1H-imidazole-4-sulfonic acid {3-[(S)-5-tert-butyl-1-(4-fluoro-benzyl)-4-hydroxy-2-oxo-2,5-dihydro-1H-pyrrol-3-yl]-1,1-dioxo-1H-1λ⁶-benzo[d]isothiazol-7-ylmethyl}-amide; or, a pharmaceutically acceptable salt thereof.

15. A compound according to claim 1 selected from the group consisting of II-98, II-99, II-100, II-101 and II-102 wherein the compounds have the following structure:

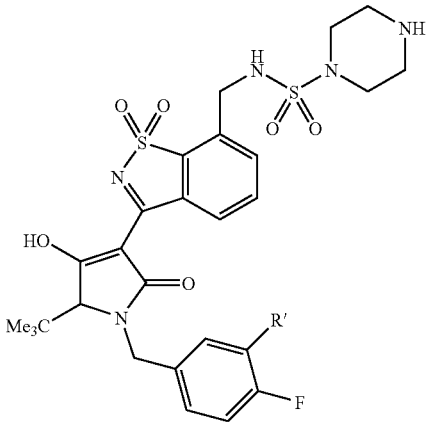

II-98: R' = Me
II-99: R' = H

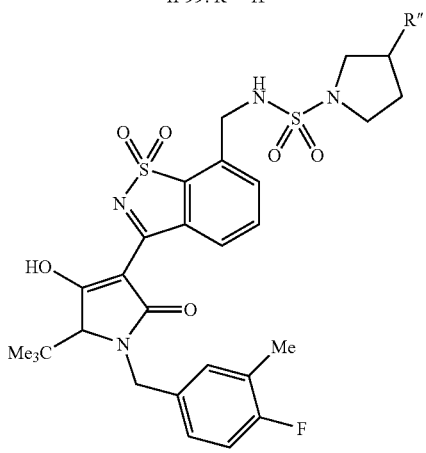

II-100: R" = NH₂
II-101: R" = NHC(=O)Me
II-102: R" = SO₂Me or, a pharmaceutically acceptable salt thereof.

* * * * *